(12) United States Patent
Zolotukhin et al.

(10) Patent No.: US 11,767,346 B2
(45) Date of Patent: *Sep. 26, 2023

(54) MODIFIED AAV CAPSID PROTEINS AND USES THEREOF

(71) Applicants: University of Florida Research Foundation, Incorporated, Gainesville, FL (US); The UAB Research Foundation, Birmingham, AL (US)

(72) Inventors: Sergei Zolotukhin, Gainesville, FL (US); Sanford L. Boye, Gainesville, FL (US); Shannon E. Boye, Gainesville, FL (US); Damien Marsic, Rockville, MD (US); Paul D. Gamlin, Birmingham, AL (US)

(73) Assignees: University of Florida Research Foundation, Incorporated, Gainesville, FL (US); The UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/689,324

(22) Filed: Mar. 8, 2022

(65) Prior Publication Data

US 2022/0267383 A1 Aug. 25, 2022

Related U.S. Application Data

(63) Continuation of application No. 17/009,536, filed on Sep. 1, 2020, now Pat. No. 11,332,502, which is a continuation of application No. 16/547,532, filed on Aug. 21, 2019, now Pat. No. 10,793,606, which is a continuation of application No. PCT/US2018/019050, filed on Feb. 21, 2018.

(60) Provisional application No. 62/625,486, filed on Feb. 2, 2018, provisional application No. 62/461,770, filed on Feb. 21, 2017.

(51) Int. Cl.
| | |
|---|---|
| *C07K 14/005* | (2006.01) |
| *C12N 15/10* | (2006.01) |
| *C12N 15/86* | (2006.01) |
| *C12N 7/00* | (2006.01) |

(52) U.S. Cl.
CPC ........ *C07K 14/005* (2013.01); *C12N 15/1037* (2013.01); *C12N 15/86* (2013.01); *C12N 7/00* (2013.01); *C12N 2320/32* (2013.01); *C12N 2750/14011* (2013.01); *C12N 2750/14121* (2013.01); *C12N 2750/14122* (2013.01); *C12N 2750/14143* (2013.01); *C12N 2750/14145* (2013.01)

(58) Field of Classification Search
CPC .. C07K 14/005; C12N 15/1037; C12N 15/86; C12N 7/00; C12N 2750/14121; C12N 2750/14145; C12N 2320/32; C12N 2750/14011; C12N 2750/14122; C12N 2750/14143; C12N 15/10; A61P 27/02

See application file for complete search history.

(56) References Cited

U.S. PATENT DOCUMENTS

| | | |
|---|---|---|
| 6,156,303 A | 12/2000 | Russell et al. |
| 7,186,552 B2 | 3/2007 | Wilson et al. |
| 7,220,577 B2 | 5/2007 | Zolotukhin |
| 7,927,585 B2 | 4/2011 | Snyder |
| 8,445,267 B2 | 5/2013 | Zhong et al. |
| 9,157,098 B2 | 10/2015 | Zhong et al. |
| 9,677,088 B2 | 6/2017 | Nakai et al. |
| 9,725,485 B2 | 8/2017 | Srivastava et al. |
| 10,011,640 B2 | 7/2018 | Srivastava et al. |
| 10,308,957 B2 | 6/2019 | Boye et al. |
| 10,426,844 B2 | 10/2019 | Agbandje-McKenna et al. |
| 10,648,000 B2 | 5/2020 | Hauswirth et al. |
| 10,723,768 B2 | 7/2020 | Zhong et al. |
| 10,793,606 B2 | 10/2020 | Zolotukhin et al. |
| 10,815,279 B2 | 10/2020 | Srivastava et al. |
| 11,000,597 B2 | 5/2021 | Muzyczka et al. |
| 11,091,777 B2 | 8/2021 | Marsic et al. |
| 11,332,502 B2 | 5/2022 | Zolotukhin et al. |
| 2004/0219575 A1 | 11/2004 | Neuman et al. |
| 2005/0106700 A1 | 5/2005 | Nomura et al. |
| 2006/0127358 A1 | 6/2006 | Muzyczka et al. |
| 2006/0188484 A1 | 8/2006 | Rabinowitz et al. |
| 2007/0036760 A1 | 2/2007 | Wilson et al. |

(Continued)

FOREIGN PATENT DOCUMENTS

| | | |
|---|---|---|
| EP | 1486567 A1 | 12/2004 |
| EP | 1 487 501 B1 | 12/2012 |

(Continued)

OTHER PUBLICATIONS

Dalkara D, Byrne LC, Klimczak RR, Visel M, Yin L, Merigan WH, Flannery JG, Schaffer DV. In vivo-directed evolution of a new adeno-associated virus for therapeutic outer retinal gene delivery from the vitreous. Sci Transl Med. Jun. 12, 2013;5(189):189ra76. (Year: 2013).*

(Continued)

*Primary Examiner* — Rachel B Gill
(74) *Attorney, Agent, or Firm* — Wolf, Greenfield & Sacks, P.C.

(57) ABSTRACT

Adeno associated viral (AAV) particles are emerging as a useful vehicle for gene delivery to various organs and tissues, one of them being the retina. Provided here are variant AAV (for example, variant serotype 2 (AAV2)) capsid proteins and variant capsid protein containing particles with enhanced ability to transduce retinal cells.

19 Claims, 36 Drawing Sheets

Specification includes a Sequence Listing.

(56) References Cited

U.S. PATENT DOCUMENTS

| | | |
|---|---|---|
| 2007/0196275 A1 | 8/2007 | Li et al. |
| 2008/0269149 A1 | 10/2008 | Bowles et al. |
| 2009/0075357 A1 | 3/2009 | Snyder |
| 2009/0197338 A1 | 8/2009 | Vandenberghe et al. |
| 2009/0286321 A1 | 11/2009 | Warrington et al. |
| 2012/0009268 A1* | 1/2012 | Asokan ............... A61P 9/00 435/456 |
| 2013/0109742 A1 | 5/2013 | Hewitt et al. |
| 2014/0134168 A1 | 5/2014 | Zurawski et al. |
| 2014/0227268 A1 | 8/2014 | Banchereau et al. |
| 2014/0341852 A1 | 11/2014 | Srivastava et al. |
| 2016/0017005 A1 | 1/2016 | Asokan et al. |
| 2016/0369298 A1 | 3/2016 | Marsic et al. |
| 2016/0289275 A1 | 10/2016 | Chiorini et al. |
| 2016/0369299 A1 | 12/2016 | Boye et al. |
| 2018/0015172 A1 | 1/2018 | Muzyczka et al. |
| 2018/0066285 A1 | 3/2018 | Ojala et al. |
| 2018/0193489 A1 | 7/2018 | Hobbs et al. |
| 2018/0244727 A1 | 8/2018 | Zhong et al. |
| 2018/0245098 A1 | 8/2018 | Yazicioglu et al. |
| 2019/0048041 A1 | 2/2019 | Asokan et al. |
| 2019/0127424 A1 | 5/2019 | Srivastava et al. |
| 2019/0249195 A1 | 8/2019 | Marsic et al. |
| 2019/0382452 A1* | 12/2019 | Samulski ............... A61P 3/00 |
| 2020/0002386 A1 | 1/2020 | Zolotukhin et al. |
| 2020/0181644 A1 | 6/2020 | Zolotukhin et al. |
| 2021/0061863 A1 | 3/2021 | Zolotukhin et al. |
| 2021/0290771 A1 | 9/2021 | Muzyczka et al. |
| 2022/0333136 A1 | 10/2022 | Zolotukhin et al. |

FOREIGN PATENT DOCUMENTS

| | | |
|---|---|---|
| JP | 2008-523813 A | 7/2008 |
| JP | 2016-520311 A | 7/2016 |
| JP | 2016-533709 A | 11/2016 |
| WO | WO 2004/112727 A2 | 12/2004 |
| WO | WO 2005/033321 A2 | 4/2005 |
| WO | WO 2007/089632 A2 | 8/2007 |
| WO | WO 2008/124724 A1 | 10/2008 |
| WO | WO 2010/011404 A2 | 1/2010 |
| WO | WO 2010/093784 A2 | 8/2010 |
| WO | WO 2012/057363 A1 | 5/2012 |
| WO | WO 2012/109570 A1 | 8/2012 |
| WO | WO 2013/170078 A1 | 11/2013 |
| WO | WO 2014/193716 A2 | 12/2014 |
| WO | WO 2015/048534 A1 | 4/2015 |
| WO | WO 2015/108610 A1 | 7/2015 |
| WO | WO 2015/121501 A1 | 8/2015 |
| WO | WO 2015/134643 A1 | 9/2015 |
| WO | WO 2017/070476 A2 | 4/2017 |

OTHER PUBLICATIONS

Partial European Search Report dated Dec. 1, 2020 in connection with Application No. EP 18756857.1.

Extended European Search Report for Application No. EP 18756857.1 dated Mar. 12, 2021.

Invitation to Pay Additional Fees for Application No. PCT/US2018/019050 dated May 8, 2018.

International Search Report and Written Opinion for Application No. PCT/US2018/019050 dated Jul. 6, 2018.

International Preliminary Report on Patentability for Application No. PCT/US2018/019050 dated Sep. 6, 2019.

Appleyard et al., Pretreatment with the probiotic VSL#3 delays transition from inflammation to dysplasia in a rat model of colitis-associated cancer. Am J Physiol Gastrointest Liver Physiol. Dec. 2011;301(6):G1004-13. doi: 10.1152/aipgi.00167.2011. Epub Sep. 8, 2011.

Aslanidi et al., High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.

Aslanidi et al., Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.

Aydemir et al., Mutants at the 2-Fold Interface of Adeno-associated Virus Type 2 (AAV2) Structural Proteins Suggest a Role in Viral Transcription for AAV Capsids. J Virol. Jul. 27, 2016;90(16):7196-7204. doi: 10.1128/JVI.00493-16.

Bowles et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.

Bozzetti et al., Metabolic Bone Disease in preterm newborn: an update on nutritional issues. Ital J Pediatr. Jul. 14, 2009;35(1):20. doi: 10.1186/1824-7288-35-20.

Choudhury et al., Novel Methodology for Creating Macaque Retinas with Sortable Photoreceptors and Ganglion Cells. Front Neurosci. Dec. 1, 2016;10:551. eCollection 2016.

Crommentuijin et al., Systemically administered AAV9-sTRAIL combats invasive glioblastoma in a patient-derived orthotopic xenograft model. Mol Ther Oncolytics. Jun. 22, 2016;3:16017. doi: 10.1038/mto.2016.17.

Galindo, Alkaline Phosphatase (ALP). Aug. 23, 2010. Retrieved on May 8, 2018. http://www.isu.edu/~galisusa/alp_sop.html. 4 pages.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., Clades of Adeno-associated viruses are widely disseminated in human tissues. J Virol. Jun. 2004;78(12):6381-8.

Genbank Submission; NIH/NCBI, Accesion No. AAS99272.1. Gao et al., Jun. 24, 2004.

Grimm et al., E Pluribus Unum: 50 Years of Research, Millions of Viruses, and One Goal—Tailored Acceleration of AAV Evolution. Mol Ther. Dec. 2015;23(12):1819-31.

Guhasarkar et al., Systemic AAV9-IFNβ gene delivery treats highly invasive glioblastoma. Neuro Oncol. Nov. 2016;18(11):1508-1518. doi: 10.1093/neuonc/now097. Epub May 18, 2016.

Guo et al., Protein tolerance to random amino acid change. PNAS. Jun. 22, 2004;101(25):9205-10.

Gurda et al., Capsid antibodies to different adeno-associated virus serotypes bind common regions. J Virol. Aug. 2013;87(16):9111-24. doi: 10.1128/JVI.00622-13. Epub Jun. 12, 2013.

Klimczak, Molecular evolution of adeno-associated virus for improved retinal gene therapies. University of California, Berkeley. Jan. 1, 2010. Retrieved from the internet <https://digitalassets.lib.berkeley.edu/etd/ucb/text/Klimczak_berkeley_0028E_10444.pdf> 116 pages.

Koerber et al., DNA shuffling of adeno-associated virus yields functionally diverse viral progeny. Mol Ther. Oct. 2008;16(10):1703-9. doi: 10.1038/mt.2008.167. Epub Aug. 26, 2008. Author Manuscript, 17 pages.

Lan et al., IA-2, a transmembrane protein of the protein tyrosine phosphatase family, is a major autoantigen in insulin-dependent diabetes mellitus. Proc Natl Acad Sci U S A. Jun. 25, 1996;93(13):6367-70.

Lerch et al., The structure of adeno-associated virus serotype 3B (AAV-3B): insights into receptor binding and immune evasion. Virology. Jul. 20, 2010;403(1):26-36. doi: 10.1016/j.virol.2010.03.027. Epub May 4, 2010.

Lochrie et al., Mutations on the external surfaces of adeno-associated virus type 2 capsids that affect transduction and neutralization. J Virol. Jan. 2006;80(2):821-34. doi: 10.1128/JVI.80.2.821-834.2006.

Maersch et al., Optimization of stealth adeno-associated virus vectors by randomization of immunogenic epitopes. Virology. Feb. 5, 2010;397(1):167-75. doi: 10.1016/j.virol.2009.10.021. Epub Nov. 18, 2009.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009. Author Manuscript, 16 pages.

Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.

(56) References Cited

OTHER PUBLICATIONS

Marsic et al., Vector design Tour de Force: integrating combinatorial and rational approaches to derive novel adeno-associated virus variants. Mol Ther. Nov. 2014;22(11):1900-9. doi: 10.1038/mt.2014.139. Epub Jul. 22, 2014.

Méndez-Gómez, et al., Transcytosis in the blood-cerebrospinal fluid barrier of the mouse brain with an engineered receptor/ligand system. Mol Ther Methods Clin Dev. Oct. 7, 2015;2:15037. doi: 10.1038/mtm.2015.37. eCollection 2015.

Muramatsu et al., Nucleotide sequencing and generation of an infectious clone of adeno-associated virus 3. Virology. Jul. 1, 1996;221(1):208-17.

Opie et al., Identification of amino acid residues in the capsid proteins of adeno-associated virus type 2 that contribute to heparan sulfate proteoglycan binding. J Virol. Jun. 2003;77(12):6995-7006.

Ozawa, [Gene therapy using AAV], Uirusu. Jun. 2007;57(1):47-55. Article in Japanese.

Pang et al., AAV-mediated cone rescue in a naturally occurring mouse model of CNGA3-achromatopsia. PLoS One. 2012;7(4):e35250. doi: 10.1371/journal.pone.0035250. Epub Apr. 2012.

Perabo et al., Combinatorial engineering of a gene therapy vector: directed evolution of adeno-associated virus. J Gene Med. Feb. 2006;8(2):155-62.

Romero et al., Exploring protein fitness landscapes by directed evolution. Nat Rev Mol Cell Biol. Dec. 2009;10(12):866-76. Author Manuscript, 25 pages.

Santiago-Ortiz S et al., Adeno-associated virus (AAV) vectors in cancer gene therapy. J Control Release. Oct. 28, 2016;240:287-301. doi: 10.1016/j.jconrel.2016.01.001. Epub Jan. 12, 2016. Author Manuscript, 39 pages.

Shannon et al., ID of Optimal Gene Delivery Vectors in Primate Retina for Treatment of Human Disorders: Labels Non-Human Primate Eyes with Fluorescent Proteins and/or Fluorescent Dyes, Creating Sortable Cell Populations, Allowing for Screening of Capsid and Promoter Libraries. Office of Technology Licensing, University of Florida. Feb. 11, 2017. Retrieved from the Internet: <http://technologylicensing.research.ufl.edu/technologies/16134.pdf> on Apr. 12, 2017. 4 pages.

Talbot et al., Serum Phosphatase as an Aid in the Diagnosis of Cretinism and Juvenile Hypothyroidism. Am J dis Child. 1941;62(2):273-278.

Tseng et al., Mapping the AAV Capsid Host Antibody Response toward the Development of Second Generation Gene Delivery Vectors. Front Immunol. Jan. 30, 2014;5:9. doi: 10.3389/fimmu.2014.00009. eCollection 2014.

Wu et al., Mutational analysis of the adeno-associated virus type 2 (AAV2) capsid gene and construction of AAV2 vectors with altered tropism. J Virol. Sep. 2000;74(18):8635-47. doi: 10.1128/jvi.74.

Xie et al., The atomic structure of adeno-associated virus (AAV-2), a vector for human gene therapy. Proc Natl Acad Sci U S A. Aug. 6, 2002;99(16):10405-10. doi: 10.1073/pnas.162250899. Epub Jul. 22, 2002.

Zhong et al., Next generation of adeno-associated virus 2 vectors: point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.

Zolotukhin et al., Improved Adeno-associated Viral Gene Transfer to Murine Glioma. J Genet Syndr Gene Ther. Apr. 29, 2013;4(133):12815. doi: 10.4172/2157-7412.

Burger et al., Recombinant AAV viral vectors pseudotyped with viral capsids from serotypes 1, 2, and 5 display differential efficiency and cell tropism after delivery to different regions of the central nervous system. Mol Ther. Aug. 2004;10(2):302-17. doi: 10.1016/j.ymthe.2004.05.024.

Kanaan et al., Rationally Engineered AAV Capsids Improve Transduction and Volumetric Spread in the CNS. Mol Ther Nucleic Acids. Sep. 15, 2017;8:184-197. doi: 10.1016/j.omtn.2017.06.011. Epub Jun. 21, 2017.

\* cited by examiner

| | 263 | 325 | 444 | 490 | 527 | 545 | cn | % |
|---|---|---|---|---|---|---|---|---|
| | QSGAS | Q | YLSRTNTPSGTTPQSRIQ | KTSADNNNSEYSWTGATK | KDDEEK | QGSEKTNVDIEK | | |
| Wild-type (SEQ ID NO: 29) | ..... | . | ................ | .................. | ...... | ............ | 9 | 32.1 |
| Variant Va (SEQ ID NO: 11) | NA... | . | ................ | ...DGE......DF.... | ...... | EDATEN.I..DR | 6 | 21.4 |
| Variant Vb (SEQ ID NO: 12) | NA... | . | ................ | ...DGE......DF.... | ...... | .SAAGAD.A.DS | 2 | 7.1 |
| Variant Vc (SEQ ID NO: 13) | ..... | . | ................ | ...DGE......DF.... | ...... | EDATEN.I..DR | 2 | 7.1 |
| Variant Vd (SEQ ID NO: 14) | ..... | . | ................ | ...DGE......DF.... | ...... | .SAAGAD.A.DS | 1 | 3.6 |
| Variant Ve (SEQ ID NO: 15) | ..... | F | ................ | ...DGE......DF.... | ...... | ............ | 1 | 3.6 |
| Variant Vf (SEQ ID NO: 16) | ..... | . | ................ | ...DGE......DF.... | ...... | ............ | 1 | 3.6 |
| Variant Vg (SEQ ID NO: 17) | ..... | F | ................ | ...DGE......DF.... | ...... | ............ | 1 | 3.6 |
| Variant Vh (SEQ ID NO: 18) | NA... | . | ...F..DEA.SE.K.T.R | ...DGE......DF.... | ...... | ............ | 1 | 3.6 |
| Variant Vi (SEQ ID NO: 19) | NA... | . | ................ | ...DGE......DF.... | ...... | .SGREGDAE..D | 1 | 3.6 |
| Variant Vj (SEQ ID NO: 20) | A.... | . | ................ | ...DGE......DF.... | ...... | EDATEN.I..DR | 1 | 3.6 |
| Variant Vk (SEQ ID NO: 21) | A.... | . | ................ | t..DGE......DF.... | ...... | EDATEN.I..DR | 1 | 3.6 |
| Variant Vl (SEQ ID NO: 22) | ....W | . | ....A..NV....... | .................. | R..DD. | ............ | 1 | 3.6 |
| Variant Vm (SEQ ID NO: 23) | ..... | . | ..KF............ | .................. | ...... | EDATEN.I..DR | 1 | 3.6 |

FIG. 3

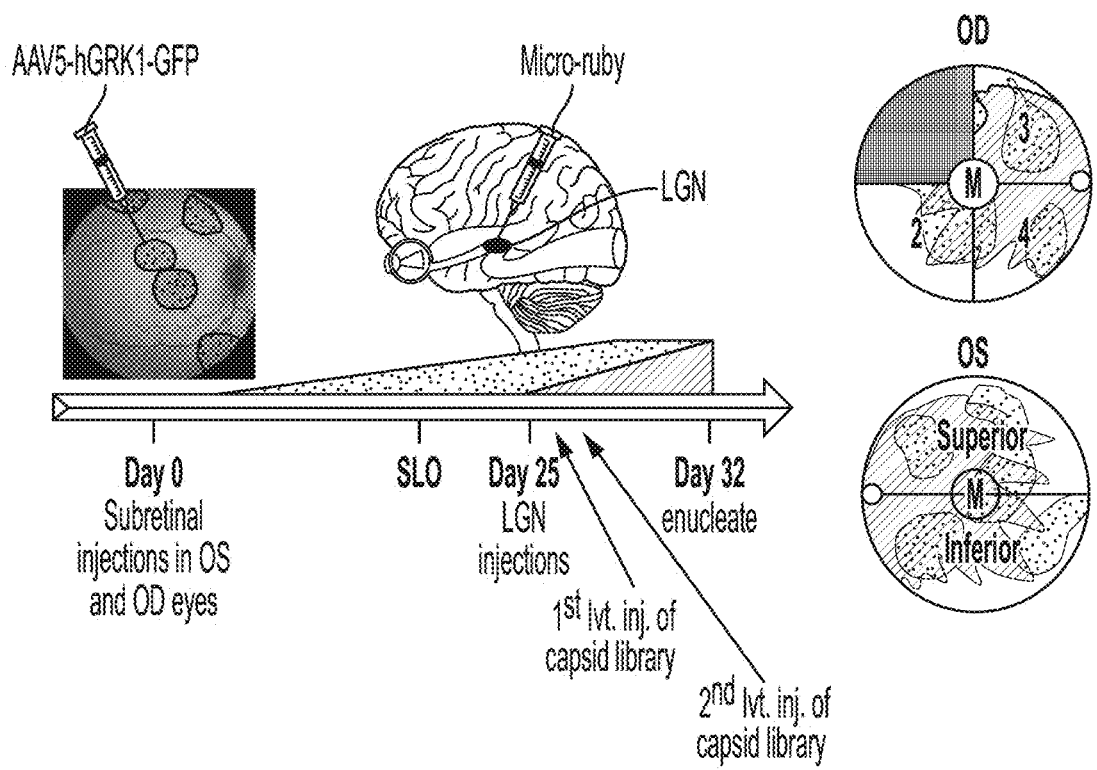
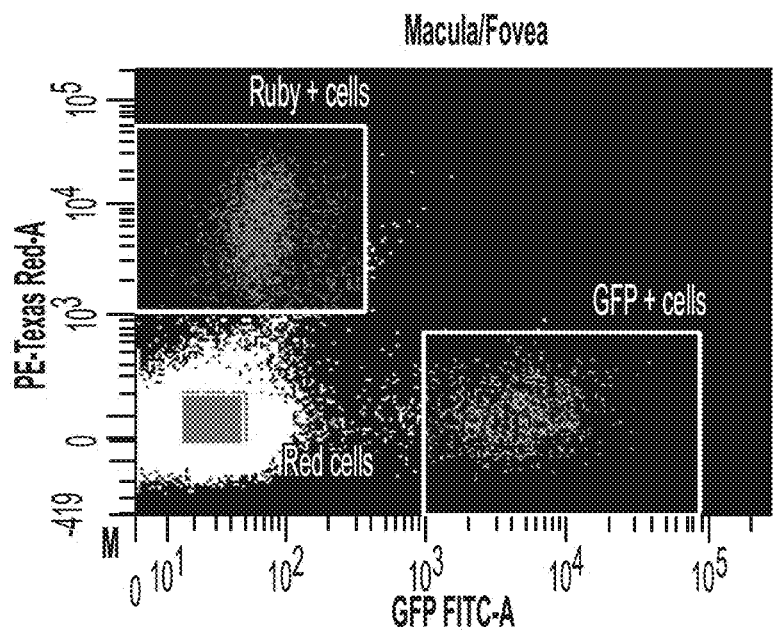
FIG. 4

| | 263 | 444 | 490 | 527 | 545 |
|---|---|---|---|---|---|
| | QSGAS | YLSRTNIPSGTTTQSRLQ | KTSADNNNSEYSWTGATK | KDDEEK | QGSEKTNVDIEK |
| Wild-type (SEQ ID NO: 29) | | | | | |
| Variant V1 (SEQ ID NO: 12) | NA... | ................. | ...DGE......DF........ | ...... | .SAAGAD.A.DS |
| Variant V2 (SEQ ID NO: 24) | A.... | ................. | T.P.........DF........ | ...D.. | ............ |
| Variant V3 (SEQ ID NO: 25) | NA... | F.A..NV....T.. | .................... | R..DD. | ............ |
| Variant V4 (SEQ ID NO: 11) | ..... | ................. | ...DGE......DF........ | ...... | EDATEN.I..DR |
| Variant V5 (SEQ ID NO: 26) | ..... | ................. | ..QD.E....F..P........ | ...D.. | ............ |
| Variant V6 (SEQ ID NO: 27) | ..... | ................. | .V.........F.......... | ...... | ............ |
| Variant V7 (SEQ ID NO: 28) | EA... | ................. | .................... | ...... | ..AAADD.E.DG |

FIG. 5

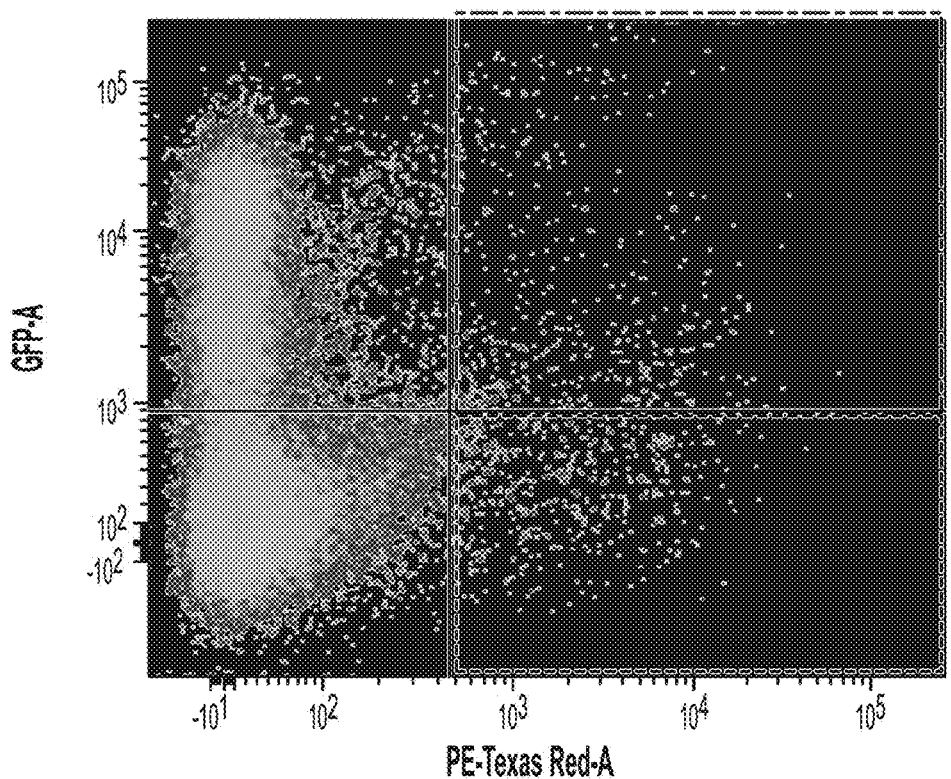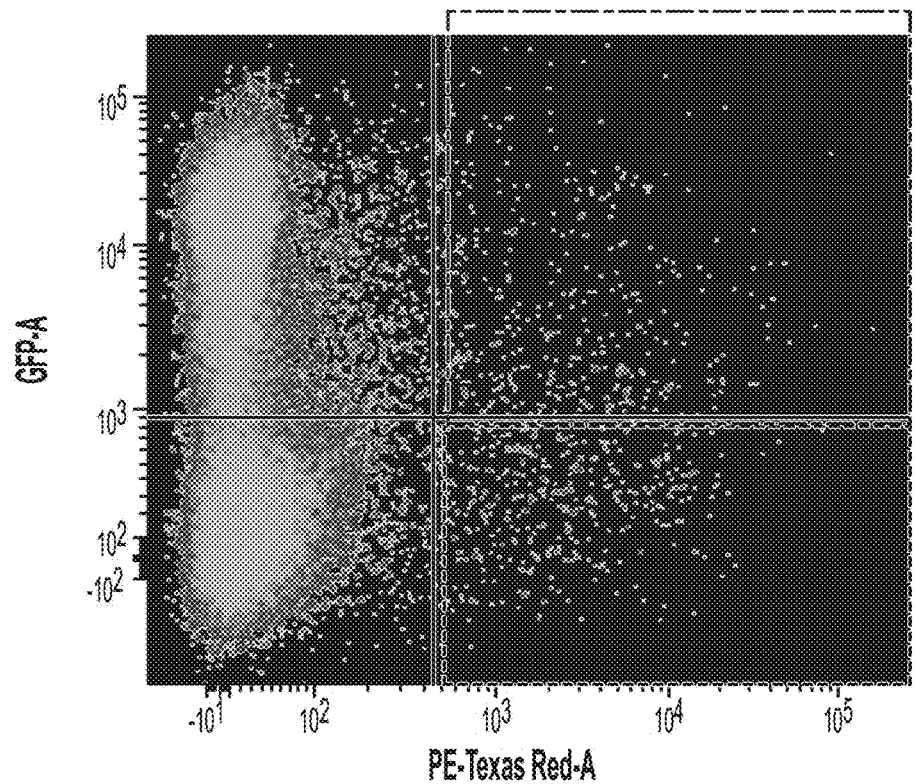
FIG. 6B

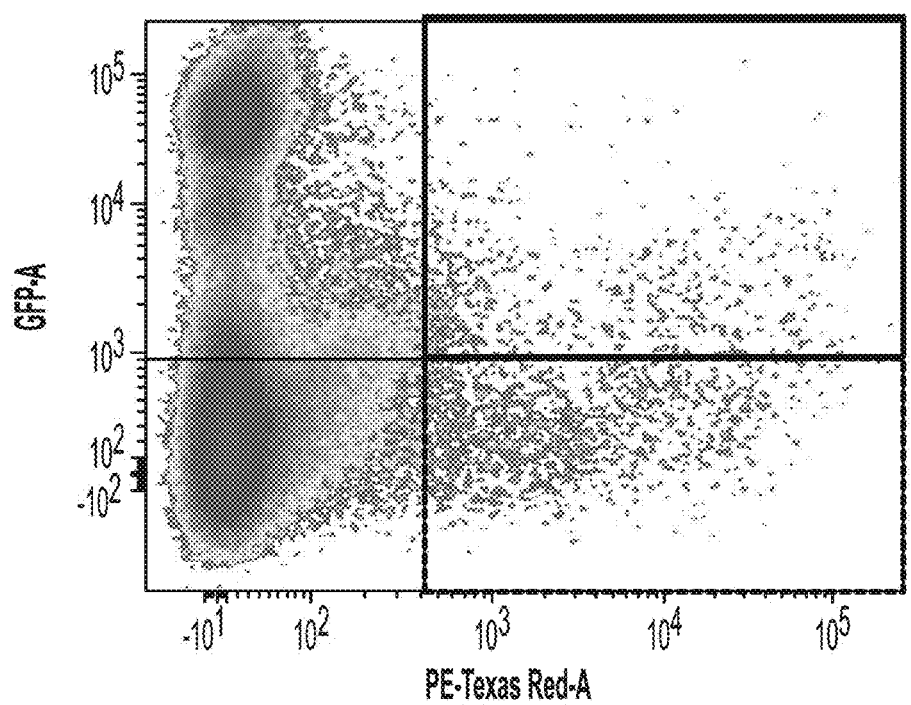
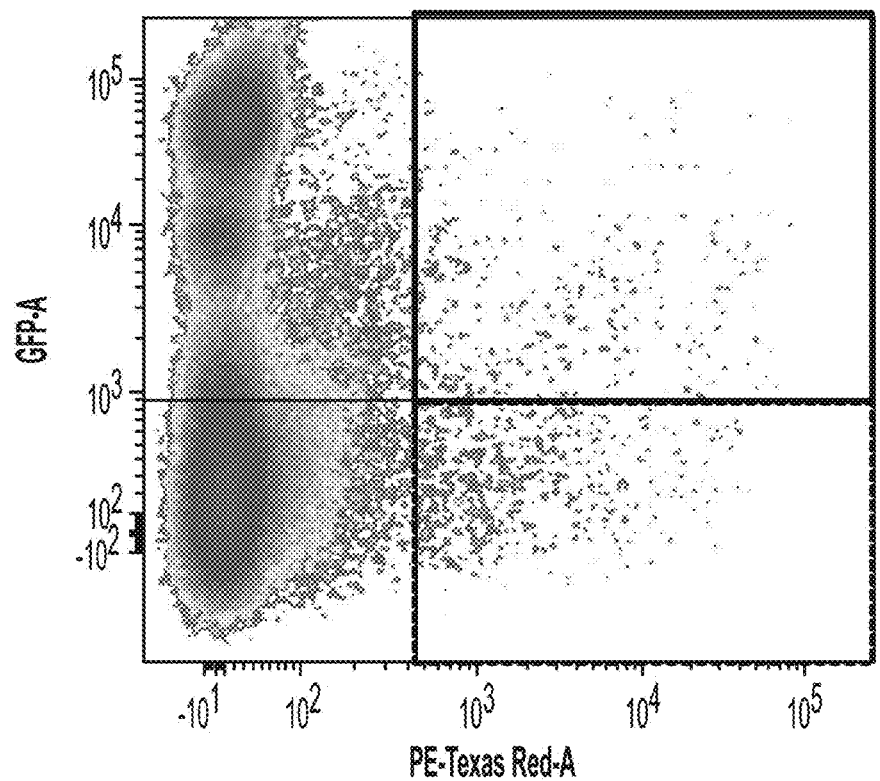
FIG. 10B

| sTiter: 2E+12 | Inner Retina | Outer Retina |
|---|---|---|
| Va | 3% | 2.9% |
| Vb | 5.9% | 5.8% |
| Va-YF | 1.9% | 6% |
| Vb-YF | 11.3% | 17.3% |
| Vb-YF+T-V | 11.1% | 20.8% |
| AAV2QY-F+T-V | 3.6% | 4.6% |

| | Variable loop (position rel. AAV2) | VR-I (263-265) | VR-IV (450-466) | VR-V (490-503) | VR-VI (527-532) | VR-VII (545-556) | VR-VIII* (585-596) |
|---|---|---|---|---|---|---|---|
| Capsid Variants | Vb | 2 | --- | 5 | --- | 9 | --- |
| | V2 | 1 | --- | 4 | 1 | --- | --- |
| | V3 | 2 | 5 | --- | 3 | --- | --- |
| | Va | --- | --- | 5 | --- | 9 | --- |
| | V5 | --- | --- | --- | 1 | --- | --- |
| | V6 | --- | --- | 5 | --- | --- | --- |
| | V7 | 2 | --- | 2 | --- | 8 | --- |

| | 263 | 444 | 490 | 527 | 545 | 585 | %PR3 | %RG3 | Names |
|---|---|---|---|---|---|---|---|---|---|
| | QSGAS | YLSRTNTPSGTTTQSRLQ | KTSADNNNSEYSWTGATK | KDDEEK | QGSEKTNVDIEK | RGNRQAATADVN | | | |
| | XX... | .................. | .................. | ...... | ............ | ............ | 0.7 | 13.9 | P3-RGC1 |
| | XX...F. | .....SD..ID..N.M..A. | .....DE........... | ...DG. | ............ | ............ | 0.0 | 2.2 | P3-RGC2 |
| | XX.X F... | ....D...S..M.T.R..V. | .....F........... | ...D.. | ............ | ............ | 0.0 | 1.2 | P3-RGC3 |
| | NA.... | .................. | ..DGE........DF... | ...... | ............E | ............ | 3.5 | 0.0 | P3-PR1 |
| | DA..T F. | ....A..M.K.H..YN... | .....F......T..... | ...D.R | ............ | ............ | 2.0 | 0.0 | P3-PR2 |
| | .....F. | ..GA.NM.T.A.R.T.P.. | .....DF.......... | ...D.. | ............ | ............ | 1.2 | 0.0 | P3-PR3 |
| | XX.... | .................. | .....V........F... | ...... | ............ | ..AAADD.E.DG | 3.5 | 1.0 | -V7 |
| | XX.... | .................. | .................. | ...D.. | ............ | ..AGRADI...S | 0.1 | 0.7 | P3-RGC4 |
| | XX..X. | .................. | .QD.E.......F..P.. | ...... | ............ | ..SAAGAD.A.DS | 0.0 | 0.7 | P3-RGC5 |

Round 3 NHP screen top variants

```
     263   444                                                       585
     QSGAS YLSRTNTPSGTTQSRLQ KTSADNINSEYSWTGATK KDDEEK QGSEKTNVDIEK RGNRQAATADVN  Names
     .....  F....A..NV...T..  ................  R..DD. ............ ............  V3
     NA... .................  .DGE........DF...  ...... .SAAGAD.A.DS ............  V1, Vb
     A.... .................  T.P.........DF...  ...... .SAAGAD.A.DS ............  V2
     ..... .................  ............E....  ...... ............ ............  P3-1
     ..... .F...A..NV...T..   ............F.P..T ...... ............ ............  V3 variant
     NA... .................  ............DF...  R..DD. ............ ............  P3-2
     A.... .F...A..NV...T..   ............DF...  R..DD. ............ ............  P3-3
     ..... .................  .DGE........DF...  ...... .SAAGAD.A.DS ............  Vd
     ..... .................  ............DF...  ...DD. EDATEN.I..DR ............  V4, Va
     NA... .................  .DGE........DF...  ...... .SAAGAD.A.DS ............  P3-4
     A.... .................  .DGE........DF...  ...... ............ ............  P3-5
     A.... .................  .DGE........DF...  ...... .SAAGAD.A.DS ............  P3-6
     NA... .................  ............F....  ..TR.. D.R.......... ............  P3-7
     GT... .................  ............F.P..  ...... ............ ............  P3-8
```

Variants of interest based on differential enrichment between PRs and RGCs in round 3 NHP screen

```
     263   444                                                       585
     QSGAS YLSRTNTPSGTTQSRLQ KTSADNINSEYSWTGATK KDDEEK QGSEKTNVDIEK RGNRQAATADVN  %PR3  %RG3  Names
     XX... .................  .QD.E....F..P....  ...... ............ ............   0.7  13.9  P3-RGC1
     XX... .F...............  ............F.P..  .T.... ............ ............   4.9   4.7  P3-V14
     NA... .................  .DGE........DF...  ...... E........... ............   3.5   0.0  P3-PR1
     XX... .F..SD..ID...N.M.  A............F...  .DG... ............ ............   0.0   2.2  P3-RGC2
     DA..T .F....A..M.K.H...  YN...........F...  ..D.R. ............ ............   0.0   0.0  P3-PR2
     ..... .GA.NM.T.A.R.T.P.  .............F...  ..D.R. ............ ............   2.0   0.0  P3-PR3
     XX..X .F...D..S..MT.R..  V............F...  ...D.. .........S... ............   1.2   0.0  P3-RGC3
     XX... .................  .............F...  ...... ..AGRADI...S ............   0.0   1.2  P3-RGC4
     XX... .................  .............F...  ...... .SAAGAD.A.DS ............   0.1   0.7  P3-RGC5
     XX... X................  .QD.E....F..P....  ...... ............ ............   0.0   0.7  
```

MODIFIED AAV CAPSID PROTEINS AND USES THEREOF

RELATED APPLICATIONS

This application is a continuation of U.S. application Ser. No. 17/009,536, filed on Sep. 1, 2020, which is a continuation of U.S. application Ser. No. 16/547,532, filed on Aug. 21, 2019, which is a continuation of PCT Application No. PCT/US2018/019050, filed Feb. 21, 2018, which claims priority to U.S. Provisional Application No. 62/461,770, filed on Feb. 21, 2017, and U.S. Provisional Application No. 62/625,486, filed on Feb. 2, 2018, the entire disclosures of each of which are incorporated by reference in their entireties.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Feb. 14, 2023, is named U119670051US03-SUBSEQ-PRW and is 122,108 bytes in size.

GOVERNMENT SUPPORT

This invention was made with government support under RO1 EY024280 and RO1 HL097088, awarded by the National Institutes of Health. The government has certain rights in the invention.

BACKGROUND

Adeno associated viral (AAV) particles are emerging as a useful vehicle for gene delivery. While different AAV serotypes have particular organ tropism that can be taken advantage of to target gene-based therapies to a target organ (see e.g., Surace et al., Vision Res. 2008, 48(3):353-9; Zincarelli et al., Mol Ther. 2008,16(6):1073-80), the increased efficiency in AAV for targeting certain organs or tissues would be of great benefit. An example of such tissue is the retina.

SUMMARY

The organ or tissue tropism of AAV particles depends highly, if not entirely, on the make-up of the particle surface, or the capsid. AAV serotype 2 (AAV2) has a tropism for and is used to deliver genes to the retina (see e.g., Vandenberghe et al., Gene Ther. 2012, 19(2):162-8). The AAV2 capsid is made up of three proteins, VP1, VP2 and VP3. Provided herein are compositions and methods for variant (e.g., modified) AAV (e.g., AAV2) capsid proteins and particles that have an improved efficiency to transduce retinal cells (e.g., photoreceptors, retinal ganglion cells and retinal neural cells). This disclosure is based, at least in part, on the identification of AAV2 (AAV2) variant proteins (e.g., modified AAV2 capsid proteins) and recombinant particles comprising the modified capsid proteins that have a greater efficiency to transduce retinal cells compared to rAAV2 particles comprising wild-type capsid proteins, using in vivo screening of a AAV2 capsid library containing capsid variants with amino acid substitutions or mutations in the capsid proteins of AAV2 in a mouse model and a macaque model.

In some embodiments, provided herein are variant (e.g., modified) recombinant adeno-associated virus (rAAV) serotype 2 (AAV2) capsid proteins comprising sequences DGE and/or DF in variable region (VR) V (VRV), and any one or more of the following sets of sequences and/or substitutions:

(a) EDATENXIXXDR (as set forth in SEQ ID NO: 4) in VRVII,
(b) NA in VRI; and SAAGADXAXDS (as set forth in SEQ ID NO: 5) in VRVII,
(c) NA in VRI; and EDATENXIXXDR (as set forth in SEQ ID NO: 4) in VRVII,
(d) SAAGADXAXDS (as set forth in SEQ ID NO: 5) substitution in VRVII,
(e) NA in VRI; and SAAGADXAXDS (as set forth in SEQ ID NO: 5) in VRVII,
(f) a Q to A substitution in loop I; and EDATENXIXXDR (as set forth in SEQ ID NO: 4) in VRVII,
(g) a Q to A substitution in loop I; a K to T substitution in VRV; and EDATENXIXXDR (as set forth in SEQ ID NO: 4) in VRVII, and
(h) a S to W substitution at position 267; and EDATENXIXXDR (as set forth in SEQ ID NO: 4) in VRVII. X may be any amino acid (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan or valine).

In some embodiments, provided herein is a variant (e.g., modified) recombinant AAV2 capsid protein comprising sequences DGE and/or DF in VRV. In some embodiments, provided herein is a variant recombinant AAV2 capsid protein comprising sequences DGE and/or DF in VRV, and NA in VRI.

In some embodiments, provided herein is a variant (e.g., modified) recombinant AAV2 capsid protein comprising any one of the following sets of sequences and/or substitutions:

(a''') NA in VRI; a F at position 444; and DEAXSEXKXTXR (as set forth in SEQ ID NO: 7) in VRIV,
(b''') Q325K in VRII; Y444F; S452A, T454N and T455V in VRIV; and RXXDD (as set forth in SEQ ID NO: 8) in VRVI,
(c''') Q263A in VRI; K490T, S492P, E499D and Y500F in VRV; and E530D in VRVI,
(d''') NA in VRI; Y444F; P451A, T454N, T455V and R459T in VRIV; and RXXDD (as set forth in SEQ ID NO: 8) in VRVI,
(e''') E530D in VRVI,
(f''') QDXE (as set forth in SEQ ID NO: 9), and substitutions Y500F and T503P in VRV, and
(g''') EA in VRI; T491V and Y500F in VRV; and AAADDXEXDG (as set forth in SEQ ID NO: 10) in VRVII. X may be any amino acid (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan or valine).

In some embodiments, amino acids denoted by X are amino acids in wild-type AAV2 sequence as set forth in SEQ ID NO: 1. For example, sequence EDATENXIXXDR, as set forth in SEQ ID NO: 4, is homologous to amino acids 545 to 556 in VRVII of wild-type AAV2 VP1 protein as set forth in SEQ ID NO: 1. Therefore, in some embodiments, sequence EDATENXIXXDR may be sequence EDATENNIDIDR. Similarly, in some embodiments, sequence RXXDD (SEQ ID NO: 8) is sequence RDDDD.

In some embodiments, a variant rAAV2 capsid protein comprises the sequences DGE and/or DF in VRV, and sequence EDATENXIXXDR (as set forth in SEQ ID NO: 4) in VRVII. In some embodiments, a variant rAAV2 capsid protein comprises the sequences DGE and/or DF in VRV, and NA in VRI; and SAAGADXAXDS (as set forth in SEQ ID NO: 5) in VRVII.

This disclosure is also partly based on further improvement of the performance of rAAV2 capsid variants having greater than wild-type efficiency to transduce retinal cells by introducing more amino acid substitutions based on rational capsid design. Accordingly, also provided herein, in some embodiments, are variant rAAV2 capsid proteins further comprising amino acid substitutions that are rationally designed. Any one of the variant rAAV2 capsid protein disclosed herein may further comprise substitution Y444F. In some embodiments, a variant rAAV2 capsid protein comprises sequences DGE and/or DF in VRV, any one of the sequences and/or substitutions in sets (a''') to (c''') and (e''') to (h''') as described above, and substitution Y444F. In some embodiments, any one of the variant rAAV2 capsid protein disclosed herein may further comprise substitution Y730F. In some embodiments, a variant (e.g., modified) recombinant AAV2 capsid protein comprising sequences DGE and/or DF in VRV further comprise one or more of the following substitutions: Y252F, Y272F, Y444F, Y700F, Y704F, Y730F and T491V. In some embodiments, a variant (e.g., modified) recombinant AAV2 capsid protein comprising sequences DGE and/or DF in VRV and NA in VRI further comprise one or more of the following substitutions: Y252F, Y272F, Y444F, Y700F, Y704F, Y730F and T491V. In some embodiments, any one of the variant rAAV2 capsid proteins disclosed herein further comprises the substitutions Y272F, Y444F, Y730F and T491V.

Any one of the variant (e.g., modified) rAAV2 capsid proteins disclosed herein may further comprise substitution Y252F. Any one of the modified rAAV2 capsid proteins disclosed herein may further comprise substitution Y272F. Any one of the variant rAAV2 capsid protein disclosed herein may further comprise substitution Y500F. Any one of the variant rAAV2 capsid protein disclosed herein may further comprise substitution Y700F. Any one of the variant rAAV2 capsid protein disclosed herein may further comprise substitution Y704F. In some embodiments, any one of the variant rAAV2 capsid protein disclosed herein may further comprise substitution T491V, if a valine does not exist at that position already. In some embodiments, a variant rAAV2 capsid protein comprises any one of the sets (a'''), (b'''), (c''') and (e''') of sequences and/or substitutions as described above, and further comprises the substitution Y500F.

In some embodiments any one the modified capsids disclosed herein may contain insertions of 6 to 8 amino acids at positions 587 or 588 of VP1, VP2 and VP3.

In some embodiments, a modified AAV2 capsid protein is a VP3 protein. In some embodiments, a modified AAV2 capsid protein is a VP2 protein. In some embodiments, a modified AAV2 capsid protein is a VP1 protein.

In some aspects, provided herein are rAAV particles that comprise any of the modified AAV2 capsid proteins disclosed herein. In some embodiments, a variant rAAV2 particle comprises a nucleic acid comprising inverted terminal repeats (ITRs). In some embodiments of any one of the variant rAAV2 particles disclosed herein comprises a nucleic acid comprising a gene of interest.

In some embodiments, a nucleic acid comprised in a variant rAAV2 particle is single-stranded. In some embodiments, a nucleic acid comprised in a variant rAAV2 particle is double-stranded.

In some aspects, provided herein is a composition comprising a plurality of any one of the variant rAAV2 particles disclosed herein. In some embodiments, a composition of rAAV particles further comprises a pharmaceutically acceptable carrier.

In some aspects, provided here are also methods of using any one of the particles disclosed herein to transduce retinal cells with a gene. In some embodiments, a method of transducing a photoreceptor cell and/or retinal ganglion cell with a gene of interest comprises providing to the photoreceptor cell any one of the compositions disclosed herein. In some embodiments, AAV2 particles provided to the photoreceptor cells and/or retinal ganglion cells comprise the gene of interest. In some embodiments, a composition is provided to the photoreceptor cell and/or retinal ganglion cell via an intravitreal injection to the subject carrying the photoreceptor and/or retinal ganglion cell. In some embodiments, a composition is provided to the photoreceptor cell and/or retinal ganglion cell via a subretinal injection to the subject carrying the photoreceptor cell and/or retinal ganglion cell. In some embodiments a composition is provided to the photoreceptor cell and/or retinal ganglion cell via a subILM injection to the subject carrying the photoreceptor cell and/or retinal ganglion cell (see e.g., Hum Gene Ther. 2016 August; 27(8):580-97).

Provided herein is also a method of transducing an ependymal cell or a Purkinje cell with a gene of interest. In some embodiments, the method comprises providing to the ependymal cell or the Purkinje cell a composition comprising a plurality of recombinant AAV2 particles comprising a variant recombinant AAV2 capsid protein, wherein the capsid protein comprises the sequences DGE and/or DF in VRV, and NA in VRI; and SAAGADXAXDS (as set forth in SEQ ID NO: 5) in VRVII. In some embodiments, a composition is provided to the ependymal cell or the Purkinje cell via an intraventricular injection to the subject carrying the ependymal cell or the Purkinje cell.

In some embodiments, a subject is a mammal. In some embodiments, a mammal is a human. In some embodiments, a gene of interest encodes a therapeutic protein. A therapeutic protein may be an antibody or antibody fragment, a peptibody, a growth factor, a hormone, a membrane protein, a cytokine, a chemokine, an activating or inhibitory peptide acting on cell surface receptors or ion channels, a cell-permeant peptide targeting intracellular processes, an enzyme, a nuclease or other protein used for gene editing. In some embodiments a gene of interest encodes an RNA, such as a ribozyme RNA, shRNA, or miRNA for regulating gene expression, or a guide RNA for gene editing.

In some embodiments, provided herein are variant (e.g., modified) recombinant adeno-associated virus (rAAV) serotype 2 (AAV2) capsid proteins comprising (a') XX in variable region I (VRI); QDXE in variable region V (VRV); Y500F; and T503P, (b') XX in VRI; Y444F; SD, ID, and/or NXM in variable region IV (VRIV); S492A; DF in VRV; and DG in variable region VI (VRVI), (c') XX and/or X in VRI; Y444F; T450D; T454S; MXTXR in VRIV; T491V; Y500F; and E531D, (d') NA in VRI; DGE and DF in variable VRV; and Q545E, (e') DAXXT in VRI; Y444F; AXMXKXH (SEQ ID NO: 30) in VRIV; YN in VRV; Y500F; K507T; and DXR in VRIV, (f') Y444F; GAXNMXTXAXR (SEQ ID NO: 31) in VRIV; TXP and DF in VRV; and E530D, (g') XX in VRI; T491V; Y500F; and AAADDXEXDG (SEQ ID NO: 10) in variable region VII (VRVII), (h') XX in VRI; E530D; and AGRADIXXXS (SEQ ID NO: 33) in VRVII, or (i') XX and/or X in VRI; QDXE in VRV; Y500F; T503P; and SAAGADXAXDS (SEQ ID NO: 5) in VRVII, wherein X may be any amino acid (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan or valine). In some embodiments, any one or more Xs (e.g., all Xs) are wild-type amino acid(s) present in the corresponding position(s) in a wild-type AAV2 capsid protein.

In some embodiments, the variant (e.g., modified) recombinant AAV2 capsid protein comprises: (a") QS, NA, EA, DA, AS, AA, DT, NS, GA, GS, RS, TA, TS, ES, GT, QA, or TT in VRI; QDXE in VRV; Y500F; and T503P, (b") QS, NT, ES, GS, NA, AS, AA, GA or DS in VRI; Y444F; SD, ID, and/or NXM in VRIV; S492A; DF in VRV; and DG in VRVI, (c") QSGAS (SEQ ID NO: 46), NAGAS (SEQ ID NO: 47), TTGAT (SEQ ID NO: 48), EAGAS (SEQ ID NO: 49), TTGAS (SEQ ID NO: 50) or GAGAS (SEQ ID NO: 51) in VRI, (d") QS, EA, QA, NA, AS or ES in VRI; T491V; Y500F; and AAADDXEXDG (SEQ ID NO: 10) in VRVII, (e") QS, DS, NA, AS, DA or AT in VRI; E530D; and AGRADIXXXS (SEQ ID NO: 33) in VRVII, or (f") QSGAS (SEQ ID NO: 46), NAGAS (SEQ ID NO: 47), ASGAS (SEQ ID NO: 52), GAGAS (SEQ ID NO: 51), TAGAS (SEQ ID NO: 53), QTGAS (SEQ ID NO: 54) or TTGAS (SEQ ID NO: 50) in VRI; QDXE in VRV; Y500F; T503P; and SAAGADXAXDS (SEQ ID NO: 5) in VRVII.

This disclosure is also partly based on further improvement of the performance of rAAV2 capsid variants having greater than wild-type efficiency to transduce retinal cells by introducing more amino acid substitutions based on rational capsid design. Accordingly, also provided herein, in some embodiments, are variant rAAV2 capsid proteins further comprising amino acid substitutions that are rationally designed. Any one of the variant rAAV2 capsid protein disclosed herein may further comprise substitution Y444F. In some embodiments, a variant rAAV2 capsid protein comprises any one of the sequences and/or substitutions in sets (a') to (i') or (a") to (f") as described above, and substitution Y444F. In some embodiments, any one of the variant rAAV2 capsid protein disclosed herein may further comprise substitution Y730F. In some embodiments, a variant rAAV2 capsid protein comprises any one of the sequences and/or substitutions in sets (a') to (i') or (a") to (f") as described above, and substitution Y730F. In some embodiments, any one of the variant rAAV2 capsid protein disclosed herein may further comprise substitution Y272F. In some embodiments, a variant rAAV2 capsid protein comprises any one of the sequences and/or substitutions in sets (a') to (i') or (a") to (f") as described above, and substitution Y272F. In some embodiments, any one of the variant rAAV2 capsid protein disclosed herein may further comprise substitution T491V, if a valine does not exist that position already. In some embodiments, a variant rAAV2 capsid protein comprises any one of the sequences and/or substitutions in sets (a') to (i') or (a") to (f") as described above, and substitution T491V. In some embodiments, any one of the variant rAAV2 capsid protein disclosed herein may further comprise substitution Y500F. In some embodiments, a variant rAAV2 capsid protein comprises any one of the sets (a') to (i') or (a") to (f") of sequences and/or substitutions as described above, and further comprises the substitution Y500F.

In some embodiments, a variant rAAV2 capsid protein is a VP3 protein. In some embodiments, a variant rAAV2 capsid protein is a VP2 protein. In some embodiments, a variant rAAV2 capsid protein is a VP1 protein.

In some aspects, provided herein are rAAV particles that comprise any of the variant rAAV2 capsid proteins disclosed herein. In some embodiments, a variant rAAV2 particle comprises a nucleic acid comprising inverted terminal repeats (ITRs). In some embodiments of any one of the variant rAAV2 particles disclosed herein comprises a nucleic acid comprising a gene of interest.

In some embodiments, a nucleic acid comprised in a variant rAAV2 particle is single-stranded. In some embodiments, a nucleic acid comprised in a variant rAAV2 particle is double-stranded. In some embodiments, a nucleic acid comprised in a variant rAAV2 particle is a self-complementary rAAV genome (e.g., an scAAV2 genome).

In some aspects, provided herein is a composition comprising a plurality of any one of the variant rAAV2 particles disclosed herein. In some embodiments, a compositions of rAAV particles further comprises a pharmaceutically acceptable carrier.

In some aspects, provided here are also methods of using any one of the particles disclosed herein to transduce retinal cells with a gene, e.g., a gene of interest. In some embodiments, a method of transducing a photoreceptor cell and/or retinal ganglion cell with a gene of interest comprises providing to the photoreceptor cell any one of the compositions disclosed herein. In some embodiments, AAV2 particles provided to the photoreceptor cells and/or retinal ganglion cells comprise the gene of interest. In some embodiments, a composition is provided to the photoreceptor cell and/or retinal ganglion cell via an intravitreal injection to the subject carrying the photoreceptor and/or retinal ganglion cell. In some embodiments, a composition is provided to the photoreceptor cell and/or retinal ganglion cell via a subretinal injection to the subject carrying the photoreceptor cell and/or retinal ganglion cell.

In some embodiments, a subject is a mammal. In some embodiments, a mammal is a human. In some embodiments, a gene of interest encodes a therapeutic protein. A therapeutic protein may be, e.g., an antibody or antibody fragment, a peptibody, a growth factor, a hormone, a membrane protein, a cytokine, a chemokine, an activating or inhibitory peptide acting on cell surface receptors or ion channels, a cell-permeant peptide targeting intracellular processes, an enzyme, a nuclease or other protein used for gene editing.

Certain peptide sequences inserted at the heparin binding domain of AAV (e.g., AAV2) are known to enhance transduction efficiency. See e.g., Körbelin et al. (EMBO Mol Med. 2016 Jun. 1; 8(6):609-25), Michelfelder et al. (PLoS One. 2009; 4(4): e5122. doi: 10.1371/journal-.pone.0005122), and Körbelin et al. (Mol Ther. 2016 June; 24(6):1050-1061. doi: 10.1038/mt.2016.62). Accordingly, in some embodiments any one the variant capsids disclosed herein may contain insertions of 6 to 8 amino acids at positions 587 or 588 of VP1, VP2 and VP3. In some embodiments, any one of the variant rAAV (e.g., variant rAAV2) capsid protein disclosed here further comprises a peptide. In some embodiments, a peptide may be any one of the peptides disclosed in Körbelin et al. (EMBO Mol Med. 2016 Jun. 1; 8(6):609-25), Michelfelder et al. (PLoS One. 2009; 4(4): e5122. doi: 10.1371/journal.pone.0005122), and Körbelin et al. (Mol Ther. 2016 June; 24(6):1050-1061. doi: 10.1038/mt.2016.62). In some embodiments, any one of the variant rAAV (e.g., variant rAAV2) capsid protein disclosed here further comprises one or more of any one of the following peptides: LALGETTRPA (SEQ ID NO: 66), NRGTEWD (SEQ ID NO: 67), ADGVQWT (SEQ ID NO: 68), GEARISA (SEQ ID NO: 69), SGNSGAA (SEQ ID NO: 70), ESGLSQS (SEQ ID NO: 71), EYRDSSG (SEQ ID NO: 72), DLGSARA (SEQ ID NO: 73), PRSADLA (SEQ ID NO: 74), PRSTSDP (SEQ ID NO: 75), and ESGHGYF (SEQ ID NO: 76). In some embodiments of any one of the variant rAAV (e.g., variant rAAV2) capsid proteins disclosed herein, a peptide is inserted between amino acid positions 587 and 588. In some embodiments of any one of the variant rAAV (e.g., variant rAAV2) capsid proteins disclosed herein, one or more of LALGETTRPA (SEQ ID NO: 66), NRGTEWD (SEQ ID NO: 67), ADGVQWT (SEQ ID NO: 68), GEARISA (SEQ ID NO: 69), SGNSGAA (SEQ ID NO: 70), ESGLSQS (SEQ ID NO: 71), EYRDSSG (SEQ ID NO: 72), DLGSARA (SEQ ID NO: 73), PRSADLA (SEQ ID NO: 74), PRSTSDP (SEQ ID NO: 75), and ESGHGYF (SEQ ID NO: 76) lies between amino acids 585 and 588. In some embodiments of any one of the variant rAAV (e.g., variant rAAV2) capsid proteins disclosed herein, one or more of LALGETTRPA (SEQ ID NO: 66), NRGTEWD (SEQ ID NO: 67), ADGVQWT (SEQ ID NO: 68), GEARISA (SEQ ID NO: 69), SGNSGAA (SEQ ID NO: 70), ESGLSQS (SEQ ID NO: 71), EYRDSSG (SEQ ID NO: 72), DLGSARA (SEQ ID NO: 73), PRSADLA (SEQ ID NO: 74), PRSTSDP (SEQ ID NO: 75), and ESGHGYF (SEQ ID NO: 76) lies between amino acids 587 and 588.

In some embodiments, any one of the variant recombinant AAV2 capsid proteins disclosed herein further comprises one or more of any one of the following substitutions: Y252F, Y272F, Y444F, Y700F, Y704F, Y730F and T491V, or any combination thereof (e.g., any combination of 2, 3, 4, 5, or 6 thereof, or all 7 thereof).

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1A shows the structure of wild-type AAV2 protein with variable loops. FIG. 1B shows the structure of wild-type AAV2 capsid. FIGS. 1C-1E depict the CAPLIB-7 capsid library, which shows input plasmid and capsid diversity.

FIG. 3 shows results after 3 rounds of screening in Nrl-GFP mice following intravitreal injections of AAV capsid library. Variants are shown in order of prevalence, the top-most being the most prevalent.

FIG. 4 shows how the CAPLIB-7 AAV2 capsid library was screened in non-human primate (NHP) for transducing retinal cells, specifically photoreceptor cells (PRs) and retinal ganglion cells (RGCs). Sortable cell populations were created in primate retina including photoreceptors (PR) via subretinal injection of AAV5-GRK1-GFP and retinal ganglion cells (RGC) by direct injection of TRITC-Dextran-Biotin into the lateral geniculate nucleus (LGN) and retrograde transport. The capsid library was delivered during the in-life phase by intravitreal (Ivt) injection.

FIG. 5 shows the most prevalent AAV2 variants identified from the primate screening.

FIGS. 6A-6C. FIG. 6A shows fundus images captured 3 weeks post-intravitreal injection of Sc-smCBA-mCherry carrying AAV2 variant Va particles in Nrl-GFP mice. FIG. 6B shows representative fluorescent activated cell sorting (FACS) scatterplots of retinal cells from Nrl-GFP mice intravitreally injected with AAV2(QuadYF+T–V) or AAV2-Va. FIG. 6C shows the quantification of transduction rates in Nrl-GFP mice as determined by FACS. Values are the average of 6 eyes per vector. Black bars represent rod photoreceptors and grey bars represent non rod, neural retinal cells.

FIG. 7A shows expression of mCherry in sections containing ependymal cells. FIG. 7B shows expression of mCherry in sections containing Purkinje cells.

FIG. 8A shows fundus images captured 3 weeks post-intravitreal injection of Sc-smCBA-mCherry carrying AAV2 variant Vb particles in Nrl-GFP mice. FIG. 8B shows representative fluorescent activated cell sorting (FACS) scatterplots of retinal cells from Nrl-GFP mice intravitreally injected with AAV2(QuadYF+T–V) or AAV2-Vb. FIG. 8C shows the quantification of transduction rates in Nrl-GFP mice as determined by FACS. Values are the average of 6 eyes per vector. Black bars represent rod photoreceptors and grey bars represent non rod, neural retinal cells.

FIGS. 10A-10C show transduction efficiency for AAV2 variant V2. FIG. 10A shows mCherry fluorescence in mouse retinas as observed using funduscopy. FIG. 10B shows representative FACS scatterplots of Nrl-GFP mice intravitreally injected with AAV2-V2 or AAV2(QuadYF+T–V). The mice were sacrificed 4 weeks post injection. FIG. 10C shows transduction efficiency relative to AAV2(quadY-F+T–V). Mice were sacrificed at 4 weeks post injection with 1.2e12 vg/ml of Sc-smCBA-mCherry. Values are the average of 6 eyes per vector.

FIG. 12A shows mCherry fluorescence in mouse retinas as observed using funduscopy. FIG. 12B shows representative FACS scatterplots of Nrl-GFP mice intravitreally injected with AAV2-V3 or AAV2(QuadYF+T–V). The mice were sacrificed 4 weeks post injection. FIG. 12C shows transduction efficiency relative to AAV2(quadY-F+T–V). Mice were sacrificed at 4 weeks post injection with 1.2e12 vg/ml of Sc-smCBA-mCherry. Values are the average of 6 eyes per vector.

FIG. 24 shows round three of screening results. Sequences corresponding to SEQ ID NOs: 45, and 36-44 from top to bottom.

FIG. 25 shows further round three of screening results. Sequences corresponding to SEQ ID NOs: 45, 25, 12, 24, 56-59, 14, 11, 60-64 in the upper panel from top to bottom and SEQ ID NOs: 45, 36, 65, 39, 37, 40, 41, 38, 43 and 44 in the lower panel from top to bottom.

DETAILED DESCRIPTION

Figure 1A:
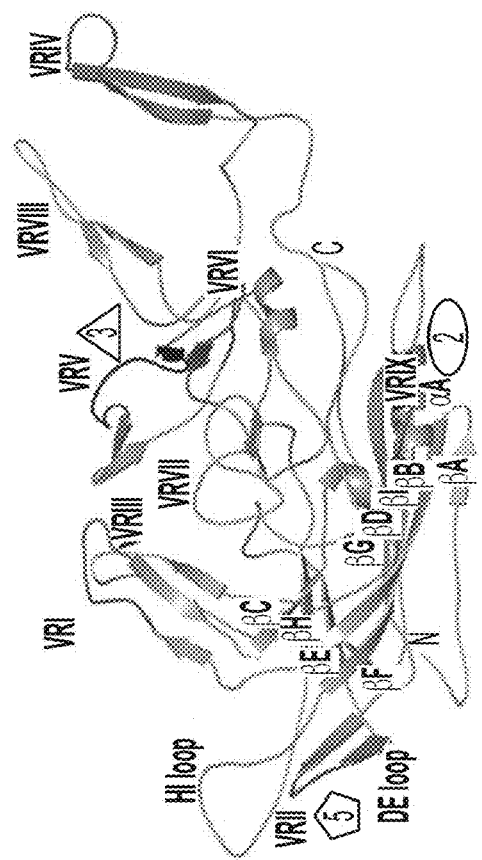
FIGS. 1A-1E show characteristics of an example AAV capsid library.
Figure 1B:
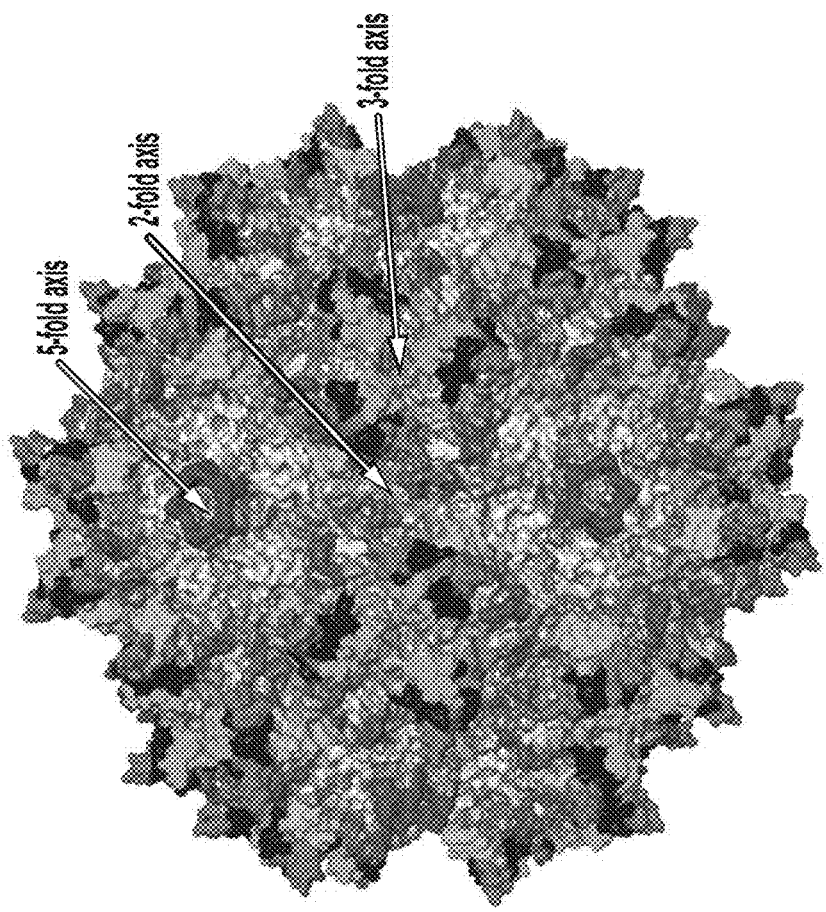
Figure 1C:
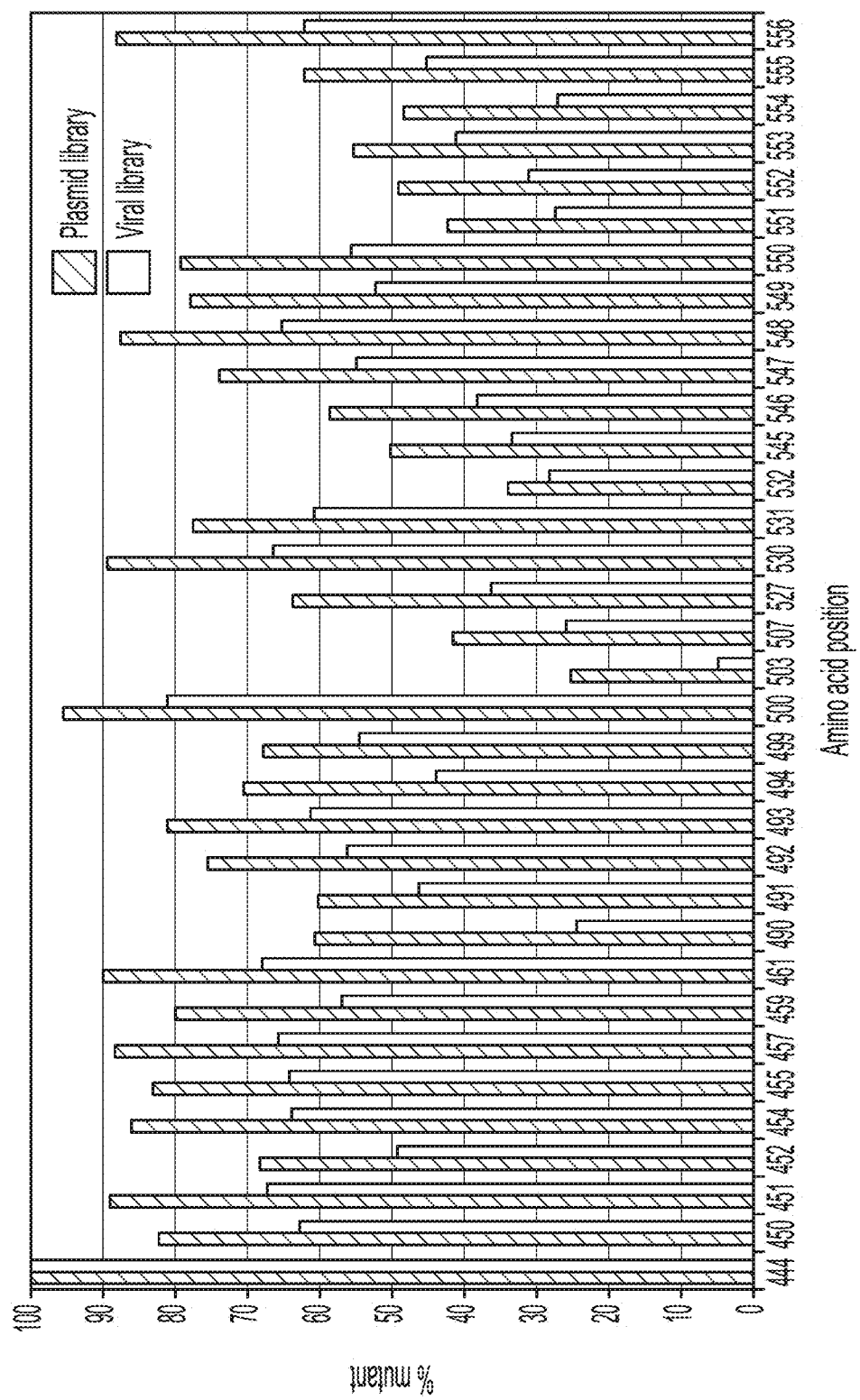
Figure 1D:
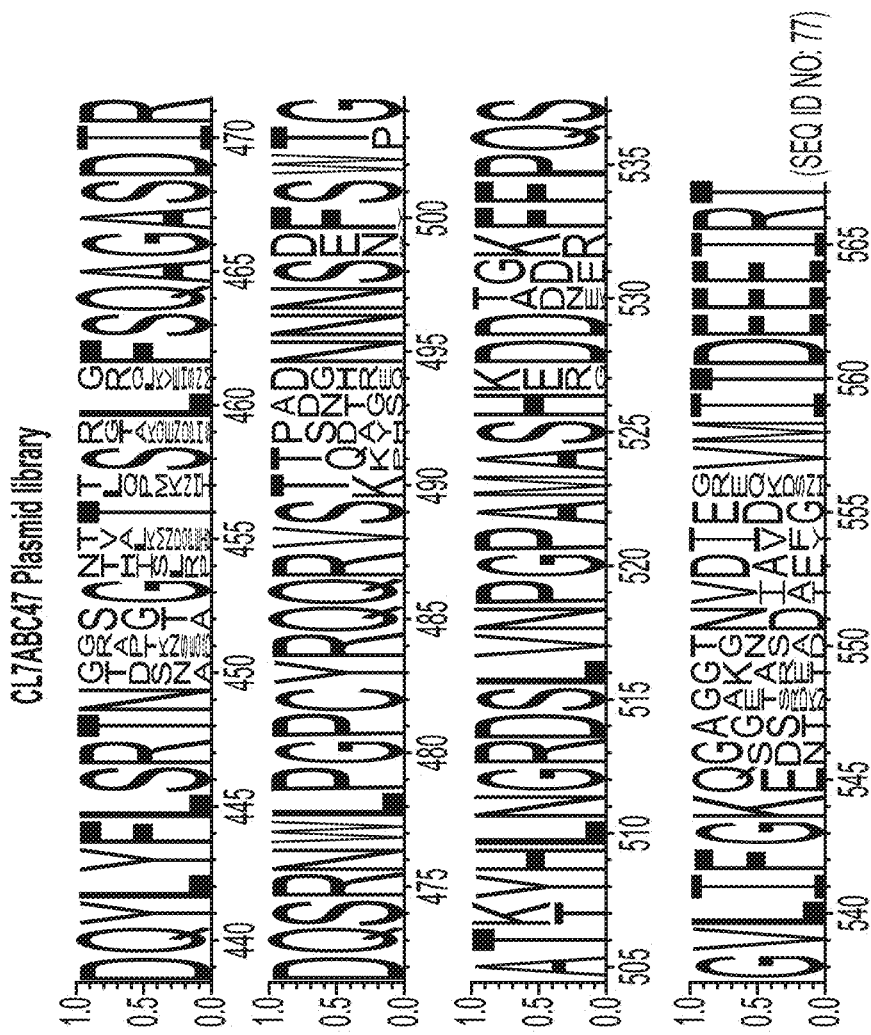
Figure 1E:
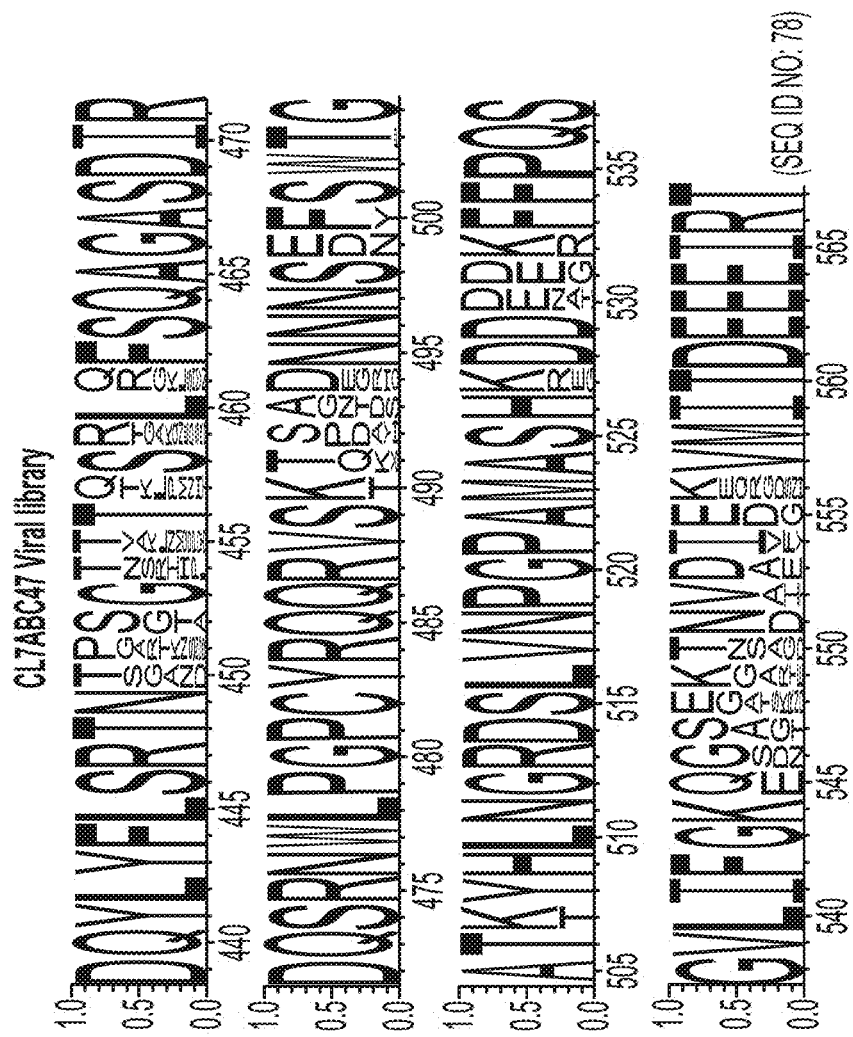

AAV-derived vectors are promising tools for human gene therapy applications because of reduced pathogenicity compared to other vectors, episomal localization, and stable transgene expression. AAV particles show huge promise for the delivery of therapeutic genes to the eye, and particularly the retina (Pierce et al. Cold Spring Harb Perspect Med. 2015, 5(9): a017285; Schon et al., Eur J Pharm Biopharm. 2015 95(Pt B): 343-52; Barnard et al., Cold Spring Harb Perspect Med. 2014, 5(3): a017293; Trapani et al., Prog Retin Eye Res. 2014,43:108-28; Carvalho and Vandenberghe, Vision Res. 2015,111(Pt B): 124-33; Dalkara and Sahel, C R Biol. 2014, 337(3):185-92; Petrs-Silva and Linden, Clin Ophthalmol. 2014; 8:127-36). Improving the transduction efficiency of AAV particles having tropism for retinal cells would therefore be of great benefit. AAV of serotype 2 is already known to have tropism for certain ocular cells, e.g., retinal cells. Accordingly, provided herein are variants of wild-type AAV (e.g., AAV2) particles having substitutions in the capsid proteins, compositions of such particles and methods of using these compositions to transduce one or more particular cell type (e.g., photoreceptors, retinal ganglion cells, neural retinal cells, Purkinje cells and ependymal cells) relative to the transduction efficiency in the same cell type of a corresponding rAAV that does not have any of the capsid variants (for example relative to a corresponding rAAV2 that has wild type AAV2 capsid proteins).

AAV Structure and Capsid Proteins

The AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The rep ORF is composed of four overlapping genes encoding Rep proteins required for the AAV life cycle. The cap ORF contains overlapping nucleotide sequences of capsid proteins: VP1, VP2 and VP3, which interact together to form a capsid of an icosahedral symmetry.

The capsid proteins, which are controlled by the same promoter, designated p40, are translated from the same mRNA. The molecular weights of VP1, VP2 and VP3 are 87, 72 and 62 kiloDaltons, respectively. The AAV capsid is composed of 60 capsid protein subunits, VP1, VP2, and VP3, that are arranged in an icosahedral symmetry in a ratio of 1:1:10.

SEQ ID NO: 1 corresponds to an example of a wild-type AAV2 VP1 amino acid sequence. The AAV2 VP2 and VP3 capsid proteins correspond to amino acids 138 to 735 and 204 to 735 of VP1, respectively. SEQ ID NOs: 2 and 3 corresponds to examples of wild-type AAV2 VP2 and AAV2 VP3 amino acid sequences.

```
wild-type AAV2 VP1 amino acid sequence:
                                    (SEQ ID NO: 1)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNRQAATADVNTQGV

LPGMVWQDRDVYLQGPIWAKIPHTDGHFHPSPLMGGFGLKEIPPPQILIK

NTPVPANPSTTFSAAKFASFITQYSTGQVSVEIEWELQKENSKRWNPEIQ

YTSNYNKSVNVDFTVDTNGVYSEPRPIGTRYLTRNL wild-type AAV2 VP2 amino acid sequence:
                                    (SEQ ID NO: 2)
MAPGKKRPVEHSPVEPDSSSGTGKAGQQPARKRLNFGQTGDADSVPDPQP

LGQPPAAPSGLGTNTMATGSGAPMADNNEGADGVGNSSGNWHCDSTWMGD

RVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLT

STVQVFTDSEYQLPYVLGSAHQGCLPPFPADVFMVPQYGYLTLNNGSQAV

GRSSFYCLEYFPSQMLRTGNNFTFSYTFEDVPFHSSYAHSQSLDRLMNPL

IDQYLYYLSRTNTPSGTTTQSRLQFSQAGASDIRDQSRNWLPGPCYRQQR

VSKTSADNNNSEYSWTGATKYHLNGRDSLVNPGPAMASHKDDEEKFFPQS

GVLIFGKQGSEKTNVDIEKVMITDEEEIRTTNPVATEQYGSVSTNLQRGN

RQAATADVNTQGVLPGMVWQDRDVYLQGPIWAKIPHTDGHFHPSPLMGGF
```

GLKHPPPQILIKNTPVPANPSTTFSAAKFASFITQYSTGQVSVEIEWELQ

KENSKRWNPEIQYTSNYNKSVNVDFTVDTNGVYSEPRPIGTRYLTRNL wild-type AAV2 VP3 amino acid sequence:

(SEQ ID NO: 3)
MATGSGAPMADNNEGADGVGNSSGNWHCDSTWMGDRVITTSTRTWALPTY

NNHLYKQISSQSGASNDNHYFGYSTPWGYFDFNRFHCHFSPRDWQRLINN

NWGFRPKRLNFKLFNIQVKEVTQNDGTTTIANNLTSTVQVFTDSEYQLPY

VLGSAHQGCLPPFPADVFMVPQYGYLTLNNGSQAVGRSSFYCLEYFPSQM

LRTGNNFTFSYTFEDVPFHSSYAHSQSLDRLMNPLIDQYLYYLSRTNTPS

GTTTQSRLQFSQAGASDIRDQSRNWLPGPCYRQQRVSKTSADNNNSEYSW

TGATKYHLNGRDSLVNPGPAMASHKDDEEKFFPQSGVLIFGKQGSEKTNV

DIEKVMITDEEEIRTTNPVATEQYGSVSTNLQRGNRQAATADVNTQGVLP

GMVWQDRDVYLQGPIWAKIPHTDGHFHPSPLMGGFGLKEIPPPQILIKNT

PVPANPSTTFSAAKFASFITQYSTGQVSVEIEWELQKENSKRWNPEIQYT

SNYNKSVNVDFTVDTNGVYSEPRPIGTRYLTRNL

Variant Recombinant AAV Proteins

The tissue tropism and transduction efficiency of AAV particles is determined by the nature of amino acid residues exposed at the surface of the capsid (Wu et al., J Virol. 2006, 80(22):11393-7). Therefore, manipulating the amino acids of the capsid proteins provides an opportunity to fine tune the tissue tropism of the particle and also improve transduction efficiency. However, certain manipulations, e.g., substitutions of amino acids, of the capsid protein can cause it to mis-fold or not form a capsid at all. To circumvent issues of protein mis-folding and capsid mis-forming, the recombinant AAV2 (rAAV2) variant proteins and particles disclosed herein were identified from a variant AAV2 capsid library that was built by making substitutions in only the variable loops of the capsid protein. Herein, "variable loops" are also referred to as "variable regions". AAV2 has 9 variable regions, numbered from VRI to VRIX. FIG. 1A shows the structure of wild-type AAV2 protein with the variable loops. Marsic et al. (Mol Ther. 2014, 22(11):1900-9) describes how such an AAV2 capsid library was made as well as its characteristics.

Screening of an AAV2 capsid library in a mouse model as well as a macaque model led to the identification of AAV2 variant proteins that possess enhanced efficiency to transduce retinal cells (e.g., PRs, RGCs and neural retinal cells) compared to the transduction efficiency of wild-type AAV2 capsid proteins.

Accordingly, provided herein are rAAV2 capsid proteins comprising substitutions, relative to the wild-type AAV2 VP1 sequence (e.g., as set for in SEQ ID NO: 1). In some embodiments, an amino acid substitution in any one of the variant AAV2 capsid proteins disclosed herein lies in a variable region as defined by wild-type AAV2 VP1 protein. It should be understood that any positioning of an amino acid as described herein is with respect to the sequence of the wild-type AAV2 VP1 sequence as set forth in SEQ ID NO: 1. The amino acids corresponding to various variable regions of AAV2 VP1 are as shown in Table 1.

TABLE 1

AAV2 capsid protein variable regions and corresponding amino acids

| Variable Region | Corresponding Amino Acids |
|---|---|
| VRI | 263-265 |
| VRII | 325-330 |
| VRIII | 381-384 |
| VRIV | 450-466 |
| VRV | 490-503 |
| VRVI | 527-532 |
| VRVII | 545-556 |
| VRVIII | 585-596 |
| VRIX | 704-713 |

In some embodiments, a variant rAAV (e.g., variant rAAV2) capsid protein has one or more amino acid substitutions in any one variable region (e.g., VRI, VRII, VRIII, VRIV, VRV, VRVI, VRVII, VRVIII or VRIX). In some embodiments, a variant rAAV (e.g., variant rAAV2) capsid protein has one or more amino acid substitutions in more than one variable region (e.g., VRI and VRII, VRI and VRVII, VRV and VRVII, VRV and VRI and VRVII or VRIV and VRII). It should be understood that variant rAAV (e.g., variant rAAV2) capsid proteins as disclosed herein can have one or more amino acid substitutions in any combination of more than one variable regions and is not limited to the examples provided above or elsewhere herein.

In some embodiments, a variant rAAV (e.g., variant rAAV2) capsid protein comprises any one or more of the amino acid substitutions shown in the sequences or substitutions in Table 2. For example, in some embodiments, a variant AAV2 capsid protein has the sequence DGE in variable region VRV. In some embodiments, a variant AAV2 capsid protein has the sequence DF in variable region VRV. In some embodiments, a variant AAV2 capsid protein has the sequences DGE and DF in variable region VRV. In some embodiments, a variant AAV2 capsid protein has the sequences DGE and DF in variable region VRV, and the sequence NA in VRI. In some embodiments, a DGE exists at amino acid positions 492-494. In some embodiments, a DF exists at amino acid positions 499-500. It is to be understood that the positions listed in Table 2 are only one of many possible amino acid positions and are non-limiting. For example, a DGE sequence may exist anywhere in variable region VRV (e.g., 490-492, 495-497, 496-500, or 500-503). All the amino acid substitutions disclosed anywhere herein can be combined with one or more of any of the other amino acid substitutions disclosed herein. For example, a DGE sequence at amino acid positions 496-500 could be combined with a DF sequence at amino acid positions 499 and 500 to result in a DGEDF sequence (SEQ ID NO: 32) in VRV.

In some embodiments, a variant rAAV (e.g., variant rAAV2) capsid protein has an amino acid listed in the second column of Table 2. In some embodiments, a variant rAAV (e.g., variant rAAV2) has an amino acid sequence that corresponds to a sequence found in FIG. 34. In some embodiments, such an amino acid can exist at a position that is offset from the position denoted in Table 2. In some embodiments, the width of the offset is up to 5 amino acids (e.g., 1, 2, 3, 4 or 5 amino acids) in either direction (upstream and downstream) for the position denoted in Table 2. For example, while a proline is designated at position 492 in VRV, a proline may exist at any position from 490 to 497 (please see S to P substitution at position 492 in VRV). In some embodiments, an amino acid listed in the second column of Table 2 is in a variant rAAV capsid protein of a serotype other than AAV2, e.g., in a homologous variable region of AAV 1, 3, 3B, 4, 5, 6, 7, 8, 9, 10, 11, 12 or 13.

In some embodiments, amino acids denoted by X are amino acids in wild-type AAV2 sequence as set forth in SEQ ID NO: 1. For example, sequence EDATENXIXXDR, as set forth in SEQ ID NO: 4, is homologous to amino acids 545 to 556 in VRVII of wild-type AAV2 VP1 protein as set forth in SEQ ID NO: 1. Therefore, in some embodiments, sequence EDATENXIXXDR (SEQ ID NO: 4) may be sequence EDATENNIDIDR (SEQ ID NO: 34). Similarly, in some embodiments, sequence RXXDD (SEQ ID NO: 8) is sequence RDDDD (SEQ ID NO: 35). In some embodiments, amino acids denoted by X are amino acids in other AAV serotypes (e.g., 1, 3, 3B, 4, 5, 6, 7, 8, 9, 10, 11, 12 or 13) at homologous positions.

TABLE 2

Amino acid substitutions or sequences in variant rAAV (e.g., variant rAAV2) capsid proteins

| Variable Region | Amino Acids sequences and/or substitutions* | Possible positions | Corresponding SEQ ID NO |
|---|---|---|---|
| VRI | NA | 263-264 | |
| | EA | 263-264 | |
| | DA | 263-264 | |
| | XX | 263-264 | |
| | Q to A | 263 | |
| | X | 267 | |
| | Q to A | 263 | |
| | S to T | 267 | |
| | S to X | 267 | |
| | S to W | 267 | |
| | QSGAS | 263-267 | 46 |
| | NAGAS | 263-267 | 47 |
| | TTGAT | 263-267 | 48 |
| | EAGAS | 263-267 | 49 |
| | TTGAS | 263-267 | 50 |
| | GAGAS | 263-267 | 51 |
| | ASGAS | 263-267 | 52 |
| | TAGAS | 263-267 | 53 |
| | QTGAS | 263-267 | 54 |
| VRII | Q to K | 325 | |
| VRIV | DEAXSEXKXTXR | 450-461 | 7 |
| | Y to F | 444 | |
| | SD | 450-451 | |
| | T to D | 450 | |
| | P to A | 451 | |
| | GAXNMXTXAXR | 451-461 | 31 |
| | S to A | 452 | |
| | ID | 454-455 | |
| | T to N | 454 | |
| | T to S | 454 | |
| | AXMXKXH | 455-461 | 30 |
| | T to V | 455 | |
| | Q to M | 457 | |
| | R to N | 459 | |
| | R to T | 459 | |
| | Q to R | 461 | |
| | Q to M | 461 | |
| VRV | K to T | 490, 507 | |
| | T to V | 491 | |
| | QD | 491-492 | |
| | S to A | 492 | |
| | S to P | 492 | |
| | YN | 492-493 | |
| | DGE | 492-494 | |
| | D to E | 494 | |
| | DF | 499-500 | |
| | QDXE | 491-494 | 9 |

TABLE 2-continued

Amino acid substitutions or sequences in variant rAAV (e.g., variant rAAV2) capsid proteins

| Variable Region | Amino Acids sequences and/or substitutions* | Possible positions | Corresponding SEQ ID NO |
|---|---|---|---|
| | E to D | 499 | |
| | Y to F | 500 | |
| | T to P | 503 | |
| | K to T | 507 | |
| VRVI | RXXDD | 527-531 | 8 |
| | RXXDXR | 527-532 | 55 |
| | DG | 530-531 | |
| | K to R | 527, 532 | |
| | E to D | 530, 531 | |
| VRVII | EDATENXIXXDR | 545-556 | 4 |
| | Q to E | 545 | |
| | SAAGADXAXDS | 546-556 | 5 |
| | SGREGDAEXXD | 546-556 | 6 |
| | AAADDXEXDG | 547-556 | 10 |
| | AGRADIXXXS | 547-556 | 33 |
| | D to E | 553 | |
| | D to A | 553 | |
| | K to S | 556 | |
| | DG | 555-556 | |
| | DS | 555-556 | |

*amino acids designated by "X" may be any known amino acid

Table 2: Amino acid substitutions or sequences in variant rAAV (e.g., variant rAAV2) capsid proteins Some non-limiting examples of variant AAV2 capsid proteins are shown in FIGS. 3 and 5. In some embodiments, a variant AAV2 capsid protein has the sequence as set forth in any one of SEQ ID NOs: 11 to 23 (see FIG. 3) or SEQ ID NOs: 24-28 (see FIG. 5) or 36-44 (see FIG. 24) or 56-65 (see FIG. 25). For example, a variant AAV2 capsid protein may have the sequence as set forth by SEQ ID NOs: 11, 12, 13, 14, 15, 16, 17, 18, 19, 20, 21, 22, 23, 24, 25, 26, 27, 28, 36, 37, 38, 39, 40, 41, 42, 43, 44, 56, 57, 58, 59, 60, 61, 62, 63, 64 or 65. In some embodiments, a variant AAV2 capsid protein has the sequence as set forth in SEQ ID NO: 11. In some embodiments, a variant AAV2 capsid protein has the sequence as set forth in SEQ ID NO: 12. In some embodiments, a variant AAV2 capsid protein has the sequence SEQ ID NO: 24. In some embodiments, a variant AAV2 capsid protein has the sequence SEQ ID NO: 25.

In some embodiments, a variant AAV2 capsid protein has sequences DGE and DF in VRV and sequence as set forth in SEQ ID NO: 4 in VRVII. In some embodiments, a variant AAV2 capsid protein has sequence NA in VRI, sequences DGE and DF in VRV, and sequence as set forth in SEQ ID NO: 5 in VRVII. In some embodiments, the variant recombinant AAV2 capsid protein comprises: (a) QS, NA, EA, DA, AS, AA, DT, NS, GA, GS, RS, TA, TS, ES, GT, QA, or TT in VRI; QDXE in VRV; Y500F; and T503P, (b) QS, NT, ES, GS, NA, AS, AA, GA or DS in VRI; Y444F; SD, ID, and/or NXM in VRIV; S492A; DF in VRV; and DG in VRVI, (c) QSGAS (SEQ ID NO: 46), NAGAS (SEQ ID NO: 47), TTGAT (SEQ ID NO: 48), EAGAS (SEQ ID NO: 49), TTGAS (SEQ ID NO: 50) or GAGAS (SEQ ID NO: 51) in VRI, (d) QS, EA, QA, NA, AS or ES in VRI; T491V; Y500F; and AAADDXEXDG (SEQ ID NO: 10) in VRVII, (e) QS, DS, NA, AS, DA or AT in VRI; E530D; and AGRADIXXXS (SEQ ID NO: 33) in VRVII, or (f) QSGAS (SEQ ID NO: 46), NAGAS (SEQ ID NO: 47), ASGAS (SEQ ID NO: 52), GAGAS (SEQ ID NO: 51), TAGAS (SEQ ID NO: 53), QTGAS (SEQ ID NO: 54) or TTGAS (SEQ ID NO: 50) in VRI; QDXE in VRV; Y500F; T503P; and SAAGADXAXDS (SEQ ID NO: 5) in VRVII. In some embodiments, a variant AAV2 capsid protein has one or more substitutions in Table 2 for the VRIV region. In some embodiments, a variant AAV2 capsid protein has one or more substitutions in Table 2 for the VRVII region.

After identifying the variant rAAV (e.g., variant rAAV2) capsid proteins with enhanced retinal transduction efficiency using screening in mice and macaque models, further modifications were made to improve transduction efficiency. For example, a method for quantifying relative transduction of photoreceptors by recombinant Adeno Associated Virus (rAAV) vectors in Rho-GFP mice has been used to identify a rationally designed capsid variant, AAV2(quadY-F+T–V), capable of outer retinal transduction following intravitreal injection (Kay et al., PLoS One. 2013, 8(4): e62097). Accordingly, in some embodiments any one of the AAV2 variant proteins described herein may further comprise any one of the following amino acid substitutions: Y272F, Y444F, Y500F, Y730F, and T491V, or a combination of thereof. For example, a variant AAV2 capsid protein has a sequence as set forth in any one of SEQ ID NOs: 1-28, and if it does not already, has a phenylalanine at one or more of the positions 272, 272, 500 and 730. In another example, a variant AAV2 capsid protein comprises the substitutions Y272F, Y444F, Y500F and Y730F. In another example, a variant AAV2 capsid protein comprises the substitutions Y272F and Y444F.

In some embodiments, a variant AAV2 capsid protein has a sequence as set forth in any one of SEQ ID NOs: 1-28, and if it does not already, has a valine at position 491. For example, a variant rAAV (e.g., variant rAAV2) capsid protein may comprise sequences DGE and DF in VRV, the sequence as set forth in SEQ ID NO: 4 in VRVII and a Y444F substitution. In some embodiments, any one of the AAV2 variant proteins described herein may further comprise any one of the following amino acid substitutions: Y252F, Y700F, and Y704F, or a combination thereof.

In some embodiments, any one of the variant rAAV (e.g., variant rAAV2) capsid proteins disclosed herein is a variant VP1 protein (e.g., a variant AAV2 VP1 protein). In some embodiments, any one of the variant rAAV (e.g., variant AAV2) capsid proteins disclosed herein is an AAV VP2 protein (e.g., a variant AAV2 VP2 protein). In some embodiments, any one of the variant rAAV (e.g., variant AAV2) capsid proteins disclosed herein is an AAV VP3 protein (e.g., a variant AAV VP3 protein). It is to be understood that any of the variants can be in a VP1, VP2, or VP3 protein.

It is to be understood that any one of the variant rAAV (e.g., variant rAAV2) capsid proteins disclosed herein may have any one single amino acid substitution described herein, or any combination of amino acid substitutions described herein. For example, a variant rAAV (e.g., variant rAAV2) capsid protein may have sequence RXXDD (as set forth in SEQ ID NO: 8) as the only substitutions, or it might have additional amino acid substitutions (e.g., NA in VRI; Y444F; P451A, T454N, T455V and/or R459T in VRIV).

Contemplated herein are also variant rAAV capsid proteins of serotypes other than serotype 2. In some embodiments, any one of the amino acid substitutions described herein are in a variable region of the capsid protein of a serotype other than serotype 2 that is homologous to the variable region of AAV2. In some embodiments, a variant rAAV capsid protein of a serotype other than serotype 2 is of any serotype other than AAV2 (e.g., 1, 3, 3B, 4, 5, 6, 7, 8, 9, 10, 11, 12 or 13). In some embodiments, a variant rAAV capsid protein of a serotype other than serotype 2 is of a closely related serotype (e.g., AAV1 or AAV6). see: PCT Application Publication Number WO2015121501A1.

Nucleic Acids Encoding Variant rAAV Capsid Proteins

Provided herein are also nucleic acids that encode any one of the variant rAAV capsid proteins disclosed herein. In some embodiments, a nucleic acid encoding a variant rAAV capsid protein is comprised in a plasmid.

Recombinant AAV Particles

Provided herein are variant rAAV (e.g., variant rAAV2) particles. In some embodiments, a particle is an empty particle (e.g., one that does not contain a nucleic acid vector comprising a gene of interest). In some embodiments, an AAV2 particle contains a nucleic acid vector comprising a gene of interest. As used herein, "a gene of interest" is a gene that encodes a RNA or protein of interest.

In some embodiments, a rAAV2 particle containing any one of the variant rAAV (e.g., variant rAAV2) capsid proteins disclosed herein comprises ITRs and/or rep ORF of serotype 2. In some embodiments, a rAAV2 particle is a pseudotyped rAAV particle, which comprises (a) a capsid comprised of capsid proteins derived from serotype 2, and (b) a nucleic acid vector comprising ITRs from another serotype (e.g., AAV1, AAV3, AAV4, AAV5, AAV6, AAV7, AAV8, AAV9, or AAV10). For example, a particle may have ITRs of serotype 5 and a capsid of serotype 2. Such a pseudotyped rAAV particle would be designated AAV5/2.

A protein of interest may be a detectable marker or a therapeutic protein. A detectable marker is a molecule that can be visualized (e.g., using a naked eye or under a microscope). In some embodiments, the detectable marker is a fluorescent molecule, a bioluminescent molecule, or a molecule that provides color (e.g., β-galactosidase, β-lactamases, β-glucuronidase and spheriodenone). In some embodiments, a detectable marker is a fluorescent protein or functional peptide or functional polypeptide thereof.

In some embodiments, a gene of interest encodes a therapeutic protein and is referred to as a "therapeutic gene." A therapeutic gene may provide a therapeutic effect in a cell, tissue or organ to which it is delivered. For example, a therapeutic gene delivered to the intravitreal space of an eye (or two eyes) may benefit the photoreceptor cells of the retina of the eye (or two eyes) to which the gene was delivered. In some embodiments, a therapeutic gene provides a therapeutic benefit to a cell, tissue or organ other than the one to which it is delivered. For example, a gene delivered to the brain may reach the retina of the eyes via the optic nerve and benefit one or more type of retinal cell (e.g., retinal ganglion cells). In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA or other nucleic acid or protein for gene editing. In some embodiments, a gene of interest encodes a therapeutic RNA, e.g., a small interfering RNA.

In some embodiments, a nucleic acid vector comprised in a rAAV2 particle comprises one or more of the following: (a) one or more heterologous nucleic acid regions comprising a gene of interest, and (b) one or more regions comprising inverted terminal repeat (ITR) sequences (e.g., wild-type ITR sequences or engineered ITR sequences) flanking the one or more nucleic acid regions (e.g., heterologous nucleic acid regions). In some embodiments, a nucleic acid vector in a rAAV particle comprises one or more nucleic acid regions comprising a control sequence that facilitates expression of the heterologous nucleic acid region (e.g., a promoter). In some embodiments, a nucleic acid vector in a rAAV2 particle comprises one or more nucleic acid regions comprising a sequence that facilitates integration of the heterologous nucleic acid region (optionally with the one or more nucleic acid regions comprising a sequence that facilitates expression) into the genome of the subject.

Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer).

In some embodiments, one or more promoters may be operably linked to a coding nucleotide sequence in the heterologous nucleic acid. A promoter is "operably linked" to a nucleotide sequence when the promoter sequence controls and/or regulates the transcription of the nucleotide sequence. A promoter may be a constitutive promoter, tissue-specific promoter, an inducible promoter, or a synthetic promoter.

For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. In some embodiments, chimeric viral/mammalian promoters may include a chimeric CMV/chicken beta actin (CBA, CB or CAG) promoters.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. In some embodiments, it may be beneficial to combine a variant rAAV (e.g., variant rAAV2) particle as disclosed herein, with a promoter that also targets the same cells, tissue, or organ as the variant rAAV (e.g., variant rAAV2) particle. For example, a variant rAAV (e.g., variant rAAV2) particle that targets photoreceptor cells of the retina might encapsidate a nucleic acid comprising a promoter that also targets photoreceptor cells or the retina as a whole. In some embodiments, a cell-type-specific promoter targeting the retina is human rhodopsin kinase promoter (hGRK1). Non-limiting examples of hGRK1 promoter can be found in Beltran et al., 2010, Gene Ther. 17:1162, Zolotukhin et al., 2005, Hum Gene Ther. 16:551, and Jacobson et al., Mol Ther. 13:1074. In some embodiments, a retina-specific promoter is a Pleiades Mini-promoter (for example Ple155). In some embodiments, a retina-specific promoter is glial fibrillary acidic protein promoter. Other non-limiting examples of promoters that can be used as retinal cell-type-specific promoters include red opsin promoter "PR2.1" (which targets M and L cones), chimeric 'IRBPe-GNAT2' promoter (which targets all cones), IRBP promoter (which targets rods), Grm6-SV40 enhancer/promoter (which targets bipolar cells), Thy1 (which targets RGCs), other Pleiades promoters, rod opsin promoter (which targets rods), cone arrestin promoters (which targets all cones), VMD2 or Bestrophin promoter (which targets RPE cells).

Several promoters are publically available or described. For example, Ple155 promoter is available through Addgene plasmid repository (Addgene plasmid #29011, addgene.org/29011/) and is described in Scalabrino et al. (Hum Mol Genet. 2015, 24(21):6229-39). Ye et al. (Hum Gene Ther.; 27(1):72-82) describes a shorter version of this promoter called PR1.7. A Thy1 promoter construct is also available through Addgene plasmid repository (Addgene plasmid #20736, addgene.org/20736/). A GRM6 promoter construct is also available through Addgene plasmid repository (Addgene plasmid #66391, addgene.org/66391/). Guziewicz et al. (PLoS One. 2013 Oct. 15; 8(10): e75666) and Esumi et al (J Biol Chem. 2004, 279(18):19064-73) provide examples of the use of VMD2 promoter. Dyka et al. (Adv Exp Med Biol. 2014; 801: 695-701) describes cone specific promoters for use in gene therapy, including IRBP and IRBPe-GNAT2 promoter. The use of PR2.1 promoter has been demonstrated in Komiromy et al. (Gene Ther. 2008 July; 15(14):1049-55) and its characterization in Karim et al. (Tree Physiol. 2015 October; 35(10):1129-39). Aartsen et al. (PLoS One, 5(8): e12387) describes the use of GFAP promoter to drive GFP expression in Muller glial cells. Other examples of Muller glia specific promoters are RLBP1 and GLAST (Vázquez-Chona, Invest Ophthalmol Vis Sci. 2009, 50(8):3996-4003; Regan et al., Journal of Neuroscience, 2007, 27(25): 6607-6619).

Synthetic promoters are also contemplated herein. A synthetic promoter may comprise, for example, regions of known promoters, regulatory elements, transcription factor binding sites, enhancer elements, repressor elements, and the like.

It is to be understood that a promoter may be a fragment of any one of the promoters disclosed herein, or one that retains partial promoter activity (e.g., 10-90, 30-60, 50-80, 80-99 or 90-99.9% of the activity) of a whole promoter.

Any nucleic acid vector described herein may be encapsidated by a viral capsid. In some embodiments a cap gene is modified to express a fusion protein comprising a detectable marker and VP proteins of AAV serotype 2. In some embodiments, a peptide is inserted into the capsid protein either at position 587/588 or at the C-terminus of VP2. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complementary vector that contains a region of the nucleic acid vector that is complementary to another region of the nucleic acid vector, initiating the formation of the double-strandedness of the nucleic acid vector.

Method of Making rAAV Particles

Various methods of producing rAAV particles and nucleic acid vectors are known (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). In some embodiments, a vector (e.g., a plasmid) comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP region as described herein), and transfected into a recombinant cells, called helper or producer cells, such that the nucleic acid vector is packaged or encapsidated inside the capsid and subsequently purified.

Non-limiting examples of mammalian helper cells include HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). A non-limiting example of an insect helper cells is Sf9 cells (see, e.g., ATCC® CRL-1711™). A helper cell may comprise rep and/or cap genes that encode the Rep protein and/or Cap proteins. In some embodiments, the packaging is performed in vitro (e.g., outside of a cell).

In some embodiments, a nucleic acid vector (e.g., a plasmid) containing the gene of interest is combined with one or more helper plasmids, e.g., that contain a rep gene of a first serotype and a cap gene of the same serotype or a different serotype, and transfected into helper cells such that the rAAV particle is packaged. In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example, pSub201 is a plasmid that comprises the coding regions of the wild-type AAV2 genome (Samulski et al. (1987), J Virology, 6:3096-3101).

ITR sequences and plasmids containing ITR sequences are known in the art and are commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci U S A. 1996 Nov. 26; 93(24):14082-7; and Curtis A. Machida. Methods in Molecular Medicine™ Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Genebank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety.

A non-limiting method of rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. As an example, HEK293 cells (available from ATCC®) are transfected via CaPO4-mediated transfection, lipids or polymeric molecules such as Polyethylenimine (PEI) with the helper plasmid(s) and a plasmid containing a nucleic acid vector. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

Methods for large-scale production of AAV using a herpesvirus-based system are also known. See for example, Clement et al. (Hum Gene Ther. 2009, 20(8):796-806). Methods of producing exosome-associated AAV, which can be more resistant to neutralizing anti-AAV antibodies, are also known (Hudry et al., Gene Ther. 2016, 23(4):380-92; Macguire et al., Mol Ther. 2012, 20(5):960-71).

Methods for producing and using pseudotyped rAAV vectors are also known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Compositions

Various formulations have been developed to facilitate rAAV particle use. For example, for administration of an injectable aqueous solution of rAAV particles, the solution may be suitably buffered, if necessary, and the liquid diluent first rendered isotonic with sufficient saline or glucose. In some embodiments, a composition as provided herein comprises a plurality of any one of the variant rAAV (e.g., variant rAAV2) particles disclosed herein. In some embodiments, a composition comprises pluralities of more than one of the variant rAAV (e.g., variant rAAV2) particles disclosed herein. In some embodiments, "administering" or "administration" means providing a material to a subject in a manner that is pharmacologically useful.

Accordingly, in some embodiments, a composition of variant rAAV particles comprises a pharmaceutically acceptable carrier. The term "carrier" refers to a diluent, adjuvant, excipient, or vehicle with which the rAAV particle is administered. Such pharmaceutical carriers can be sterile liquids (e.g., water, oils, saline solutions, aqueous dextrose and glycerol solutions), suspending agents, preserving agents (e.g., methyl-, ethyl-, and propyl-hydroxy-benzoates), and pH adjusting agents (such as inorganic and organic acids and bases). In some embodiments, carriers include buffered saline solutions (e.g., phosphate buffered saline, HEPES-buffered saline). USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

In some embodiments, a composition comprising any one of the rAAV particles disclosed herein comprises Balanced Salt Solution (BSS) supplemented with 0.014% Tween 20 (polysorbate 20). In some embodiments, a composition comprising any one of the rAAV particles disclosed herein comprises 100 mM sodium citrate, 10 mM Tris, pH 8.0, supplemented with 0.001% Pluronic F-68.

Typically, compositions may contain at least about 0.1% of the therapeutic agent (e.g., rAAV particle) or more, although the percentage of the active ingredient(s) may be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms of rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

Preparation of compositions for administration to a subject are known in the art. For example, a dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Methods of Transducing Cells

Any one of the rAAV particles, or compositions comprising any one of the rAAV particles disclosed herein can be used to transduce a cell, tissue or organ. In some embodiments, a cell, tissue or organ that is transduced using any one of the variant rAAV (e.g., variant rAAV2) particles disclosed herein is transduced with a gene of interest that may be a therapeutic gene or one that is desired to study. In some embodiments, a cell, tissue or organ is transduced in an in vitro setting wherein the cell, tissue or organ is incubated or perfused with a media. A cell may be one of many cells cultured under certain conditions, or part of an organ that is harvested, part of an organoid, or an organism.

In some embodiments, a cell, tissue or organ is transduced in vivo, for example, for the purposes of treating a disease. In some embodiments, such a rAAV particle comprises a gene of interest that encodes a therapeutic protein or RNA. In some embodiments, provided herein is a method of transducing a cell or tissue of an eye (or two eyes) or brain. In some embodiments, a specific tissue in the eye (or two eyes) or brain in targeted. For example, the retina or one or more cell type of the retina may be targeted (e.g., photoreceptors (PR), retinal ganglion cells (RGC), bipolar cells, trabecular meshwork, retinal pigment epithelium (RPE) cells, amacrine cells, astrocytes, horizontal cell, microglia, or Muller glia).

Some non-limiting examples of retinal diseases that may be treated using any one of the compositions provided herein include age-related macular degeneration, choroidermia, color blindness, Leber's congenital amaurosis, reitinitis pigmentosa, Stargardt's disease, Acromatopsia, Blue cone monochromacy, Cone-rod dystrophy, congenital stationary night-blindness, Leber's hereditary Optic Neuropathy and Glaucoma. Some non-limiting examples of syndromic diseases where the retina and other neurons such as brain and sensory organs such as the ear may be treated using any one of the compositions provided herein include Bardet-Biedl syndrome, Glycogen storage diseases, Ceroid lipofuscinosis, Canavan disease, Friedreich's ataxia, Pompe's and Usher's syndrome. Accordingly, any one of the variant rAAV particles as disclosed herein or compositions comprising any one of the variant rAAV particles as disclosed herein, can be used to target the inner ear.

In some embodiments, a composition comprising any one or more of the variant rAAV (e.g., variant rAAV2) particles disclosed herein is provided to photoreceptor cells (PRs). In some embodiments, a composition comprising any one or more of the variant rAAV (e.g., variant rAAV2) particles disclosed herein is provided to retinal ganglion cells (RGCs). In some embodiments, a composition comprising variant rAAV (e.g., variant rAAV2) particles is provided to a PR and/or RGC via an intravitreal injection to the subject carrying the PR and/or RGC. In some embodiments, a composition is provided via subretinal injection. In some embodiments, a composition is provided via subILM injection. Other non-limiting examples of routes to administrate a composition as disclosed herein to the eye (or two eyes) of a subject include intracameral, periocular and subconjunctival injections. In some embodiments, a composition may be injected into the lateral geniculate nucleus of a subject. Such a method may be used to target RGCs. In some embodiments, a composition may be administered topically to an eye or two eyes of a subject (e.g., in eye drops).

In some embodiments, the tissue of the brain that is targeted comprises Purkinje cells or ependymal cells. The Purkinje cells project to the deep cerebellar nuclei and are the only output cells of the cerebellar cortex. Conditions involving Purkinje cells include ataxia telangiectasia and Niemann Pick disease type C, as well as cerebellar essential tremor. Purkinje cells can also be damaged in Alzheimer's disease and by rabies virus. Purkinje cells also play a role in degenerative diseases of the cerebellum (Ferrer et al., Clin Neuropathol. 1988, 7(1):22-8).

Ependymal cells make up the ependyma, which is the thin epithelial lining of the ventricular system of the brain and the central canal of the spinal cord. Ependymal cells play an important role in the production and regulation of CSF, and act as reservoir cells in the forebrain, which can be activated after stroke and as in vivo and in vitro stem cells in the spinal cord. As such, these cells can be used to supply beneficial molecules to other cells in contact with CSF. For example, ependymal cells can be used to provide growth factors to other cells by transducing them with a gene that encodes one or more growth factors.

In some embodiments, a method of transducing an ependymal or Purkinje cell with a gene of interest involves providing to the ependymal cell or the Purkinje cell any one of the compositions provided herein. In some embodiments, such a composition is administered to a subject via intraventricular injection. In some embodiments, a variant rAAV particle that is used to transduce Purkinje and/or ependymal cells with a gene of interest comprises sequences DGE and DF in VRV, NA in VRI; and SEQ ID NO: 5 in VRVII. In some embodiments, a composition is administered to a subject via intrathecal injection, intracisternal injection, intracranial (e.g., thalamic, intracerebroventricular or ventral tegmental) injection.

In some embodiments, a subject in which a cell, tissue or organ is transduced is a vertebrate animal (e.g., a mammal or reptile). In some embodiments, a mammalian subject is a human, a non-human primate, a dog, a cat, a hamster, a mouse, a rat, a pig, a horse, a cow, a donkey or a rabbit. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, a subject is a model for a particular disease or used to study the pharmacokinetics and/or pharmacokinetics of a protein or siRNA encoded by a gene of interest.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host cell, tissue or organ. A therapeutically acceptable amount may be an amount that is capable of treating a disease, e.g., Leber's congenital amaurosis. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

Examples

Example 1: AAV capsid library

An AAV capsid library was created to encompass as much of the 'natural' variation of existing Parvoviruses (see FIGS. 1A-1E). The capsid library was built with an AAV2 cap backbone using a structure informed approach. Diversification was restricted to the variable loops of the AAV capsid protein, which increases the likelihood of creating variants that assemble and package properly. The AAV capsid library was then screened in mice and non-human primates (see Examples 2 and 3, respectively) to identify the most prevalent AAV variants, which there subsequently validated and characterized.

Example 2: Mouse Screen

Figure 2:
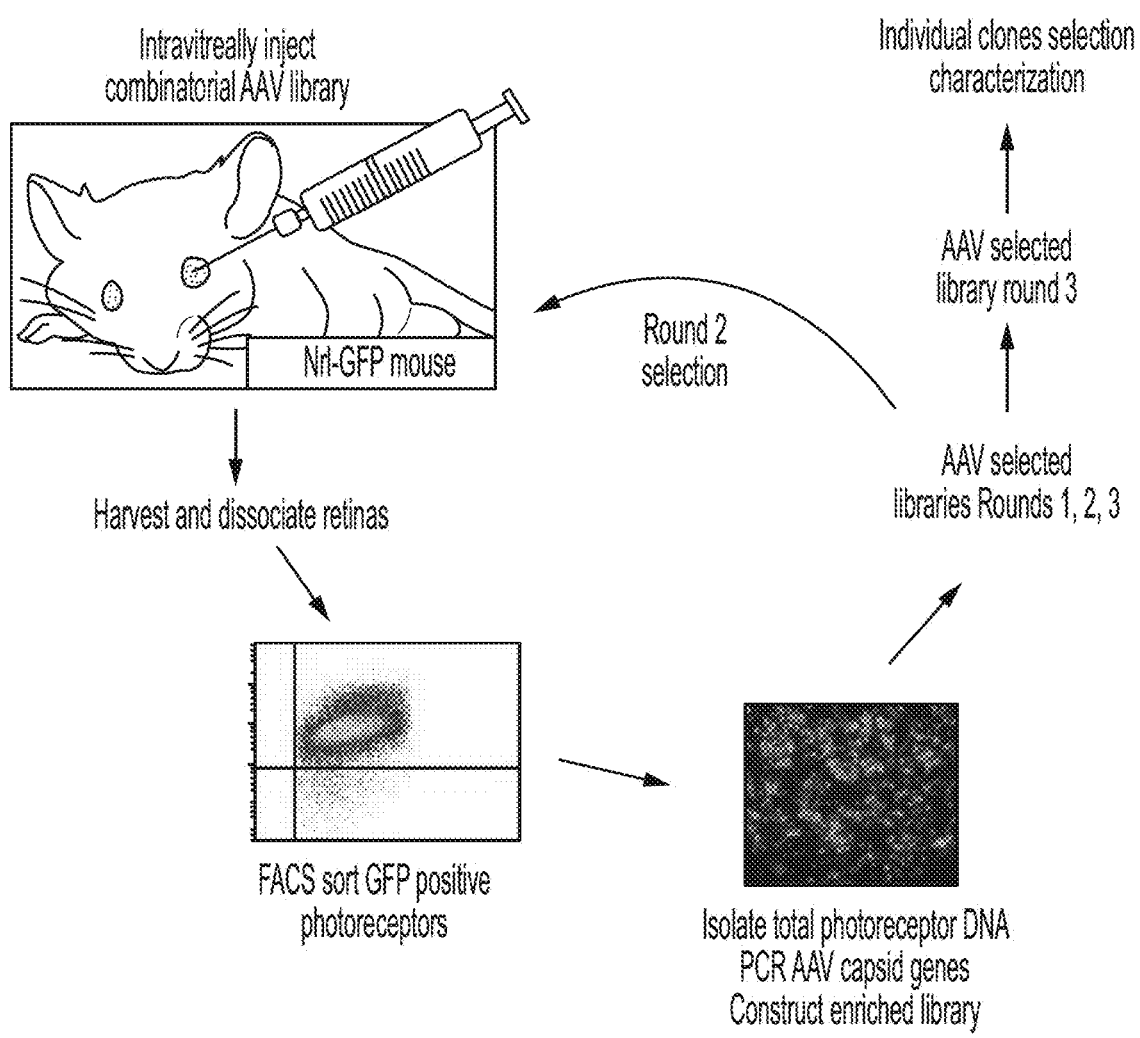
FIG. 2 depicts how the CAPLIB-7 AAV capsid library was screened in mice for transducing retinal cells. Three rounds of screens were performed, wherein Nrl-GFP mice were intravitreally injected with the combinatorial AAV library and AAV variants identified based on prevalence.

The AAV capsid library (FIGS. 1A-1E) was screened in mice as shown in FIG. 2. The transgenic mice used for screening express enhanced green fluorescent protein (EGFP) under the control of neural retina leucine zipper (nrl) gene promoter specifically in rod photoreceptors (PRs).

Capsid variants contained a self-complementary AAV genome carrying the truncated CBA promoter driving mCherry (sc-smCBA-mCherry) expression. Transduction was quantified in vitro using ocular cell lines.

The AAV library was intravitreally injected into Nrl-GFP mice. The GFP positive photoreceptors were sorted by FACS. Total DNA from photoreceptors was isolated and PCR for AAV capsid genes carried out to construct an enriched library. After three rounds of screening, a subset of the most prevalent variants was identified (FIG. 3). As shown in FIG. 3, the first most prevalent AAV2 capsid variant had around a 32% relative frequency and the second most prevalent AAV2 capsid variant had around a 21% relative frequency. These heavily enriched variants were selected for further analysis.

Example 3: NHP Screen

The AAV capsid library (FIGS. 1A-1E) was also screened in macaques (*Macacca fascicularis*) in order to identify AAV variants that target PRs and RGCs after intravitreal (Ivt) injection.

Sortable cell populations were created in primate retina using a method described in patent application No. 62/296,056, which is incorporated herein by reference in its entirety. This method is also described in Choudhury, et al., Front Neurosci. 2016,10:551. Briefly, macaque PRs and RGCs were fluorescently labelled by sub retinal injection of AAV5-

GRK1-GFP and retrograde transport of MICRO-RUBY™ (TRITC-Dextran-Biotin) from the lateral geniculate nucleus (LGN), respectively. As shown in FIG. 4, the capsid library was delivered subsequent to the injection into the LGN during the in-life phase by Ivt injection. Retinas were anatomically separated into different regions and cells from each region underwent fluorescent activated cell sorting (FACS) (see FIG. 4).

FIG. 5 shows the most prevalent AAV2 capsid variants that were isolated after two rounds of screening the capsid library in macaques. The four most prevalent AAV variants V1 (which is the same as Vb) to V4 (which is the same as Va) were selected for validation and further analysis, all of which displayed substantially improved transduction in vitro compared to wild-type AAV2 capsid. Interestingly, variants V1 (which is the same as Vb) to V4 (which is the same as Va), were also identified as the second (Vb) and most prevalent (Va) variants in the mouse screen.

Example 4: Evaluation of Transduction Profiles of AAV2 Variant Va

After the most prevalent AAV2 variants were identified by screening in mouse and macaque models, as described above, the most prevalent variants were vectorized and tested for efficiency to transduce retinal cells.

Figure 6A:
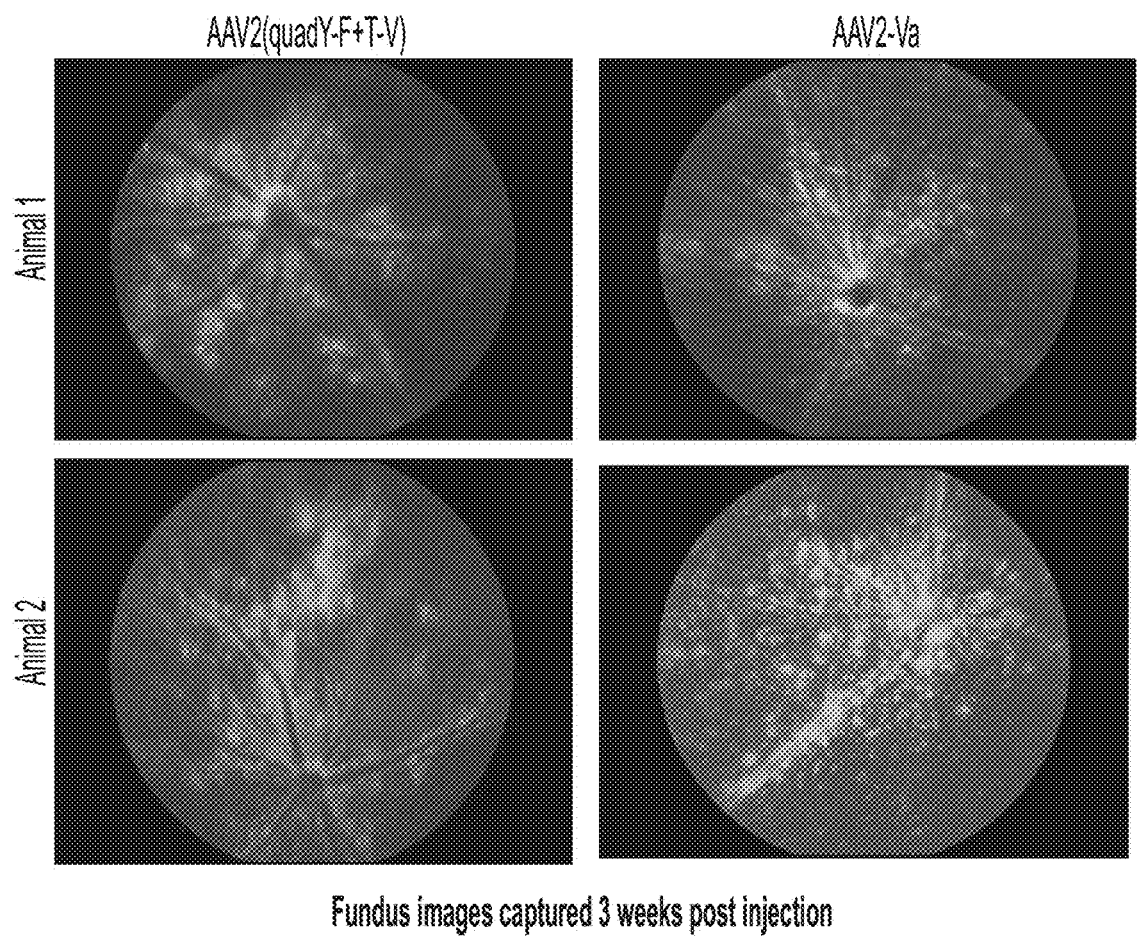
Figure 6C:
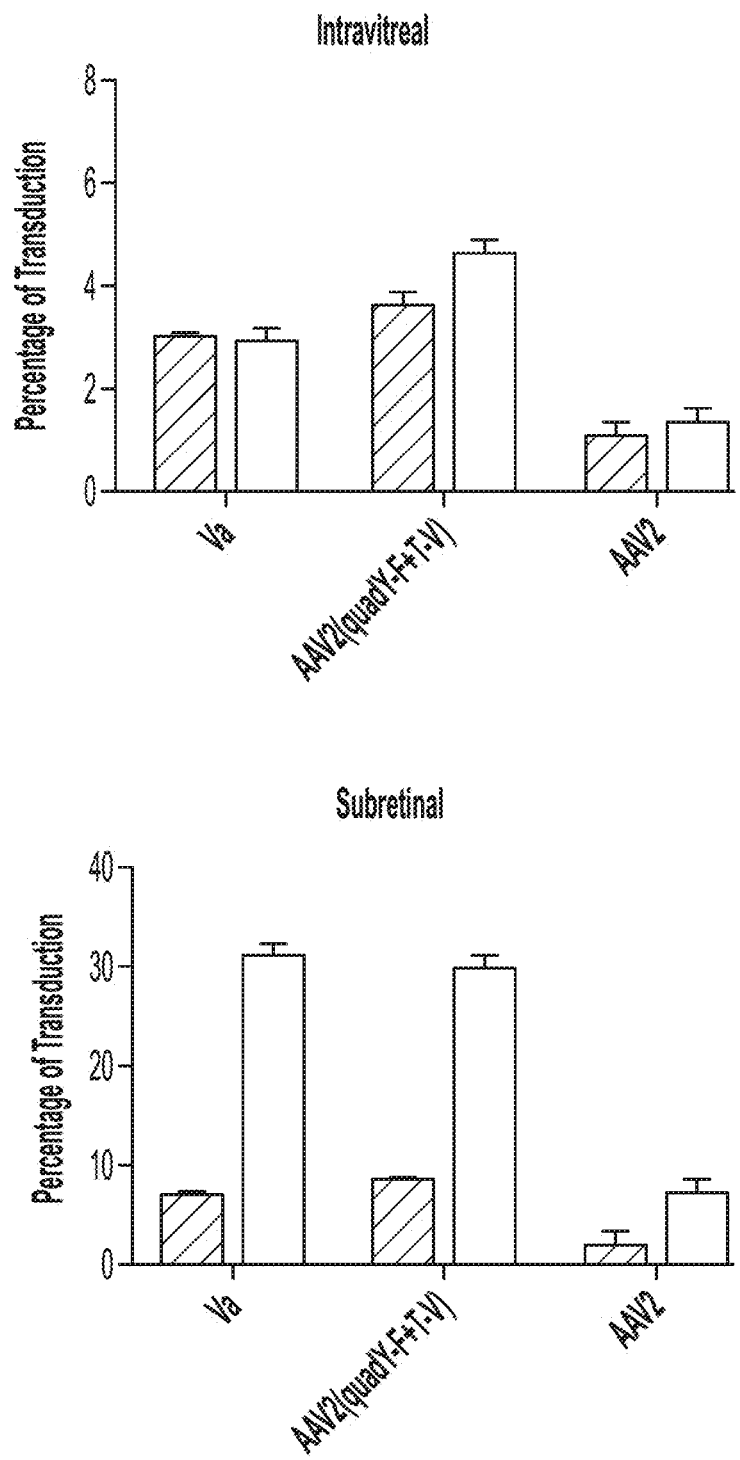

AAV2 variant Va was found to be the most prevalent in the mouse screen and the fourth most prevalent in the macaque screen. FIGS. 6A-6C show the transduction profile of Va after Nrl-GFP mice were injected intravitreally with 1 μl of $2e^{12}$ vg/ml of Sc-smCBA-mCherry packaged in a Va variant AAV2 capsid. Three weeks after the injection, transduction was evaluated by funduscopy (see FIG. 6A) and FACS (see FIGS. 6B and 6C). An AAV2 variant known to have enhanced transduction efficiency in retinal cells, AAV2 (quadY-F+T-V), was included as a control. It can be seen in FIG. 6A that compared to the AAV2(quadY-F+T-V), the AAV2 Va variant particle carrying the gene for mCherry was able to transduce just as many, if not a higher number of retinal cells and with just as much expression per cell, if not greater expression per cell.

Four weeks after injection of the Va variant AAV2 particles, the mice were sacrificed, and retinal cells dissociated and sorted for GFP expression and mCherry expression. The PE-Texas Red channel in the cytometer was used to detect mCherry expression. In FIG. 6B, the top right quadrant corresponds to the population of rod photoreceptors transduced by rAAV vector (GFP+ and mCherry+) and the bottom right quadrant corresponds to non-rod, neural retinal cells transduced by rAAV vector (mCherry+only).

FIG. 6C shows transduction rates for AAV2 variant Va when either administered to mice by intravitreal injection or subretinal injection. Mice were sacrificed 4 weeks after injection with the AAV2 variant particles. $2\times10^9$ vg was injected. Compared to when the virus particles were delivered intravitreally, subretinally administered AAV2-Va was able to transduce a higher number of non-rod, neural retinal cells. The levels of transduction achieved in both rod PRs and non-rod, neural retinal cells after subretinal injection were comparable to those achieved with 2.5 times more of the wild-type AAV2 virus.

Figure 7A:
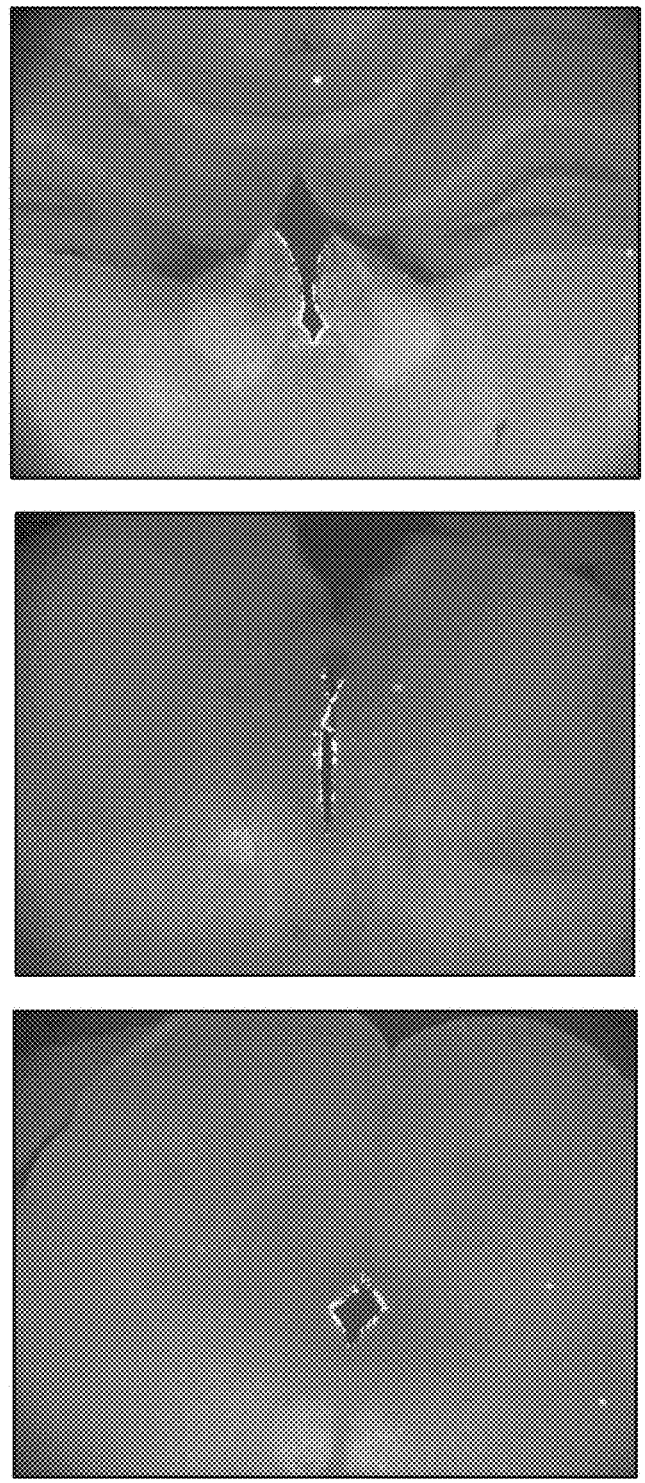
FIGS. 7A-7B show mCherry expression in brain sections from a mouse intraventricularly injected (3rd ventricle) with AAV2-Va particles carrying Sc-smCBA-mCherry.
Figure 7B:
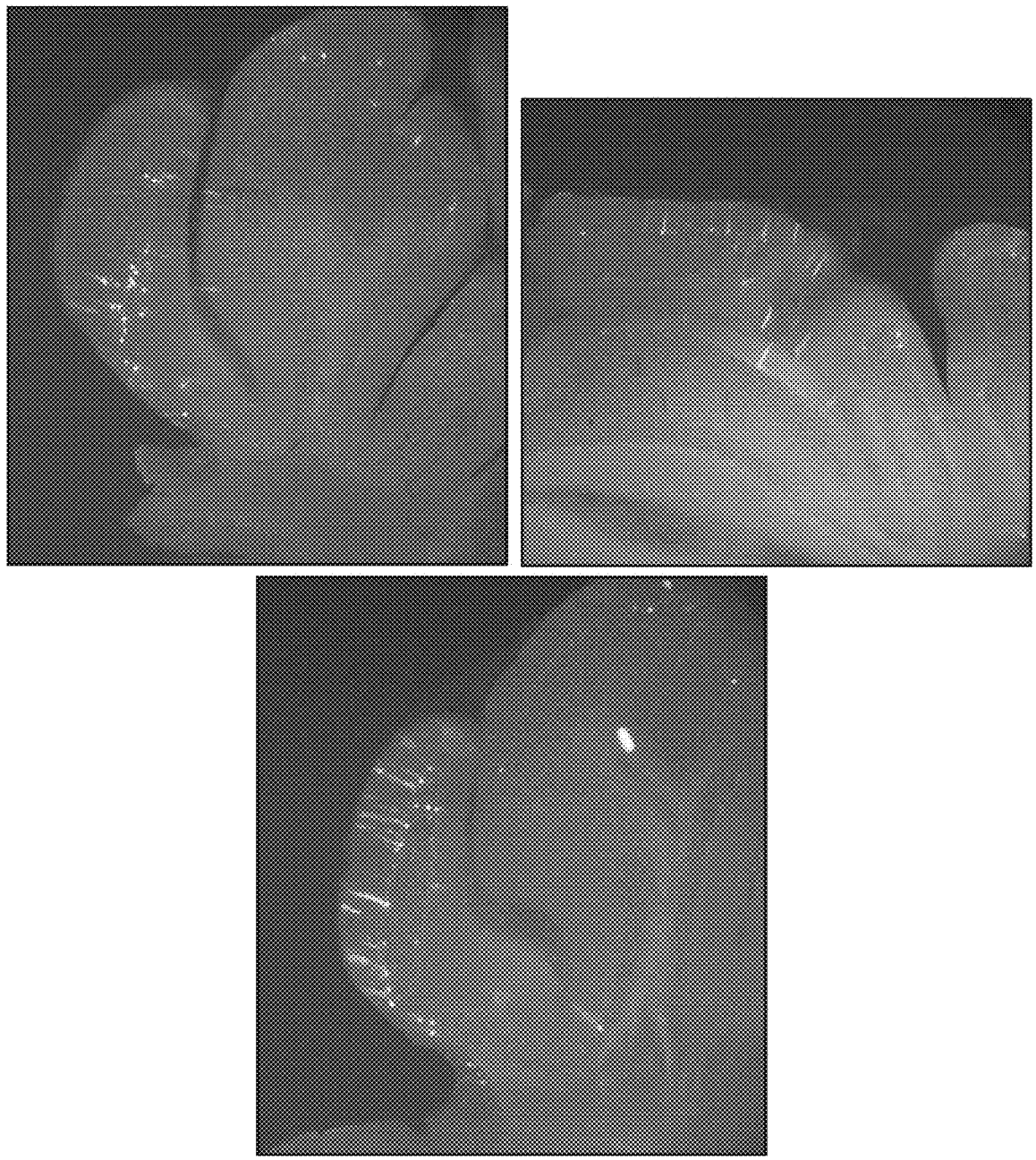

In addition to testing for transduction of retinal cells, experiments were done to assess the ability of the AAV2 variant Va capsid to transduce ependymal and Purkinje cells. Mice were injected with $4\times10^9$ vg of virus particles carrying Sc-smCBA-mCherry. Four weeks thereafter, the mice were sacrifices and sections of the brain were prepared. As shown in FIG. 7A, AAV2-Va promotes the transduction of ependymal cells, which are responsible for secreting CSF and are an attractive target for neuroprotective gene therapy. As shown in FIG. 7B, AAV2-Va particles were also able to transduce Purkinje cells.

Example 5: Evaluation of Transduction Profiles of AAV2 Variant Vb

Figure 8A:
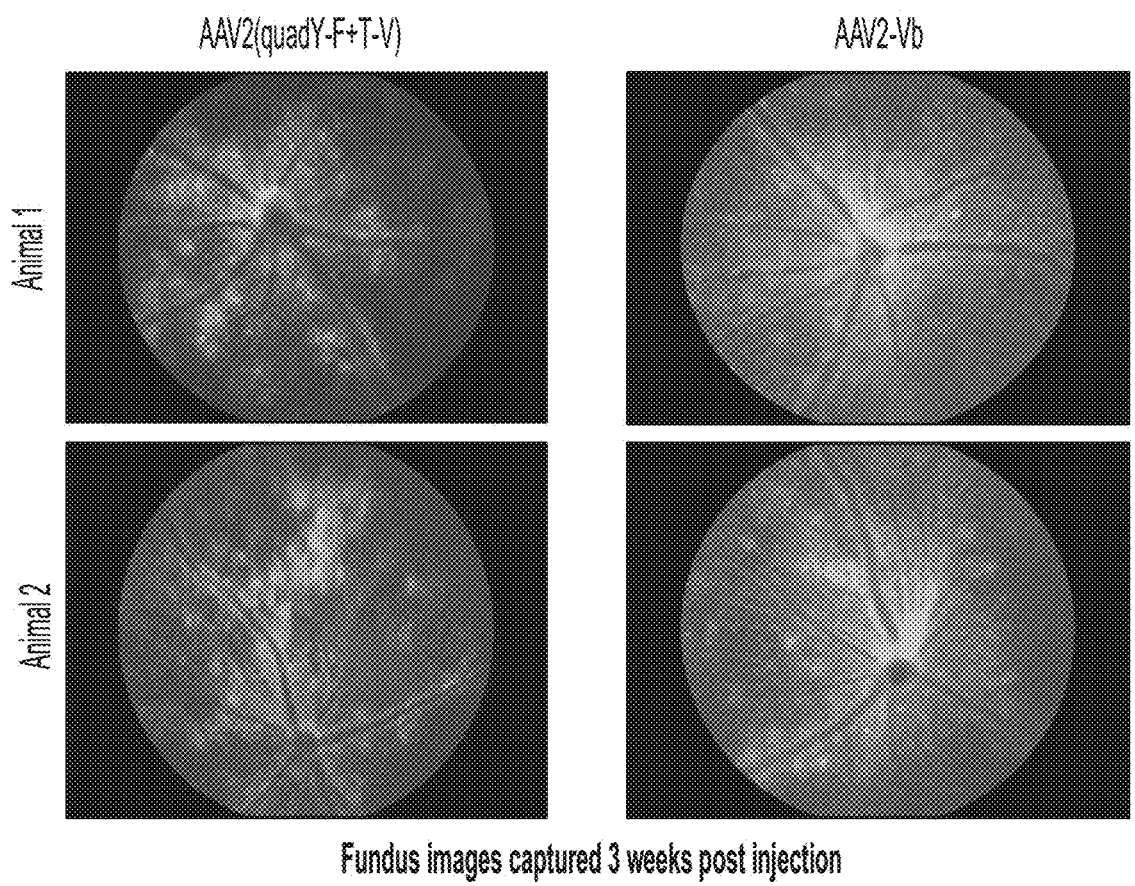
FIGS. 8A-8C.
Figure 8B:
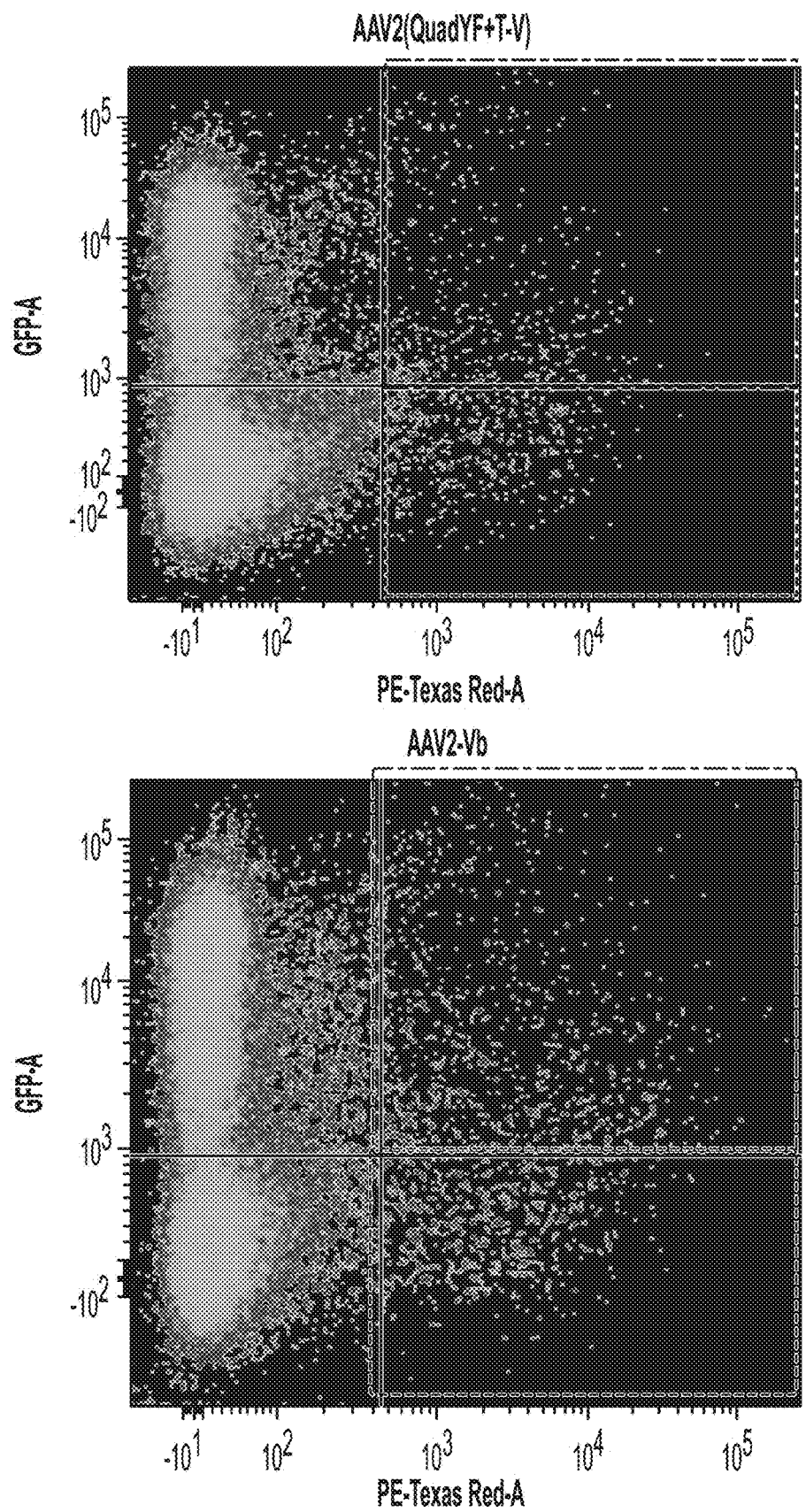
Figure 8C:
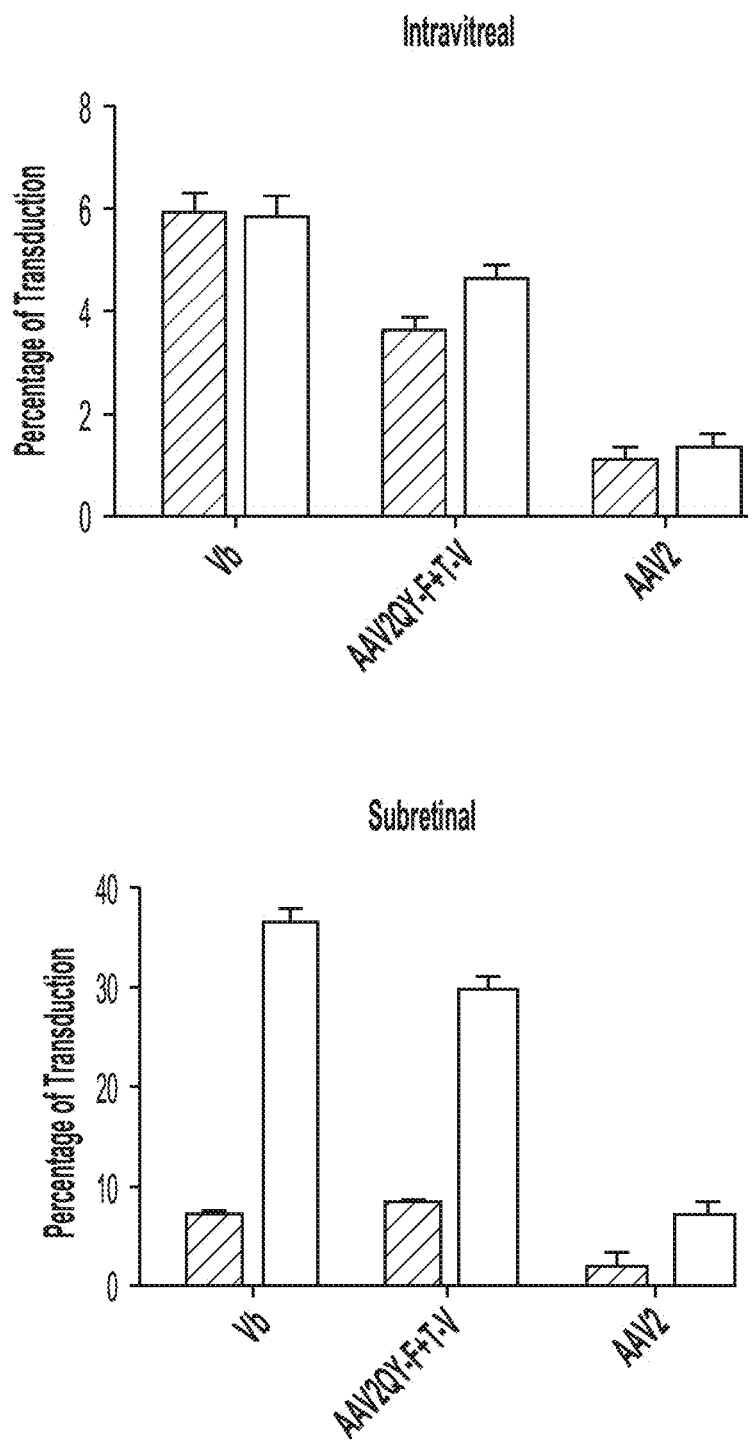

AAV2 variant Vb was found to be the second most prevalent in the mouse screen and the most prevalent in the macaque screen. FIGS. 8A-8C show the transduction profile of Vb after Nrl-GFP mice were injected intravitreally with 1 μl of $2e^{12}$ vg/ml of Sc-smCBA-mCherry packaged in a Vb variant AAV2 capsid. Three weeks after the injection, transduction was evaluated by funduscopy (see FIG. 8A) and FACS (see FIGS. 8B and 8C). Compared to the AAV2 (quadY-F+T-V), which has the mutations Y272F, Y444F, Y500F, Y730F and T491V, the AAV2 Vb variant particle carrying the gene for mCherry was able to transduce a higher number of retinal cells and with a higher expression per cell (FIG. 8A).

Four weeks after injection of the Vb variant AAV2 particles, the mice were sacrificed, and retinal cells dissociated and sorted for GFP expression and mCherry expression. The PE-Texas Red channel in the cytometer was used to detect mCherry expression. In FIG. 8B, the top right quadrant corresponds to the population of rod photoreceptors transduced by rAAV vector (GFP+ and mCherry+) and the bottom right quadrant corresponds to non-rod, neural retinal cells transduced by rAAV vector (mCherry+only).

FIG. 8C shows transduction rates for AAV2 variant Va when either administered to mice by intravitreal injection or subretinal injection. Mice were sacrificed 4 weeks after injection with the AAV2 variant particles. $2\times10^9$ vg was injected. The levels of transduction achieved in both rod PRs and non-rod, neural retinal cells after subretinal injection were comparable to those achieved with 2.5 times more of the wild-type AAV2 virus.

Example 6: Evaluation of Transduction Profiles of AAV2 Variant V2

Figure 9:
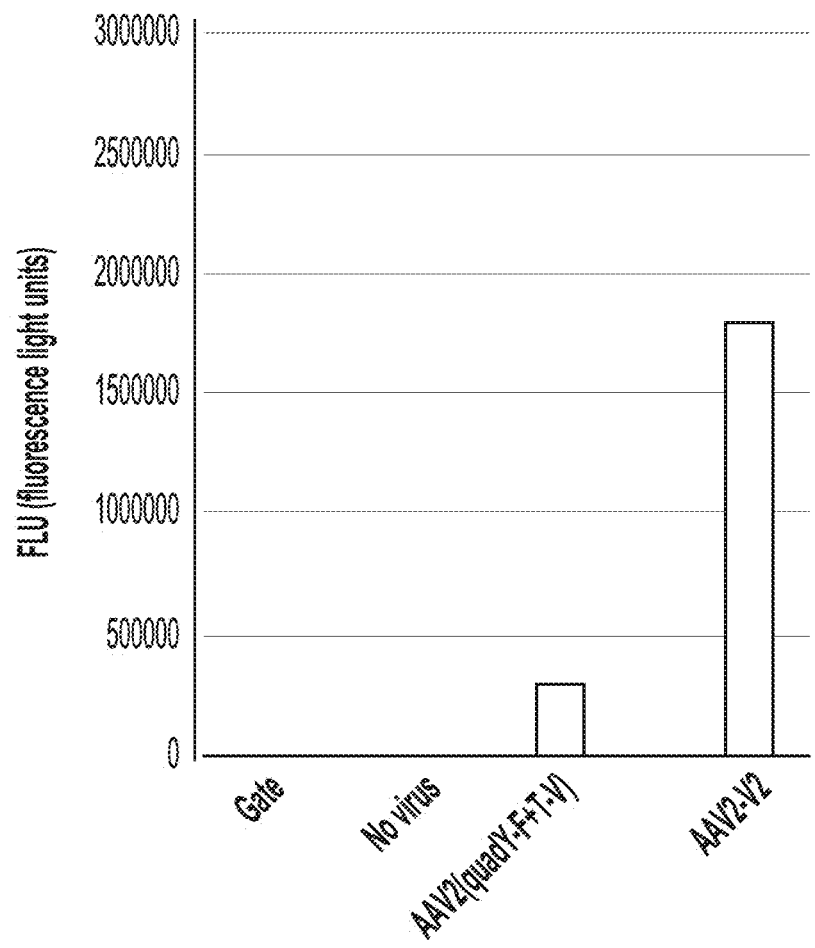
FIG. 9 shows transduction efficiency of AAV2-V2 variant in ARPE19 retinal epithelium cells. Cells were infected at a multiplicity of infection (MOI) of 10,000.

The transduction efficiency was measured in ARPE19 cells and the results can be seen in FIG. 9. Compared to AAV2(quadY-F+T-V) variant virus, AAV2-V2 variant virus was able to result in mCherry expression levels that were approximately 7 times higher.

Figure 10A:
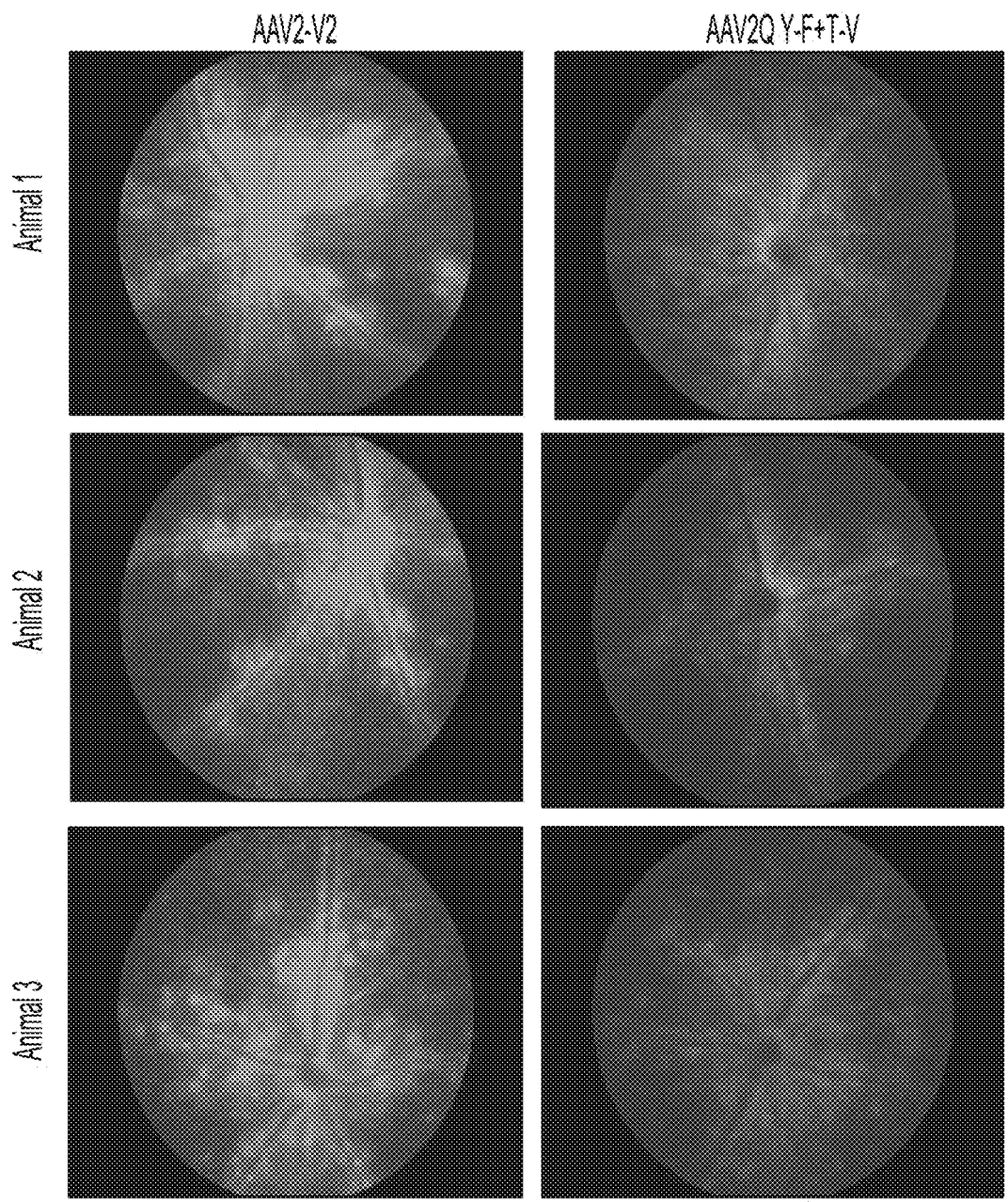
Figure 10C:
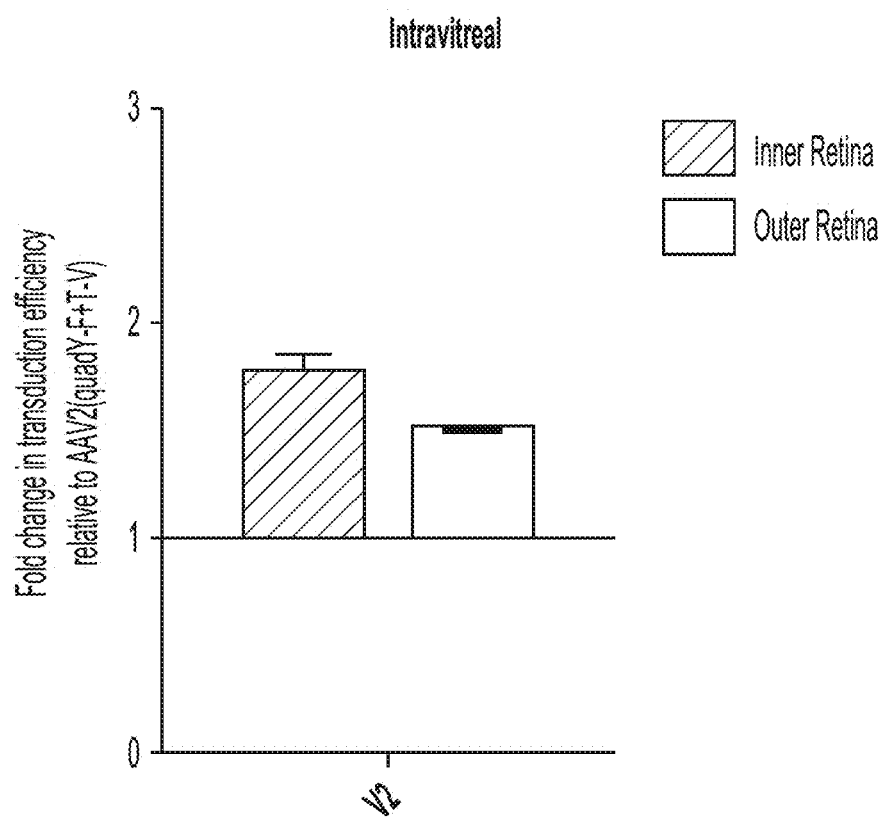

When tested in mice in a manner similar to how AAV2 variants Va and Vb, it was found that the transduction efficiency in mouse retina of AAV-V2 as observed by funduscopy was much higher compared to the control AAV2 (quadY-F+T-V) (FIG. 10A). A Characteristic FACs plot for retinal cells transduced with AAV2-V2 is shown in FIG. 10B. The transduction efficiency relative to AAV2(quadY-F+T-V) is shown in FIG. 10C. As can be seen, the AAV2-V2 variant outperforms the AAV2(quadY-F+T-V) variant virus.

Example 7: Evaluation of Transduction Profiles of AAV2 Variant V3

Figure 11:
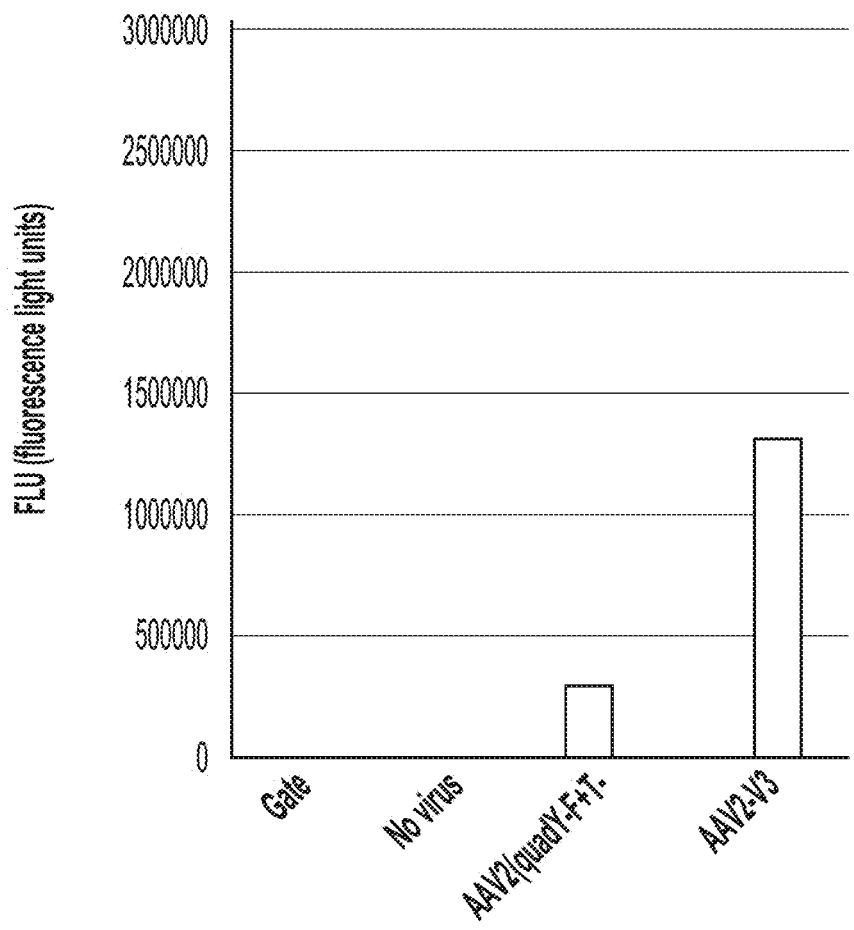
FIG. 11 shows transduction efficiency of AAV2-V3 in ARPE19 cells. Cells were infected at a multiplicity of infection (MOI) of 10,000.

The transduction efficiency was measured in ARPE19 cells and the results can be seen in FIG. 11. Compared to AAV2(quadY-F+T-V) variant virus, AAV2-V3 variant virus was able to result in mCherry expression levels that were approximately 5 times higher.

Figure 12A:
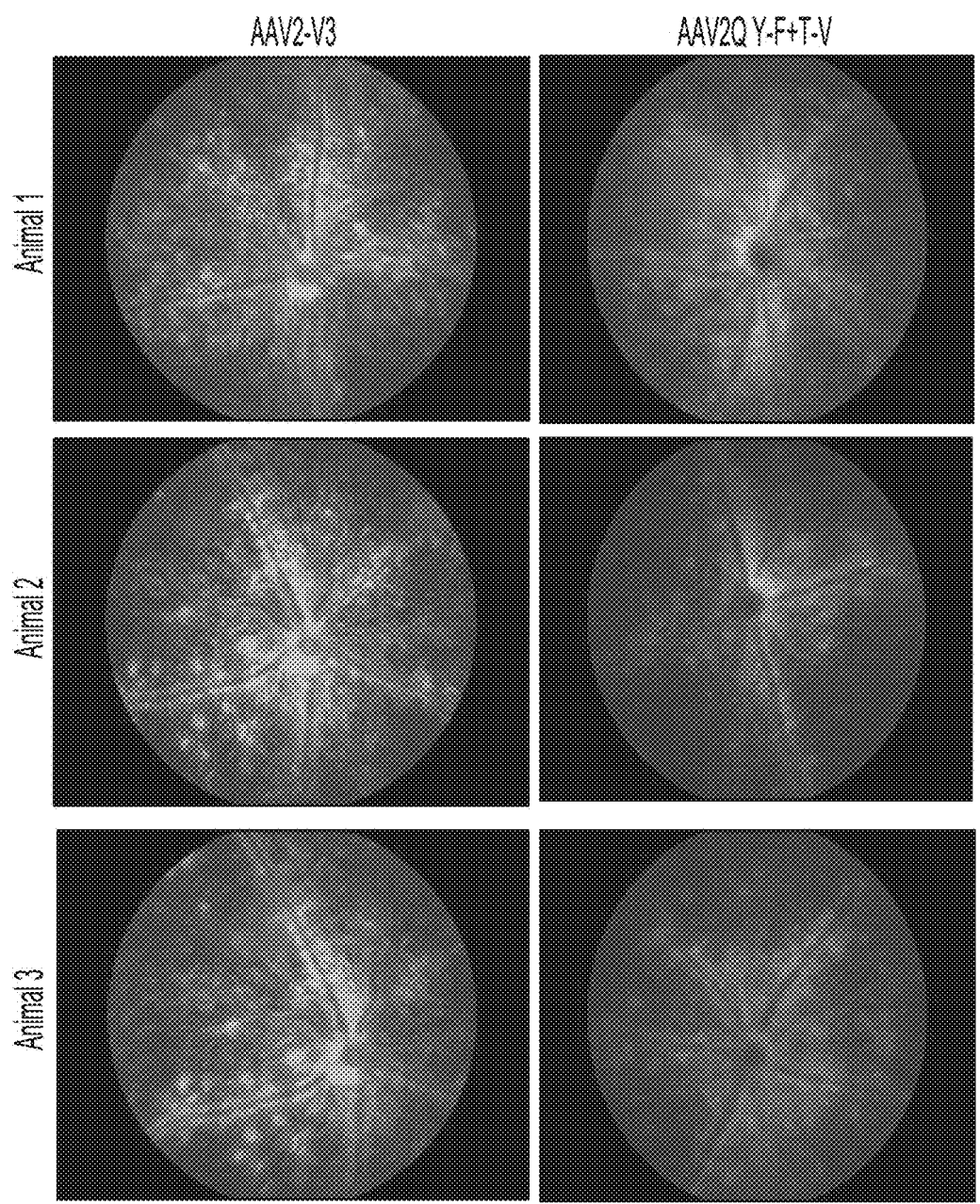
FIGS. 12A-12C show transduction efficiency for AAV2 variant V3.
Figure 12B:
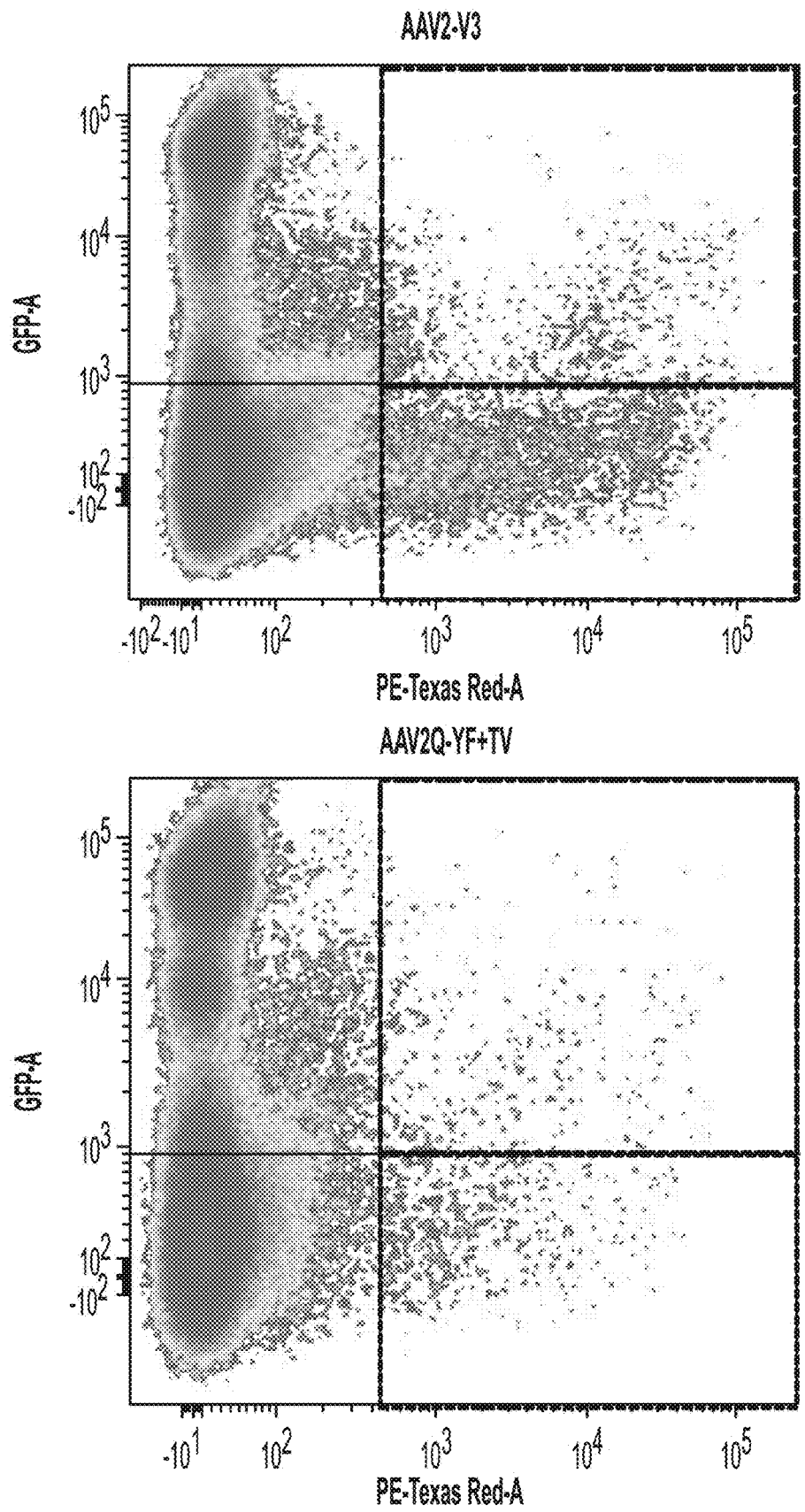
Figure 12C:
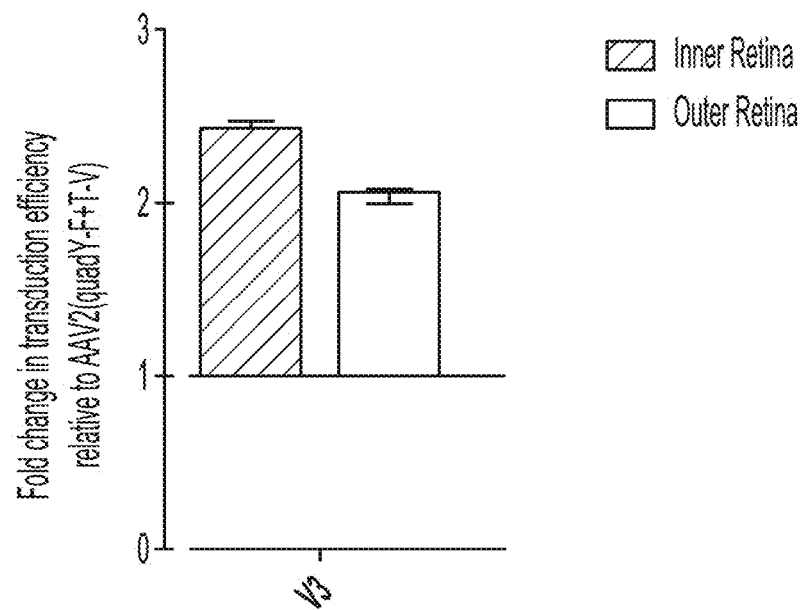

When tested in mice in a manner similar to how AAV2 variants Va, Vb and V2, it was found that the transduction efficiency in mouse retina of AAV2-V3 as observed by funduscopy was much higher compared to the control AAV2 (quadY-F+T−V) (FIG. 12A). A Characteristic FACs plot for retinal cells transduced with AAV2-V3 is shown in FIG. 12B. The transduction efficiency relative to AAV2(quadY-F+T−V) is shown in FIG. 12C. As can be seen, the AAV2-V3 variant outperforms the AAV2(quadY-F+T−V) variant virus.

Example 8: Rationally Designed Variants

Figure 13A:
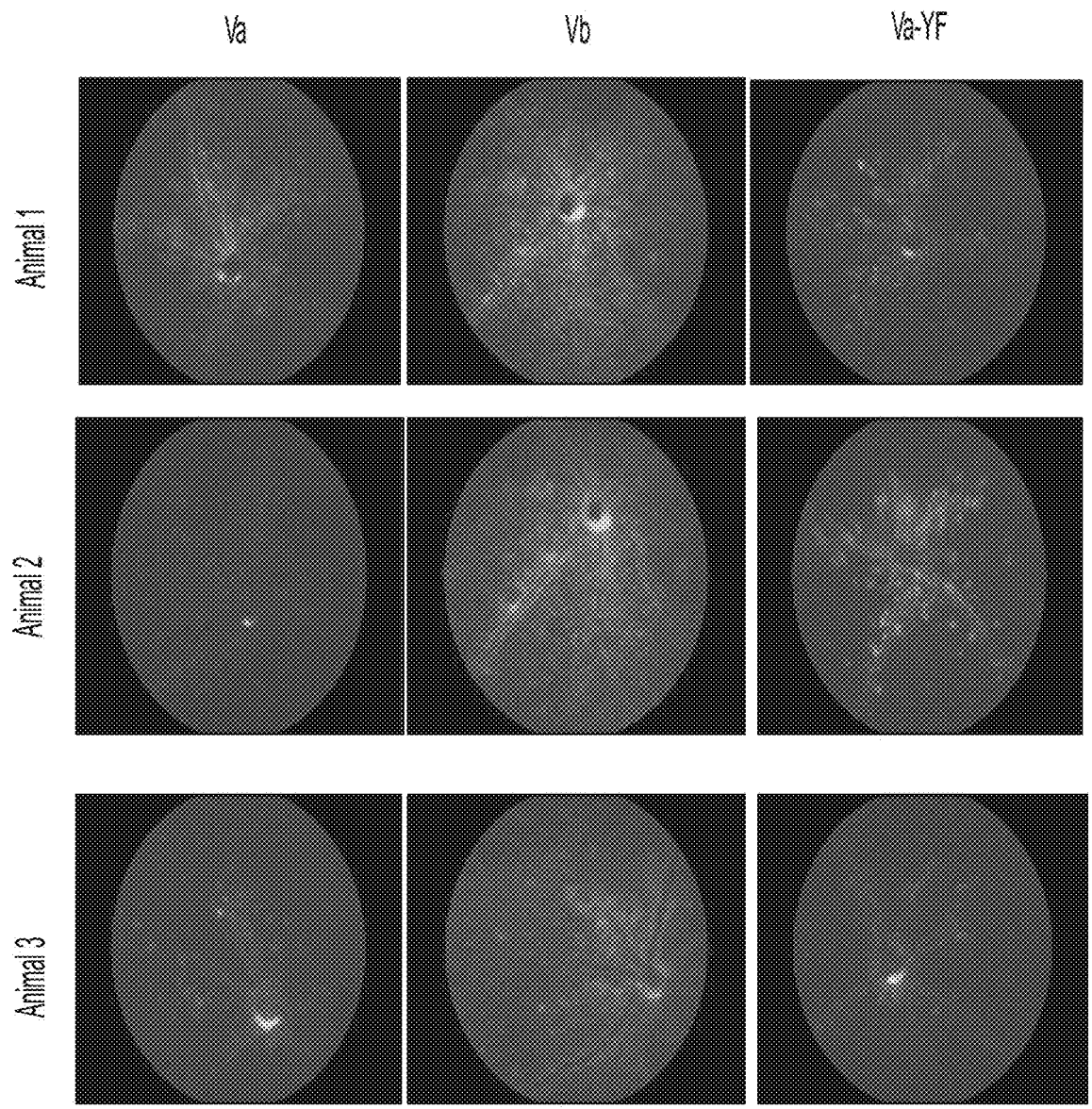
FIGS. 13A-13B show fundus images of retinas provided Va and Vb AAV2 capsid variants having additional T to F and/or T to V substitutions. YF represents Y444F and Y730F mutations; YF+TV represents Y272F, Y444F and Y730F, and T291V mutations.
Figure 13B:
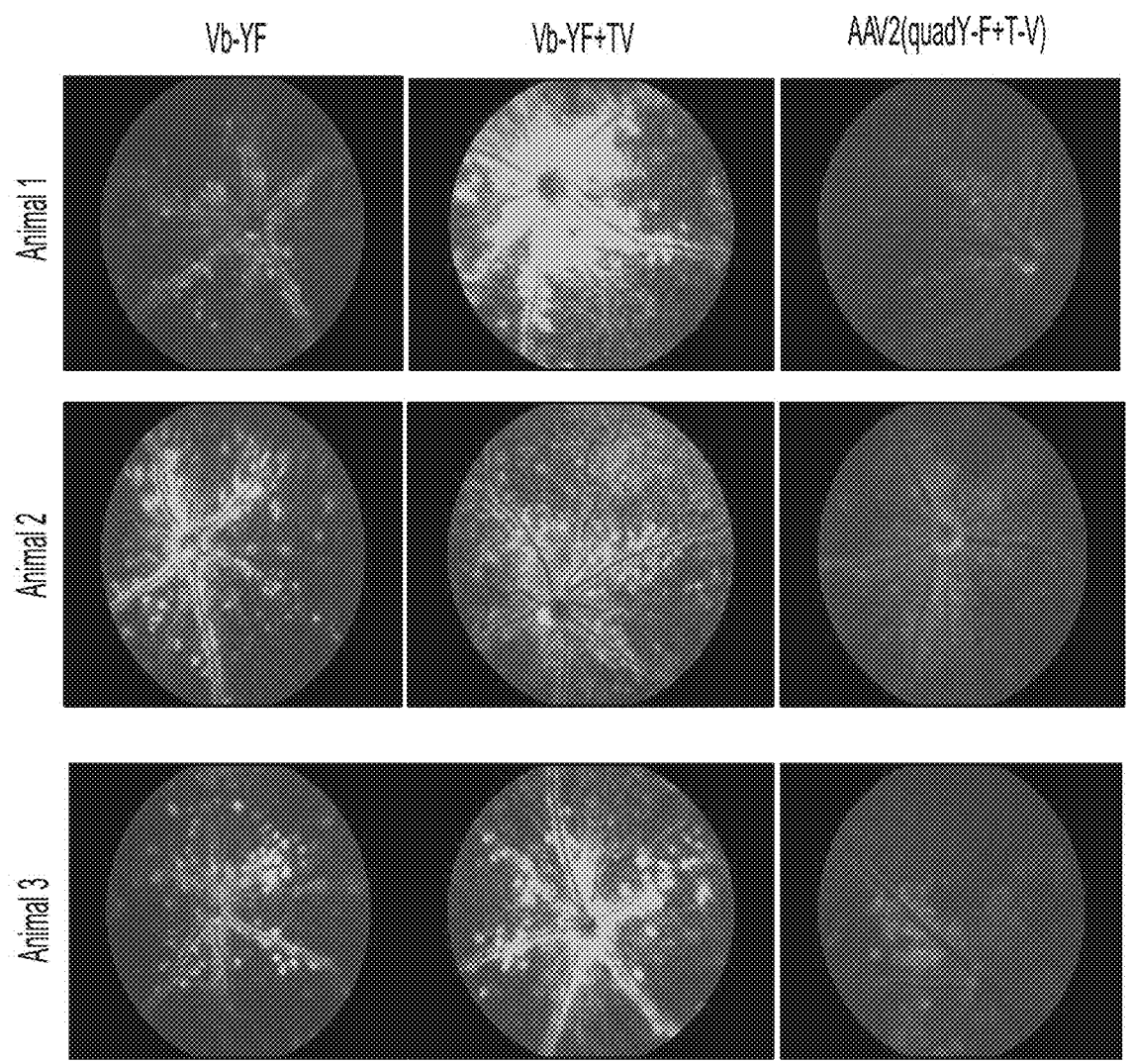
Figure 14:
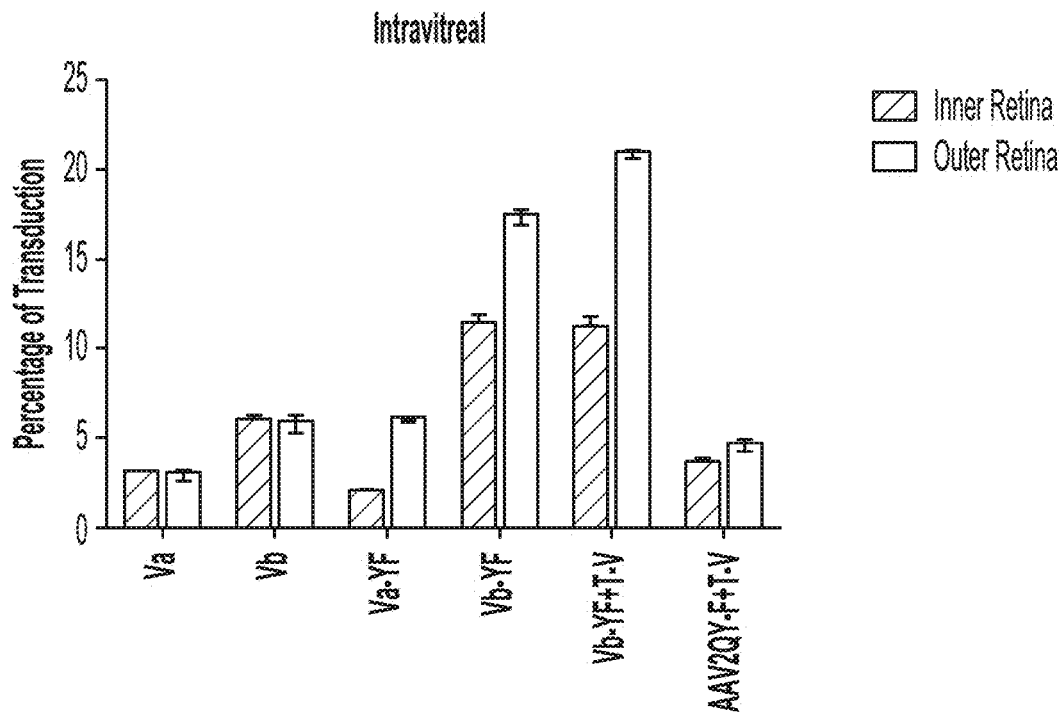
FIG. 14 shows quantification of FACS data illustrating transduction rates of Va and Vb AAV2 capsid variants having additional T to F and/or T to V substitutions as defined in FIG. 13B in Nrl-GFP mice.
Figure 15:
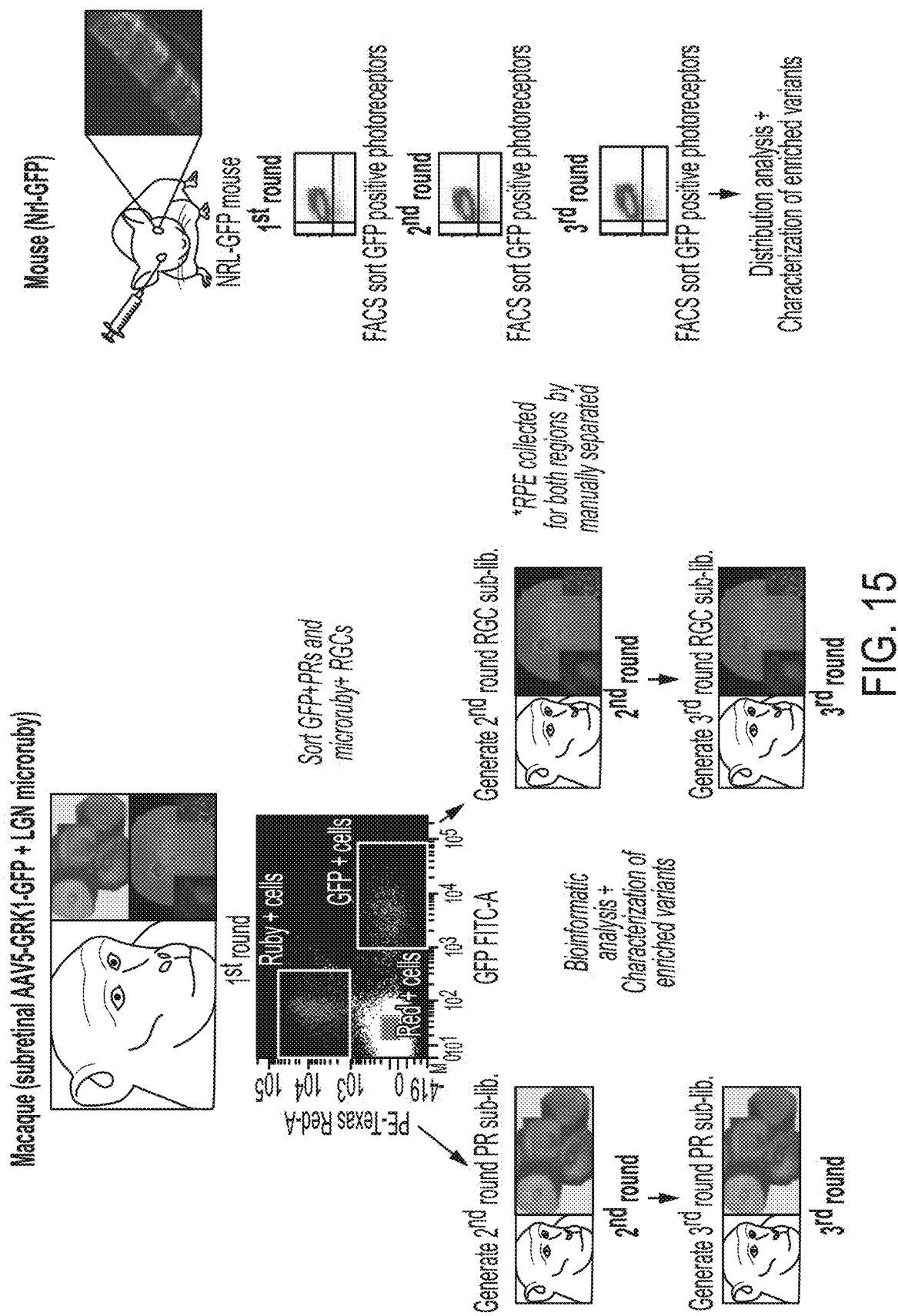
FIG. 15 shows the treatment procedure for Macaque (subretinal AAV5-GRK1-GFP+LGN microruby) and Mouse (Nrl-GFP).

Since it is known that certain mutations enhance the efficiency of AAV particles to transduce retinal cells, these mutations were superimposed onto the variants identified by the screening in mouse and macaque models to have greater retinal transduction capacity to further improve their performance. FIGS. 13A and 13B show transduction profiles using funduscopy of AAV2 variants Va and Vb having additional Y to F, and T to V substitutions. Va-YF represents a variant with the sequence of variant Va with additional phenylalanines at positions 444 and 730. Similarly, Vb-YF represents a variant with the sequence of variant Vb with additional phenylalanines at positions 444 and 730. AAV2 variant Vb-YF-TV represents a variant with the sequence of variant Vb with additional F at positions 272, 444 and 730, and a valine at position 491. It is clear from the fluorescence of mCherry in the fundus images that these substitutions greatly enhance the transduction efficiency (FIGS. 13A and 13B). Quantification of FACS data also shows that these additional mutations greatly improve the efficiency of the AAV2 capsid variants to transduce retinal cells (FIG. 14).

Example 9: Additional AAV Capsid Variants that Promote Efficient Transduction of Retina by Intravitreal Injection Adeno-associated virus (AAV) variants were isolated from a highly diverse AAV capsid library, CAPLIB-7, described in Example 1 by three rounds of in vivo selection performed in nonhuman primate (NHP). Selection initially involved creating an NHP with sortable photoreceptors (via subretinal injection of AAV5-GRK1-GFP) and retinal ganglion cells (via injection of a retrograde tracer dye into the lateral geniculate nucleus). Following creation of sortable cells, intravitreal injection of the capsid library into NHP was performed. This was followed by separate isolation of NHP photoreceptors (PR) and retinal ganglion cells (RGC), subsequent recovery of capsid variants individually from each cell type, and regeneration of separate PR and RGC sublibraries. Subsequent screens were then done in parallel with NHPs receiving RGC sub-library and RGCs being isolated and vice versa for PR sub-library. After the second round of selection in primate, a number of novel capsid variants were identified. When a subset of these variants was isolated and vectorized with a reporter construct they were shown to have increased transduction efficiencies in cell culture. When vectors were intravitreally injected into mice, transduction efficiencies were greatly improved over AAV2 and in most cases were better than quadYF+T−V. Subsequent to this a third round of screening in primate was performed and additional capsid variants were identified. These additional capsid variants are disclosed herein, many of which were not observed in the first two rounds of selection. The new capsid variants fall into 2 broad groups 1) Capsid variants that have increased their relative abundance in both PRs and RGCs from the 2nd to 3rd round of screening and 2) capsid variants that display a distributional bias towards either retinal ganglion cells (RGC) or photoreceptors (PR). Group 1 variants include P3-8, Vb, P3-3 and P3-4. Group 2 variants include P3-RGC1, P3-RGC2, and P3-RGC3 which displayed enrichment in primate retinal ganglion cells and low abundance in photoreceptors, and P3-PR1, P3-PR2, and P3-PR3 which conversely were substantially enriched in photoreceptors over retinal ganglion cells (FIGS. 24 and 25).

Example 10

The methodology for screening capsid libraries in primate retina was as follows. It relied on the ability to selectively "sort" retinal cells while maintaining the integrity of the nucleic acids contained within the cells, and was accomplished by expression of green fluorescent protein in photoreceptors via subretinal delivery of AAV5-GRK1-GFP and/or retrograde labeling of retinal ganglion cells (RGCs) by injection of fluorescent dye into the lateral geniculate nucleus (LGN).

Round 3 screening results were assessed and variants enriched in photoreceptors and RGCs were identified (FIGS. 24 and 25). Variants emerged with "biased" distribution between photoreceptors and RGCs.

Certain variants described herein were further enhanced by rational design. Va, Vb and V3 were modified to incorporate additional tyrosine to phenylalanine and threonine to valine mutations previously identified to enhance retinal transduction. Va (Y444+730F) was tested. Va (Y272+444+730F)+T491V was also created but packaged with poor efficiency (n=3). Vb (Y444+730F) and Vb (Y272+444+730F)+T491V were also tested. V3(Y272+500+730F)+T491V was also tested.

The transduction of mouse retina was characterized following Ivt injection. Capsid variants were vectorized to contain a self-complementary AAV with smCBA promoter driving mCherry. They were packaged at small scale, 2 cell stack, with iodixanol gradient purification. They were intravitreally injected at moderate dose, 2e9 vg in 1 μl into Nrl-GFP mice (N=6 or more for each variant). Transgene expression was evaluated 4 weeks post injection by funduscopy for mCherry fluorescence (in life) and by FACS of dissociated neural retina (RPE removed) to quantify the percentage of rod photoreceptor expressing mCherry (GFP-mCherry double positive cells). This is identical to published methodology for quantifying transduction efficiencies (Boye et al. J Virol. 2016 Mar. 28; 90(8):4215-31).

Capsid variants identified display substantially improved transduction of mouse retina following Ivt injection, relative to parent capsid AAV2. Rational design-guided mutagenesis further enhanced transduction in capsid variants Va and Vb. Five capsid variants outperform benchmark vectors. IHC indicates capsids variants display broad cell tropism.

TABLE 3

Figure 16:
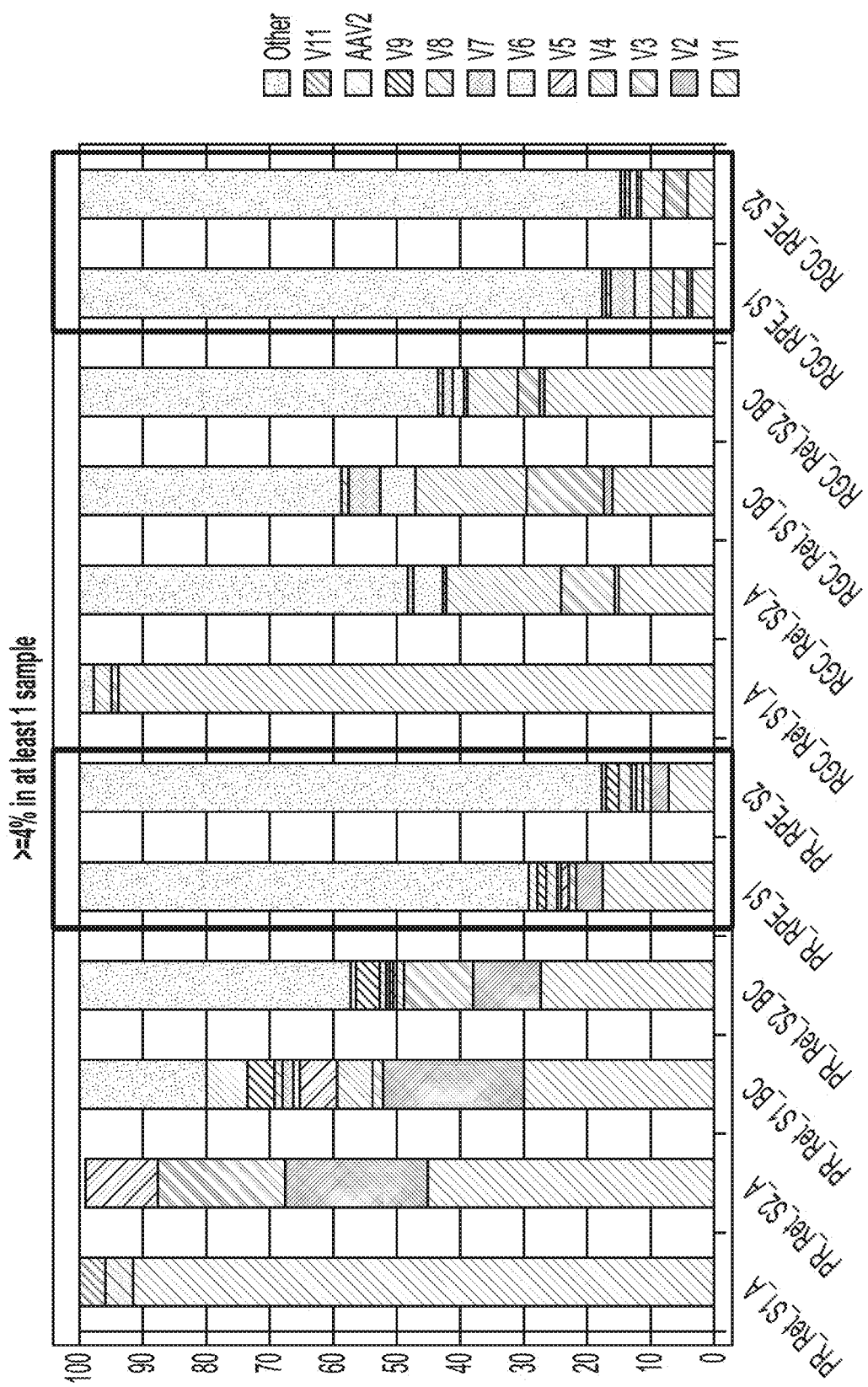
FIG. 16 shows the distribution of major variants within recovered tissues after 2 rounds of screening in primate. The X axis represents different cell typesand location within the retina. PR: photoreceptor; RGC: retinal ganglion cell: RPE: retinal pigment epithelium; A: central/macula; BC: peripheral retina.
Figures 17, 18:
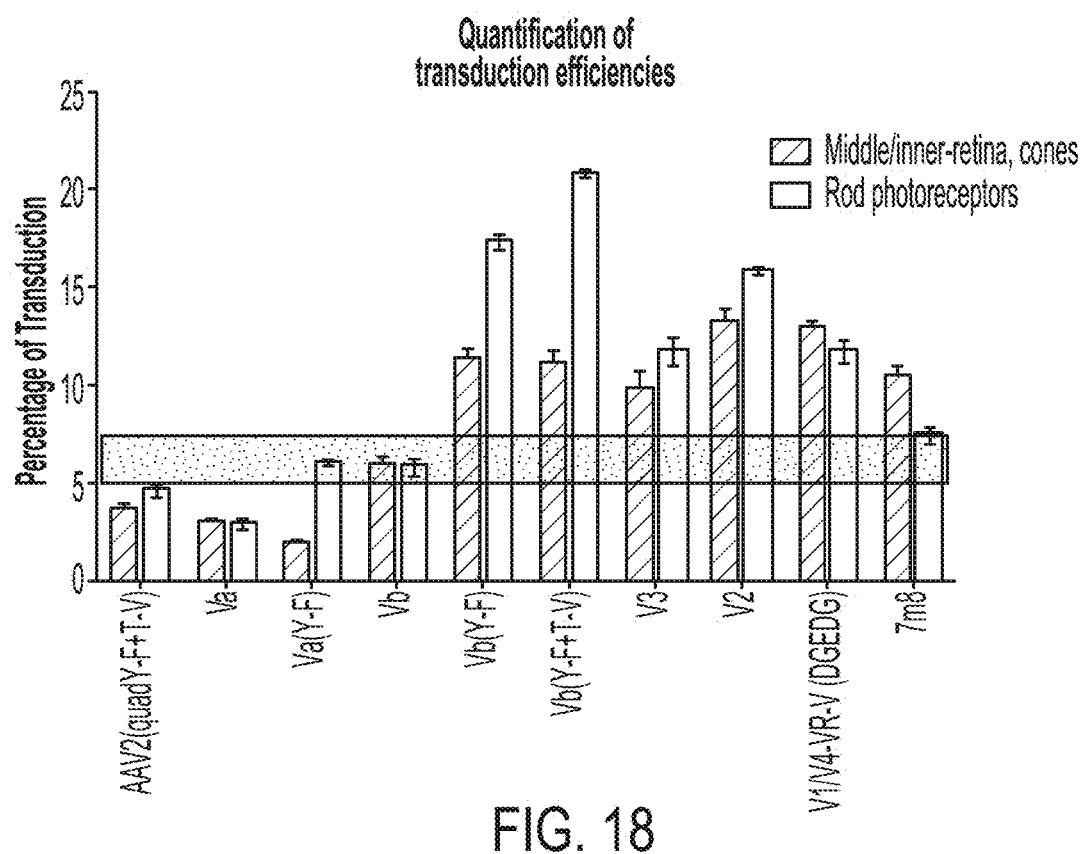
FIG. 17 shows major variants and the location substitutions by VR.
FIG. 18 shows quantification of transduction efficiencies. The bar represents the level of rod transduction exhibited by vectors AAV2(Y-F+T-V) and AAV-7m8
Figure 19:
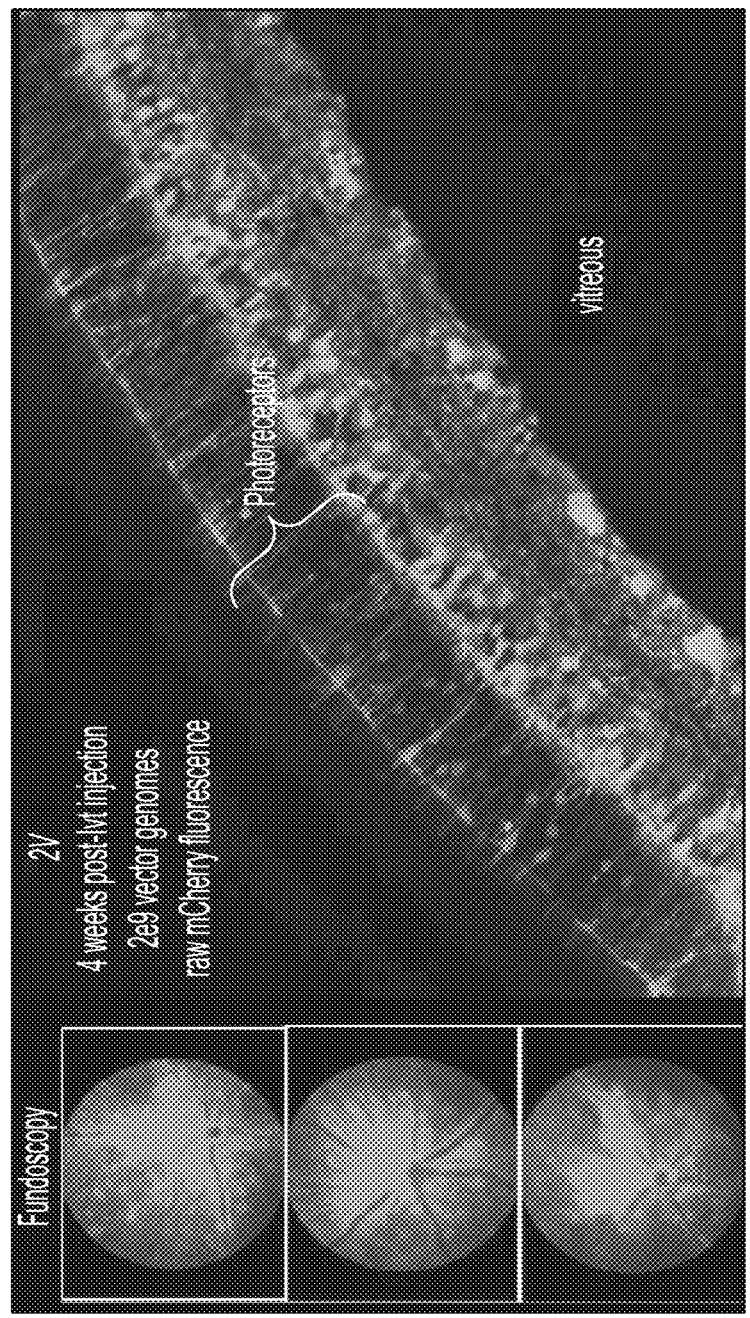
FIG. 19 shows fundoscopy and V2 4 weeks post Ivt injection with 2e9 vector genomes and raw mCherry fluorescence.

Capsid variants selected for transduction in primate retina using "barcoded" reporter construct. Results are shown in FIG. 16.

| Capsid variant | Type | Ivt rod transdxn/ AAV2(quadYF + T-V) |
|---|---|---|
| AAV2 | benchmark | 0.3×* |
| AAV2(trpYF) | benchmark | not tested |
| AAV2(quadYF + T-V) | benchmark | 1.0× |
| Va | Library | 0.6× |

TABLE 3-continued

Capsid variants selected for transduction in primate retina using "barcoded" reporter construct. Results are shown in FIG. 16.

| Capsid variant | Type | Ivt rod transdxn/ AAV2(quadYF + T-V) |
|---|---|---|
| Vb | Library | 1.5× |
| Vb(Y444 + 730F) | Library + rational des. | 3.5× |
| Vb(Y272 + 444 + 730F) + T491V | Library + rational des. | 4.4× |
| V2 | Library | 3.4× |
| V3 | Library | 2.6× |
| P3-RGC1 (P2-V6) | Library | 1.5× |
| P3-PR3 | Library | 1.6× |
| DGE-DF (AKA 'V1V4VR-V') | Library | 2.5× |
| AAV-7m8 | benchmark | 1.8× |

*Value based on previous experiments comparing AAV2 to other AAV2 capsid variants in the same mouse model and methodology, Boye et al. 2016 J. Virology.

Figure 20:
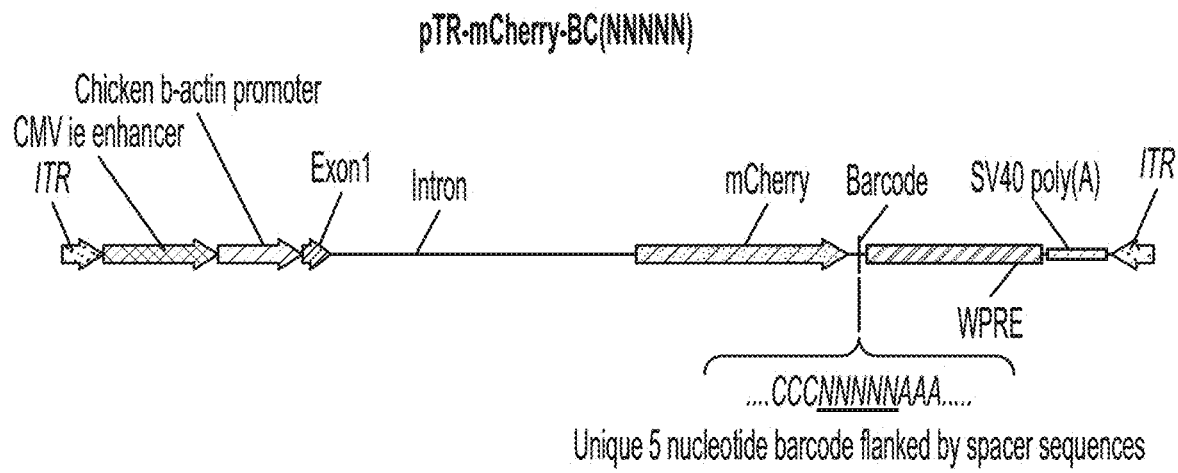
FIG. 20 shows the evaluation of relative transduction and transgene expression efficiencies of capsid variants in macaque and mouse retina utilizing barcoded vectors.

Relative transduction and transgene expression efficiencies of capsid variants in macaque and mouse retina were evaluated utilizing barcoded vectors. Methods are shown in FIGS. 15 to 19. Vector constructs with CBA promoter driving mCherry that were identical except for a unique 5 nucleotide "barcode" (FIG. 20) were packaged individually in the selected capsid variants. The location of the barcode allows identification of DNA (vector genome) and RNA (transgene expression) associated with each capsid variant following recovery from tissue/cells. Barcoded vectors were manufactured by triple transfection and purified by successive double iodixanol density gradients followed by ion-exchange chromatography (FPLC, Q-column). Vectors were assessed for: purity by protein gel, endotoxin by Endosafe PTS (Charles River), spec. less than 5 Eu/mL, full to empty ratio by electron microscopy, and spec. >50% full capsids. Several vectors were remade due to aggregation of capsids as observed on EM and by loss of genome titer following freeze thaw cycle. These vectors were put into a high salt buffer of BSS-tween supplemented with 150 mM NaCl. All vector preparations utilized in the barcoded pool passed specifications.

"Barcoded" vector pools: two "pooled" mixes were made: 1.OX mix, total concentration of 3e12 vg/ml, with each variant at approx. 2.3e11 vg/ml, and 0.1X mix, total concentration of 3e11 vg/ml, with each variant at approx. 2.3e10 vg/ml. Both barcoded vector pools diluted into BSS tween buffer. 1.OX pool was calculated to be 398 mOsm vs 300 mOsm physiologic due to the inclusion of vector preps eluted in high salt. It was noted that significant dilution of vector occurred upon Ivt injection. Pools were created separately (i.e., 0.1X pool is not a 1:10 dilution of the 1.OX pool).

Barcoded experimental plan for NHPs: two *M. fascicularis* (cynomolgus monkey) had RGCs labeled for isolation by FACS. They received a single 100 μl intravitreal injection of barcoded pool. One eye received 1.OX pool, the other eye 0.1X pool. 3 weeks after Ivt injection of barcoded vectors, they received LGN injection of "green" dye, and were sacrificed 1 week later (4 weeks following barcoded vector injection). Two NHPs had PRs were labeled for isolation by FACS. Multiple subretinal blebs of AAV5-GRK1-GFP labelled photoreceptors. Three days later, they received 100 μl Ivt injection of barcoded pool (same as above). Six weeks after Ivt injection of barcoded vectors, the animals were sacrificed. The sacrifice was originally scheduled for 4 weeks following Ivt of barcode but was delayed by approximately a week and a half. All NHPs pre-screened for anti-AAV2 NAb. Selected animals appeared naïve.

TABLE 4

NHP information.

| Animal # (and name/ID) | cell type labeled | Right eye | Left eye | DOB (approx age) |
|---|---|---|---|---|
| 1 (Joseph/AH568L) | RGCs | 1.0× barcode | 0.1× barcode | Dec. 23, 2013 (3.7 yrs) |
| 2 (Gus-Gus/BB328F) | RGCs | 1.0× barcode | 0.1× barcode | Mar. 17, 2010 (7.5 yrs) |
| 3 (Rasheed/MR88G) | Photoreceptors | 0.1× barcode | 1.0× barcode | Mar. 8, 2008 (9.5 yrs) |
| 4 (Sid/GB3X) | Photoreceptors | 1.0× barcode | 0.1× barcode | Aug. 2, 2010 (7.0 yrs) |

Figure 21:
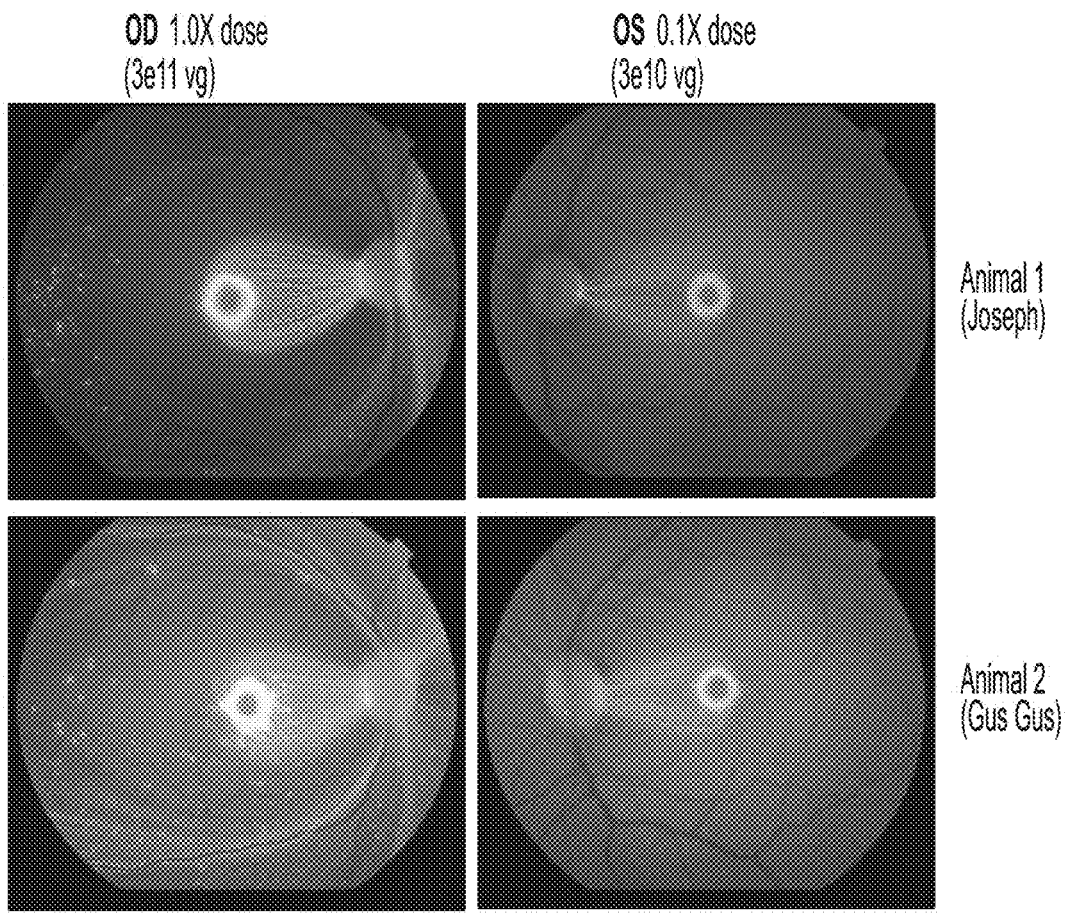
FIG. 21 shows RGC labeled animals (1 and 2) at 2 weeks post Ivt injection of barcoded vectors.
Figure 22:
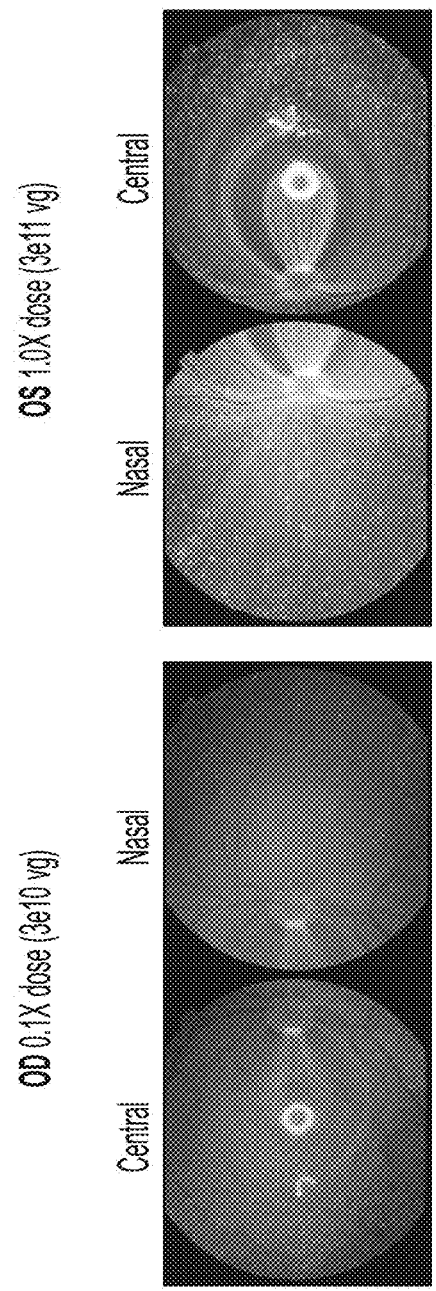
FIG. 22 shows PR labeled animal 3 at 20 days post Ivt barcoded vectors. Enhanced transduction of barcoded vectors evident proximal to the retinotomy for the submacular injection of AAV5-GFP. mCherry expression present in the periphery outside the field of view in the OD and OS.
Figure 23:
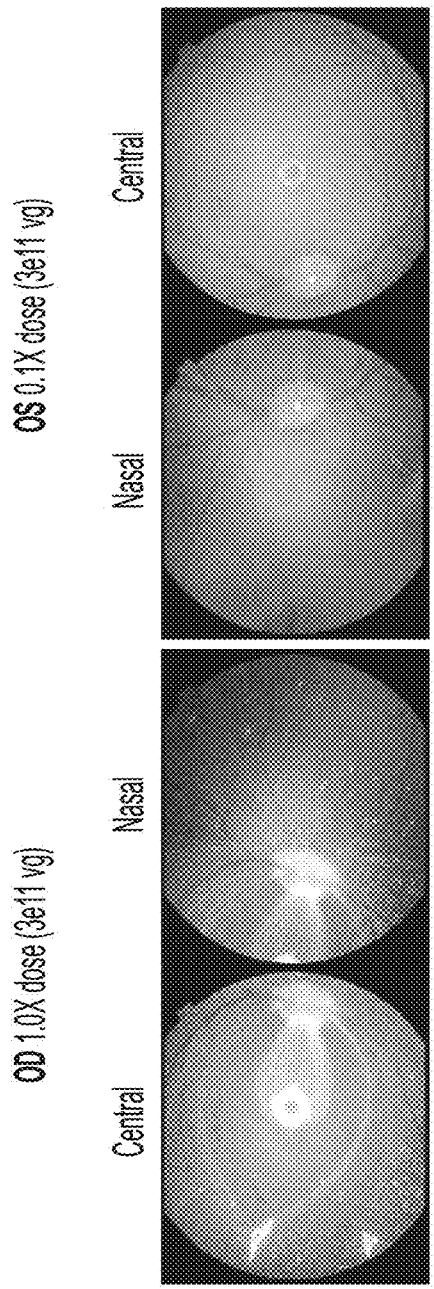
FIG. 23 shows PR labeled animal 4 at 20 days post Ivt barcoded vectors. Enhanced transduction of barcoded vectors is evident proximal to the retinotomy for the submacular injection of AAV5-GFP. mCherry expression is present in the periphery outside the field of view in the OD.

RGC labeled animals were imaged as follows: 1 week pre-injection, color fundus only, 2 days post Ivt injection of barcode, color fundus only, 2 and 3 weeks post Ivt barcode, color fundus+ mCherry fluorescence, 4 weeks post Ivt barcode and 6-7 days post LGN injection of tracer, FITC+ mCherry fluorescence. PR labeled animals imaged: 4 days pre subretinal injection of AAV5-GFP (PR labeling), 9 days post subretinal AAV5-GFP, color fundus only, 23 days post subretinal AAV5-GFP and 20 days post Ivt barcode, color fundus+ FITC+ mCherry fluorescence 4 and 5 weeks post subretinal AAV5-GFP and Ivt barcode, color fundus+ FITC+ mCherry fluorescence, 6 weeks post subretinal AAV5-GFP and Ivt barcode, FITC+ mCherry fluorescence. The results of the imaging are shown in FIGS. 21, 22, and 23.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

That which is claimed is:

1. A variant recombinant adeno-associated virus (rAAV) capsid protein comprising a peptide inserted into the capsid protein between positions 585 and 588 of AAV2 VP1 capsid protein and comprising any one of the following combinations of amino acid substitutions selected from:
   a) aspartic acid, glycine, glutamic acid, aspartic acid, phenylalanine, at positions corresponding to amino acids 492, 493, 494, 499 and 500 of AAV2 VP1 capsid protein, respectively;
   b) asparagine, alanine, aspartic acid, glycine, glutamic acid, aspartic acid, and phenylalanine at positions corresponding to amino acids 263, 264, 492, 493, 494, 499, and 500 of AAV2 VP1 capsid protein, respectively, and SAAGADXAXDS (SEQ ID NO: 5) at positions corresponding to amino acids 546-556 of AAV2 VP1 capsid protein, wherein X is any amino acid;
   c) alanine, threonine, proline, aspartic acid, phenylalanine, and aspartic acid at positions corresponding to amino acids 263, 490, 492, 499, 500, and 530 of AAV2 VP1 capsid protein, respectively;
   d) asparagine, alanine, phenylalanine, alanine, asparagine, valine, threonine, arginine, aspartic acid, and aspartic acid at positions corresponding to amino acids 263, 264, 444, 451, 454, 455, 459, 527, 530, and 531 of AAV2 VP1 capsid protein, respectively; and
   e) aspartic acid, glycine, glutamic acid, aspartic acid, and phenylalanine at positions corresponding to amino acids 492, 493, 494, 499, and 500 of AAV2 VP1 capsid protein, respectively, and EDATENXIXXDR (SEQ ID NO: 4) at positions corresponding to amino acids 545-556 of AAV2 VP1 capsid protein, wherein X is any amino acid.

2. The rAAV capsid protein of claim 1, wherein the amino acid substitutions comprise (a) aspartic acid, glycine, glutamic acid, aspartic acid, phenylalanine, at positions corresponding to amino acids 492, 493, 494, 499 and 500 of AAV2 VP1 capsid protein, respectively.

3. The rAAV capsid protein of claim 1, wherein the amino acid substitutions comprise (b) asparagine, alanine, aspartic acid, glycine, glutamic acid, aspartic acid, and phenylalanine at positions corresponding to amino acids 263, 264, 492, 493, 494, 499, and 500 of AAV2 VP1 capsid protein, respectively, and SAAGADXAXDS (SEQ ID NO: 5) at positions corresponding to amino acids 546-556 of AAV2 VP1 capsid protein, wherein X is any amino acid.

4. The rAAV capsid protein of claim 1, wherein the amino acid substitutions comprise (c) alanine, threonine, proline, aspartic acid, phenylalanine, and aspartic acid at positions corresponding to amino acids 263, 490, 492, 499, 500, and 530 of AAV2 VP1 capsid protein, respectively.

5. The rAAV capsid protein of claim 1, wherein the amino acid substitutions comprise (d) asparagine, alanine, phenylalanine, alanine, asparagine, valine, threonine, arginine, aspartic acid, and aspartic acid at positions corresponding to amino acids 263, 264, 444, 451, 454, 455, 459, 527, 530, and 531 of AAV2 VP1 capsid protein, respectively.

6. The rAAV capsid protein of claim 1, wherein the amino acid substitutions comprise (e) aspartic acid, glycine, glutamic acid, aspartic acid, and phenylalanine at positions corresponding to amino acids 492, 493, 494, 499, and 500 of AAV2 VP1 capsid protein, respectively, and EDATENXIXXDR (SEQ ID NO: 4) at positions corresponding to amino acids 545-556 of AAV2 VP1 capsid protein, wherein X is any amino acid.

7. The rAAV capsid protein of claim 1, wherein the peptide is inserted into the capsid protein between position 587 and 588 of AAV2 VP1 capsid protein.

8. The rAAV capsid protein of claim 1, wherein the peptide comprises a transduction efficiency-enhancing peptide of about 6 to about 8 amino acids in length.

9. The rAAV capsid protein of claim 1, wherein the peptide is selected from the group consisting of LALGETTRPA (SEQ ID NO: 66), NRGTEWD (SEQ ID NO: 67), ADGVQWT (SEQ ID NO: 68), GEARISA (SEQ ID NO: 69), SGNSGAA (SEQ ID NO: 70), ESGLSQS (SEQ ID NO: 71), EYRDSSG (SEQ ID NO: 72), DLGSARA (SEQ ID NO: 73), PRSADLA (SEQ ID NO: 74), PRSTSDP (SEQ ID NO: 75), and ESGHGYF (SEQ ID NO: 76).

10. A variant rAAV capsid protein of a serotype other than serotype 2 comprising any one of the combinations of amino acid substitutions in accordance with claim/3, wherein the substitutions are at positions homologous to the amino acids of a wild-type AAV2 VP1 capsid sequence as set forth in SEQ ID NO: 1.

11. The variant rAAV capsid protein of a serotype other than serotype 2 of claim 10, wherein the capsid protein is of serotype 1, 3, 3B, 4, 5, 6, 7, 8, 9, 10, 11, 12, or 13.

12. A recombinant AAV (rAAV) particle comprising the rAAV capsid protein of claim 1.

13. The rAAV particle of claim 12, wherein the particle is an AAV2 particle.

14. The rAAV particle of claim 13 further comprising a nucleic acid comprising inverted terminal repeats (ITRs) and a gene of interest.

15. The rAAV particle of claim 13, wherein the nucleic acid is single stranded.

16. The rAAV particle of claim 14, wherein the nucleic acid is double-stranded.

17. A composition comprising a plurality of the AAV2 particle of claim 13.

18. The rAAV capsid protein of claim 3, wherein the amino acid substitutions comprise (b) asparagine, alanine, aspartic acid, glycine, glutamic acid, aspartic acid, and phenylalanine at positions corresponding to amino acids 263, 264, 492, 493, 494, 499, and 500 of AAV2 VP1 capsid protein, respectively, and SAAGADXAXDS (SEQ ID NO: 5) at positions corresponding to amino acids 546-556 of AAV2 VP1 capsid protein, wherein the first X comprises a valine, and the second X comprises an isoleucine.

19. The rAAV capsid protein of claim 6, wherein the amino acid substitutions comprise (e) aspartic acid, glycine, glutamic acid, aspartic acid, and phenylalanine at positions corresponding to amino acids 492, 493, 494, 499, and 500 of AAV2 VP1 capsid protein, respectively, and EDATENXIXXDR (SEQ ID NO: 4) at positions corresponding to amino acids 545-556 of AAV2 VP1 capsid protein, wherein the first X comprises an asparagine, the second comprises an aspartic acid, and the third X comprises an isoleucine.

* * * * *

UNITED STATES PATENT AND TRADEMARK OFFICE
CERTIFICATE OF CORRECTION

PATENT NO. : 11,767,346 B2
APPLICATION NO. : 17/689324
DATED : September 26, 2023
INVENTOR(S) : Sergei Zolotukhin et al.

It is certified that error appears in the above-identified patent and that said Letters Patent is hereby corrected as shown below:

In the Claims

In Claim 10, Column 117, Line 14, the text "claim/3" should read --claim 1--

Signed and Sealed this
Twenty-first Day of November, 2023

Katherine Kelly Vidal
Director of the United States Patent and Trademark Office

SEQUENCE LISTING

<160> NUMBER OF SEQ ID NOS: 78

<210> SEQ ID NO 1
<211> LENGTH: 735

<212> TYPE: PRT
<213> ORGANISM: Unknown
<220> FEATURE:
<223> OTHER INFORMATION: adeno-associated virus 2

<400> SEQUENCE: 1

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380
```

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 2
<211> LENGTH: 598
<212> TYPE: PRT
<213> ORGANISM: Unknown
<220> FEATURE:
<223> OTHER INFORMATION: adeno-associated virus 2

<400> SEQUENCE: 2

Met Ala Pro Gly Lys Lys Arg Pro Val Glu His Ser Pro Val Glu Pro
1               5                   10                  15
```

-continued

```
Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
```

|  | 435 |  |  |  | 440 |  |  |  | 445 |  |  |
|---|---|---|---|---|---|---|---|---|---|---|---|

Gly Asn Arg Gln Ala Ala Thr Ala Asp Val Asn Thr Gln Gly Val Leu
    450                    455                  460

Pro Gly Met Val Trp Gln Asp Arg Asp Val Tyr Leu Gln Gly Pro Ile
465                    470                    475                  480

Trp Ala Lys Ile Pro His Thr Asp Gly His Phe His Pro Ser Pro Leu
                485                    490                    495

Met Gly Gly Phe Gly Leu Lys His Pro Pro Gln Ile Leu Ile Lys
        500                    505                510

Asn Thr Pro Val Pro Ala Asn Pro Ser Thr Thr Phe Ser Ala Ala Lys
    515                    520                  525

Phe Ala Ser Phe Ile Thr Gln Tyr Ser Thr Gly Gln Val Ser Val Glu
530                    535                    540

Ile Glu Trp Glu Leu Gln Lys Glu Asn Ser Lys Arg Trp Asn Pro Glu
                545                  550                555                  560

Ile Gln Tyr Thr Ser Asn Tyr Asn Lys Ser Val Asn Val Asp Phe Thr
                    565                    570                  575

Val Asp Thr Asn Gly Val Tyr Ser Glu Pro Arg Pro Ile Gly Thr Arg
        580                    585                    590

Tyr Leu Thr Arg Asn Leu
    595

<210> SEQ ID NO 3
<211> LENGTH: 533
<212> TYPE: PRT
<213> ORGANISM: Unknown
<220> FEATURE:
<223> OTHER INFORMATION: adeno-associated virus 2

<400> SEQUENCE: 3

Met Ala Thr Gly Ser Gly Ala Pro Met Ala Asp Asn Asn Glu Gly Ala
1                  5                    10                  15

Asp Gly Val Gly Asn Ser Ser Gly Asn Trp His Cys Asp Ser Thr Trp
                20                    25                    30

Met Gly Asp Arg Val Ile Thr Thr Ser Thr Arg Thr Trp Ala Leu Pro
        35                    40                    45

Thr Tyr Asn Asn His Leu Tyr Lys Gln Ile Ser Ser Gln Ser Gly Ala
    50                    55                    60

Ser Asn Asp Asn His Tyr Phe Gly Tyr Ser Thr Pro Trp Gly Tyr Phe
65                    70                    75                  80

Asp Phe Asn Arg Phe His Cys His Phe Ser Pro Arg Asp Trp Gln Arg
                85                    90                    95

Leu Ile Asn Asn Asn Trp Gly Phe Arg Pro Lys Arg Leu Asn Phe Lys
        100                    105                110

Leu Phe Asn Ile Gln Val Lys Glu Val Thr Gln Asn Asp Gly Thr Thr
    115                    120                  125

Thr Ile Ala Asn Asn Leu Thr Ser Thr Val Gln Val Phe Thr Asp Ser
130                    135                    140

Glu Tyr Gln Leu Pro Tyr Val Leu Gly Ser Ala His Gln Gly Cys Leu
145                    150                    155                  160

Pro Pro Phe Pro Ala Asp Val Phe Met Val Pro Gln Tyr Gly Tyr Leu
                    165                    170                175

Thr Leu Asn Asn Gly Ser Gln Ala Val Gly Arg Ser Ser Phe Tyr Cys
                180                    185                    190

Leu Glu Tyr Phe Pro Ser Gln Met Leu Arg Thr Gly Asn Asn Phe Thr

```
                    195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Gln Ser
                245                 250                 255

Arg Leu Gln Phe Ser Gln Ala Gly Ala Ser Asp Ile Arg Asp Gln Ser
                260                 265                 270

Arg Asn Trp Leu Pro Gly Pro Cys Tyr Arg Gln Gln Arg Val Ser Lys
                275                 280                 285

Thr Ser Ala Asp Asn Asn Ser Glu Tyr Ser Trp Thr Gly Ala Thr
    290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
                340                 345                 350

Glu Lys Val Met Ile Thr Asp Glu Glu Ile Arg Thr Thr Asn Pro
    355                 360                 365

Val Ala Thr Glu Gln Tyr Gly Ser Val Ser Thr Asn Leu Gln Arg Gly
    370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
                420                 425                 430

Gly Gly Phe Gly Leu Lys His Pro Pro Pro Gln Ile Leu Ile Lys Asn
                435                 440                 445

Thr Pro Val Pro Ala Asn Pro Ser Thr Thr Phe Ser Ala Ala Lys Phe
    450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
                500                 505                 510

Asp Thr Asn Gly Val Tyr Ser Glu Pro Arg Pro Ile Gly Thr Arg Tyr
    515                 520                 525

Leu Thr Arg Asn Leu
    530

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
```

```
<223> OTHER INFORMATION: Xaa can be any naturally occurring amino acid

<400> SEQUENCE: 4

Glu Asp Ala Thr Glu Asn Xaa Ile Xaa Xaa Asp Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 5

Ser Ala Ala Gly Ala Asp Xaa Ala Xaa Asp Ser
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (9)..(10)
<223> OTHER INFORMATION: Xaa can be any naturally occurring amino acid

<400> SEQUENCE: 6

Ser Gly Arg Glu Gly Asp Ala Glu Xaa Xaa Asp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 7

Asp Glu Ala Xaa Ser Glu Xaa Lys Xaa Thr Xaa Arg
1               5                   10

<210> SEQ ID NO 8
<211> LENGTH: 5
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 8

Arg Xaa Xaa Asp Asp
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 9

Gln Asp Xaa Glu
1

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 10

Ala Ala Ala Asp Asp Xaa Glu Xaa Asp Gly
1               5                   10

<210> SEQ ID NO 11
<211> LENGTH: 294
<212> TYPE: PRT
<213> ORGANISM: Artificial Sequence
<220> FEATURE:
<223> OTHER INFORMATION: Synthetic Polynucleotide

<400> SEQUENCE: 11

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
```

```
              100                 105                 110
Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
        130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
210                 215                 220

Arg Val Ser Lys Thr Asp Gly Glu Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Glu Asp Ala Thr Glu Asn
        275                 280                 285

Asn Ile Asp Ile Asp Arg
    290

<210> SEQ ID NO 12
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 12

Asn Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
        35                  40                  45

Leu Asn Phe Lys Leu Phe Asn Ile Gln Val Lys Glu Val Thr Gln Asn
50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
```

```
                    165                 170                 175
Asp Gln Tyr Leu Tyr Tyr Leu Ser Arg Thr Asn Thr Pro Ser Gly Thr
                180                 185                 190

Thr Thr Gln Ser Arg Leu Gln Phe Ser Gln Ala Gly Ala Ser Asp Ile
            195                 200                 205

Arg Asp Gln Ser Arg Asn Trp Leu Pro Gly Pro Cys Tyr Arg Gln Gln
        210                 215                 220

Arg Val Ser Lys Thr Asp Gly Glu Asn Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Gln Ser Ala Ala Gly Ala
        275                 280                 285

Asp Ile Ala Ile Asp Ser
    290
```

<210> SEQ ID NO 13
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 13

```
Asn Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Asn Trp Gly Phe Arg Pro Lys Arg
            35                  40                  45

Leu Asn Phe Lys Leu Phe Asn Ile Gln Val Lys Glu Val Thr Gln Asn
        50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Thr Asp Gly Glu Asn Asn Asn Ser Asp Phe Ser Trp
```

```
                225                 230                 235                 240
Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
                260                 265                 270

Pro Gln Ser Gly Val Leu Ile Phe Gly Lys Glu Asp Ala Thr Glu Asn
                275                 280                 285

Asn Ile Asp Ile Asp Arg
                290

<210> SEQ ID NO 14
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 14

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Asn Trp Gly Phe Arg Pro Lys Arg
                35                  40                  45

Leu Asn Phe Lys Leu Phe Asn Ile Gln Val Lys Glu Val Thr Gln Asn
                50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
                100                 105                 110

Tyr Gly Tyr Leu Thr Leu Asn Asn Gly Ser Gln Ala Val Gly Arg Ser
                115                 120                 125

Ser Phe Tyr Cys Leu Glu Tyr Phe Pro Ser Gln Met Leu Arg Thr Gly
                130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
                180                 185                 190

Thr Thr Gln Ser Arg Leu Gln Phe Ser Gln Ala Gly Ala Ser Asp Ile
                195                 200                 205

Arg Asp Gln Ser Arg Asn Trp Leu Pro Gly Pro Cys Tyr Arg Gln Gln
                210                 215                 220

Arg Val Ser Lys Thr Asp Gly Glu Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
                260                 265                 270

Pro Gln Ser Gly Val Leu Ile Phe Gly Lys Gln Ser Ala Ala Gly Ala
                275                 280                 285

Asp Ile Ala Ile Asp Ser
```

<210> SEQ ID NO 15
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 15

```
Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
        130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Thr Asp Gly Glu Asn Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys
    290
```

<210> SEQ ID NO 16
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 16

```
Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
                35                  40                  45

Leu Asn Phe Lys Leu Phe Asn Ile Gln Val Lys Glu Val Thr Gln Asn
        50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
                100                 105                 110

Tyr Gly Tyr Leu Thr Leu Asn Asn Gly Ser Gln Ala Val Gly Arg Ser
                115                 120                 125

Ser Phe Tyr Cys Leu Glu Tyr Phe Pro Ser Gln Met Leu Arg Thr Gly
            130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
                180                 185                 190

Thr Thr Gln Ser Arg Leu Gln Phe Ser Gln Ala Gly Ala Ser Asp Ile
                195                 200                 205

Arg Asp Gln Ser Arg Asn Trp Leu Pro Gly Pro Cys Tyr Arg Gln Gln
        210                 215                 220

Arg Val Ser Lys Thr Asp Gly Glu Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
                260                 265                 270

Pro Gln Ser Gly Val Leu Ile Phe Gly Lys Gln Gly Ser Glu Lys Thr
            275                 280                 285

Asn Val Asp Ile Glu Lys
        290

<210> SEQ ID NO 17
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 17

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
                35                  40                  45

Leu Asn Phe Lys Leu Phe Asn Ile Gln Val Lys Glu Val Thr Gln Asn
        50                  55                  60
```

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
210                 215                 220

Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys
        290

<210> SEQ ID NO 18
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 18

Asn Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Asn Trp Gly Phe Arg Pro Lys Arg
            35                  40                  45

Leu Asn Phe Lys Leu Phe Asn Ile Gln Val Lys Glu Val Thr Gln Asn
        50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

```
Ser Phe Tyr Cys Leu Glu Tyr Phe Pro Ser Gln Met Leu Arg Thr Gly
            130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Asp Glu Ala Gly Ser
            180                 185                 190

Glu Thr Lys Ser Thr Leu Arg Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys
        290

<210> SEQ ID NO 19
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 19

Asn Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
        35                  40                  45

Leu Asn Phe Lys Leu Phe Asn Ile Gln Val Lys Glu Val Thr Gln Asn
50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190
```

```
Thr Thr Gln Ser Arg Leu Gln Phe Ser Gln Ala Gly Ala Ser Asp Ile
            195                 200                 205
Arg Asp Gln Ser Arg Asn Trp Leu Pro Gly Pro Cys Tyr Arg Gln Gln
        210                 215                 220
Arg Val Ser Lys Thr Asp Gly Glu Asn Asn Ser Asp Phe Ser Trp
225                 230                 235                 240
Thr Gly Ala Thr Lys Tyr His Leu Asn Gly Arg Asp Ser Leu Val Asn
                245                 250                 255
Pro Gly Pro Ala Met Ala Ser His Lys Asp Asp Glu Glu Lys Phe Phe
            260                 265                 270
Pro Gln Ser Gly Val Leu Ile Phe Gly Lys Gln Ser Gly Arg Glu Gly
        275                 280                 285
Asp Ala Glu Ile Glu Asp
    290
```

<210> SEQ ID NO 20
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 20

```
Ala Ser Gly Ala Ser Asn Asp Asn His Tyr Phe Gly Tyr Ser Thr Pro
1               5                   10                  15
Trp Gly Tyr Phe Asp Phe Asn Arg Phe His Cys His Phe Ser Pro Arg
                20                  25                  30
Asp Trp Gln Arg Leu Ile Asn Asn Asn Trp Gly Phe Arg Pro Lys Arg
            35                  40                  45
Leu Asn Phe Lys Leu Phe Asn Ile Gln Val Lys Glu Val Thr Gln Asn
    50                  55                  60
Asp Gly Thr Thr Thr Ile Ala Asn Asn Leu Thr Ser Thr Val Gln Val
65                  70                  75                  80
Phe Thr Asp Ser Glu Tyr Gln Leu Pro Tyr Val Leu Gly Ser Ala His
                85                  90                  95
Gln Gly Cys Leu Pro Pro Phe Pro Ala Asp Val Phe Met Val Pro Gln
            100                 105                 110
Tyr Gly Tyr Leu Thr Leu Asn Asn Gly Ser Gln Ala Val Gly Arg Ser
        115                 120                 125
Ser Phe Tyr Cys Leu Glu Tyr Phe Pro Ser Gln Met Leu Arg Thr Gly
130                 135                 140
Asn Asn Phe Thr Phe Ser Tyr Thr Phe Glu Asp Val Pro Phe His Ser
145                 150                 155                 160
Ser Tyr Ala His Ser Gln Ser Leu Asp Arg Leu Met Asn Pro Leu Ile
                165                 170                 175
Asp Gln Tyr Leu Tyr Leu Ser Arg Thr Asn Thr Pro Ser Gly Thr
            180                 185                 190
Thr Thr Gln Ser Arg Leu Gln Phe Ser Gln Ala Gly Ala Ser Asp Ile
        195                 200                 205
Arg Asp Gln Ser Arg Asn Trp Leu Pro Gly Pro Cys Tyr Arg Gln Gln
    210                 215                 220
Arg Val Ser Lys Thr Asp Gly Glu Asn Asn Ser Asp Phe Ser Trp
225                 230                 235                 240
Thr Gly Ala Thr Lys Tyr His Leu Asn Gly Arg Asp Ser Leu Val Asn
                245                 250                 255
```

Pro Gly Pro Ala Met Ala Ser His Lys Asp Asp Glu Glu Lys Phe Phe
                260                 265                 270

Pro Gln Ser Gly Val Leu Ile Phe Gly Lys Glu Asp Ala Thr Glu Asn
                275                 280                 285

Asn Ile Asp Ile Asp Arg
                290

<210> SEQ ID NO 21
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 21

Ala Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Trp Gly Phe Arg Pro Lys Arg
                35                  40                  45

Leu Asn Phe Lys Leu Phe Asn Ile Gln Val Lys Glu Val Thr Gln Asn
        50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
                100                 105                 110

Tyr Gly Tyr Leu Thr Leu Asn Asn Gly Ser Gln Ala Val Gly Arg Ser
                115                 120                 125

Ser Phe Tyr Cys Leu Glu Tyr Phe Pro Ser Gln Met Leu Arg Thr Gly
                130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
                180                 185                 190

Thr Thr Gln Ser Arg Leu Gln Phe Ser Gln Ala Gly Ala Ser Asp Ile
                195                 200                 205

Arg Asp Gln Ser Arg Asn Trp Leu Pro Gly Pro Cys Tyr Arg Gln Gln
        210                 215                 220

Arg Val Ser Thr Thr Asp Gly Glu Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
                260                 265                 270

Pro Gln Ser Gly Val Leu Ile Phe Gly Lys Glu Asp Ala Thr Glu Asn
                275                 280                 285

Asn Ile Asp Ile Asp Arg
                290

<210> SEQ ID NO 22
<211> LENGTH: 294

```
<212> TYPE: PRT
<213> ORGANISM: Artificial Sequence
<220> FEATURE:
<223> OTHER INFORMATION: Synthetic Polypeptide

<400> SEQUENCE: 22

Gln Ser Gly Ala Trp Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Trp Gly Phe Arg Pro Lys Arg
            35                  40                  45

Leu Asn Phe Lys Leu Phe Asn Ile Gln Val Lys Glu Val Thr Gln Asn
        50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
210                 215                 220

Arg Val Ser Lys Thr Asp Gly Glu Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Glu Asp Ala Thr Glu Asn
        275                 280                 285

Asn Ile Asp Ile Asp Arg
        290

<210> SEQ ID NO 23
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 23

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30
```

Asp Trp Gln Arg Leu Ile Asn Asn Trp Gly Phe Arg Pro Lys Arg
            35                  40                  45

Leu Asn Phe Lys Leu Phe Asn Ile Gln Val Lys Glu Val Thr Lys Asn
     50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Thr Ala Ser Gly Asn
            180                 185                 190

Val Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Arg Asp Asp Asp Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys
    290

<210> SEQ ID NO 24
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 24

Ala Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
            35                  40                  45

Leu Asn Phe Lys Leu Phe Asn Ile Gln Val Lys Glu Val Thr Gln Asn
     50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

```
Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
            130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
            195                 200                 205

Arg Asp Gln Ser Arg Asn Trp Leu Pro Gly Pro Cys Tyr Arg Gln Gln
210                 215                 220

Arg Val Ser Thr Thr Pro Ala Asp Asn Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Gln Gly Ser Glu Lys Thr
            275                 280                 285

Asn Val Asp Ile Glu Lys
        290

<210> SEQ ID NO 25
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 25

Asn Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
            35                  40                  45

Leu Asn Phe Lys Leu Phe Asn Ile Gln Val Lys Glu Val Thr Gln Asn
50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
            130                 135                 140

Asn Asn Phe Thr Phe Ser Tyr Thr Phe Glu Asp Val Pro Phe His Ser
145                 150                 155                 160
```

```
Ser Tyr Ala His Ser Gln Ser Leu Asp Arg Leu Met Asn Pro Leu Ile
            165                 170                 175

Asp Gln Tyr Leu Tyr Phe Leu Ser Arg Thr Asn Thr Ala Ser Gly Asn
            180                 185                 190

Val Thr Gln Ser Thr Leu Gln Phe Ser Gln Ala Gly Ala Ser Asp Ile
            195                 200                 205

Arg Asp Gln Ser Arg Asn Trp Leu Pro Gly Pro Cys Tyr Arg Gln Gln
210                 215                 220

Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
            245                 250                 255

Pro Gly Pro Ala Met Ala Ser His Arg Asp Asp Asp Lys Phe Phe
            260                 265                 270

Pro Gln Ser Gly Val Leu Ile Phe Gly Lys Gln Gly Ser Glu Lys Thr
            275                 280                 285

Asn Val Asp Ile Glu Lys
            290

<210> SEQ ID NO 26
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 26

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
            35                  40                  45

Leu Asn Phe Lys Leu Phe Asn Ile Gln Val Lys Glu Val Thr Gln Asn
50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
            85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
            130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
            165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
            195                 200                 205

Arg Asp Gln Ser Arg Asn Trp Leu Pro Gly Pro Cys Tyr Arg Gln Gln
210                 215                 220
```

```
Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
            245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys
        290

<210> SEQ ID NO 27
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 27

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Gln Asp Ala Glu Asn Asn Ser Glu Phe Ser Trp
225                 230                 235                 240

Pro Gly Ala Thr Lys Tyr His Leu Asn Gly Arg Asp Ser Leu Val Asn
            245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Gln Gly Ser Glu Lys Thr
        275                 280                 285
```

```
Asn Val Asp Ile Glu Lys
    290

<210> SEQ ID NO 28
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 28

Glu Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Val Ser Ala Asp Asn Asn Ser Glu Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Gln Gly Ala Ala Ala Asp
        275                 280                 285

Asp Val Glu Ile Asp Gly
    290

<210> SEQ ID NO 29
<211> LENGTH: 294
<212> TYPE: PRT
<213> ORGANISM: Artificial Sequence
<220> FEATURE:
<223> OTHER INFORMATION: Synthetic Polypeptide
```

<400> SEQUENCE: 29

```
Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
210                 215                 220

Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys
    290
```

<210> SEQ ID NO 30
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

```
<400> SEQUENCE: 30

Ala Xaa Met Xaa Lys Xaa His
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 31

Gly Ala Xaa Asn Met Xaa Thr Xaa Ala Xaa Arg
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 32

Asp Gly Glu Asp Phe
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(9)
<223> OTHER INFORMATION: Xaa can be any naturally occurring amino acid

<400> SEQUENCE: 33

Ala Gly Arg Ala Asp Ile Xaa Xaa Xaa Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 34

Glu Asp Ala Thr Glu Asn Asn Ile Asp Ile Asp Arg
1               5                   10

<210> SEQ ID NO 35
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 35

Arg Asp Asp Asp Asp
1               5

<210> SEQ ID NO 36
<211> LENGTH: 334
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 36

Xaa Xaa Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Gln Asp Ala Glu Asn Asn Ser Glu Phe Ser Trp
225                 230                 235                 240

Pro Gly Ala Thr Lys Tyr His Leu Asn Gly Arg Asp Ser Leu Val Asn
                245                 250                 255

Pro Gly Pro Ala Met Ala Ser His Lys Asp Asp Glu Glu Lys Phe Phe
            260                 265                 270

Pro Gln Ser Gly Val Leu Ile Phe Gly Lys Gln Gly Ser Glu Lys Thr
        275                 280                 285
```

Asn Val Asp Ile Glu Lys Val Met Ile Thr Asp Glu Glu Ile Arg
    290                 295                 300

Thr Thr Asn Pro Val Ala Thr Glu Gln Tyr Gly Ser Val Ser Thr Asn
305                 310                 315                 320

Leu Gln Arg Gly Asn Arg Gln Ala Ala Thr Ala Asp Val Asn
            325                 330

<210> SEQ ID NO 37
<211> LENGTH: 334
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 37

Xaa Xaa Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
        35                  40                  45

Leu Asn Phe Lys Leu Phe Asn Ile Gln Val Lys Glu Val Thr Gln Asn
50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Ser Asp Ser Gly Ile
            180                 185                 190

Asp Thr Gln Ser Asn Leu Met Phe Ser Gln Ala Gly Ala Ser Asp Ile
        195                 200                 205

Arg Asp Gln Ser Arg Asn Trp Leu Pro Gly Pro Cys Tyr Arg Gln Gln
210                 215                 220

Arg Val Ser Lys Thr Ala Ala Asp Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Gly Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys Val Met Ile Thr Asp Glu Glu Ile Arg
290                 295                 300

```
Thr Thr Asn Pro Val Ala Thr Glu Gln Tyr Gly Ser Val Ser Thr Asn
305                 310                 315                 320

Leu Gln Arg Gly Asn Arg Gln Ala Ala Thr Ala Asp Val Asn
                325                 330
```

<210> SEQ ID NO 38
<211> LENGTH: 334
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 38

```
Xaa Xaa Gly Ala Xaa Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Asn Trp Gly Phe Arg Pro Lys Arg
                35                  40                  45

Leu Asn Phe Lys Leu Phe Asn Ile Gln Val Lys Glu Val Thr Gln Asn
            50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
                100                 105                 110

Tyr Gly Tyr Leu Thr Leu Asn Asn Gly Ser Gln Ala Val Gly Arg Ser
                115                 120                 125

Ser Phe Tyr Cys Leu Glu Tyr Phe Pro Ser Gln Met Leu Arg Thr Gly
            130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Asp Pro Ser Gly Ser
                180                 185                 190

Thr Thr Met Ser Thr Leu Arg Phe Ser Gln Ala Gly Ala Ser Asp Ile
            195                 200                 205

Arg Asp Gln Ser Arg Asn Trp Leu Pro Gly Pro Cys Tyr Arg Gln Gln
210                 215                 220

Arg Val Ser Lys Val Ser Ala Asp Asn Asn Ser Glu Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Asp Lys Phe Phe
                260                 265                 270

Pro Gln Ser Gly Val Leu Ile Phe Gly Lys Gln Gly Ser Glu Lys Thr
                275                 280                 285
```

```
Asn Val Asp Ile Glu Lys Val Met Ile Thr Asp Glu Glu Ile Arg
    290                 295                 300

Thr Thr Asn Pro Val Ala Thr Glu Gln Tyr Gly Ser Val Ser Thr Asn
305                 310                 315                 320

Leu Gln Arg Gly Asn Arg Gln Ala Ala Thr Ala Asp Val Asn
                325                 330

<210> SEQ ID NO 39
<211> LENGTH: 334
<212> TYPE: PRT
<213> ORGANISM: Artificial Sequence
<220> FEATURE:
<223> OTHER INFORMATION: Synthetic polypeptide

<400> SEQUENCE: 39

Asn Ala Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
                20                  25                  30

Asp Trp Gln Arg Leu Ile Asn Asn Trp Gly Phe Arg Pro Lys Arg
            35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Thr Asp Gly Glu Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Glu Gly Ser Lys Thr
        275                 280                 285

Asn Val Asp Ile Glu Lys Val Met Ile Thr Asp Glu Glu Ile Arg
    290                 295                 300

Thr Thr Asn Pro Val Ala Thr Glu Gln Tyr Gly Ser Val Ser Thr Asn
305                 310                 315                 320
```

Leu Gln Arg Gly Asn Arg Gln Ala Ala Thr Ala Asp Val Asn
            325                 330

<210> SEQ ID NO 40
<211> LENGTH: 334
<212> TYPE: PRT
<213> ORGANISM: Artificial Sequence
<220> FEATURE:
<223> OTHER INFORMATION: Synthetic polypeptide

<400> SEQUENCE: 40

Asp Ala Gly Ala Thr Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
        115                 120                 125

Ser Phe Tyr Cys Leu Glu Tyr Phe Pro Ser Gln Met Leu Arg Thr Gly
    130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Thr Pro Ser Gly Thr
            180                 185                 190

Ala Thr Met Ser Lys Leu His Phe Ser Gln Ala Gly Ala Ser Asp Ile
        195                 200                 205

Arg Asp Gln Ser Arg Asn Trp Leu Pro Gly Pro Cys Tyr Arg Gln Gln
    210                 215                 220

Arg Val Ser Lys Thr Tyr Asn Asp Asn Asn Ser Glu Phe Ser Trp
225                 230                 235                 240

Thr Gly Ala Thr Thr Tyr His Leu Asn Gly Arg Asp Ser Leu Val Asn
                245                 250                 255

Pro Gly Pro Ala Met Ala Ser His Lys Asp Asp Glu Arg Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys Val Met Ile Thr Asp Glu Glu Ile Arg
    290                 295                 300

Thr Thr Asn Pro Val Ala Thr Glu Gln Tyr Gly Ser Val Ser Thr Asn
305                 310                 315                 320

Leu Gln Arg Gly Asn Arg Gln Ala Ala Thr Ala Asp Val Asn
            325                 330

<210> SEQ ID NO 41
<211> LENGTH: 334

```
<212> TYPE: PRT
<213> ORGANISM: Artificial Sequence
<220> FEATURE:
<223> OTHER INFORMATION: Synthetic polypeptide

<400> SEQUENCE: 41

Gln Ser Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Phe Leu Ser Arg Thr Asn Thr Gly Ala Gly Asn
            180                 185                 190

Met Thr Thr Ser Ala Leu Arg Phe Ser Gln Ala Gly Ala Ser Asp Ile
            195                 200                 205

Arg Asp Gln Ser Arg Asn Trp Leu Pro Gly Pro Cys Tyr Arg Gln Gln
        210                 215                 220

Arg Val Ser Thr Thr Pro Ala Asp Asn Asn Ser Asp Phe Ser Trp
225                 230                 235                 240

Thr Gly Ala Thr Lys Tyr His Leu Asn Gly Arg Asp Ser Leu Val Asn
                245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Gln Gly Ser Glu Lys Thr
        275                 280                 285

Asn Val Asp Ile Glu Lys Val Met Ile Thr Asp Glu Glu Ile Arg
    290                 295                 300

Thr Thr Asn Pro Val Ala Thr Glu Gln Tyr Gly Ser Val Ser Thr Asn
305                 310                 315                 320

Leu Gln Arg Gly Asn Arg Gln Ala Ala Thr Ala Asp Val Asn
            325                 330

<210> SEQ ID NO 42
<211> LENGTH: 334
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
```

<222> LOCATION: (1)..(2)
<223> OTHER INFORMATION: Xaa can be any naturally occurring amino acid

<400> SEQUENCE: 42

```
Xaa Xaa Gly Ala Ser Asn Asp Asn His Tyr Phe Gly Tyr Ser Thr Pro
1               5                   10                  15
Trp Gly Tyr Phe Asp Phe Asn Arg Phe His Cys His Phe Ser Pro Arg
            20                  25                  30
Asp Trp Gln Arg Leu Ile Asn Asn Asn Trp Gly Phe Arg Pro Lys Arg
        35                  40                  45
Leu Asn Phe Lys Leu Phe Asn Ile Gln Val Lys Glu Val Thr Gln Asn
    50                  55                  60
Asp Gly Thr Thr Thr Ile Ala Asn Asn Leu Thr Ser Thr Val Gln Val
65                  70                  75                  80
Phe Thr Asp Ser Glu Tyr Gln Leu Pro Tyr Val Leu Gly Ser Ala His
                85                  90                  95
Gln Gly Cys Leu Pro Pro Phe Pro Ala Asp Val Phe Met Val Pro Gln
            100                 105                 110
Tyr Gly Tyr Leu Thr Leu Asn Asn Gly Ser Gln Ala Val Gly Arg Ser
        115                 120                 125
Ser Phe Tyr Cys Leu Glu Tyr Phe Pro Ser Gln Met Leu Arg Thr Gly
    130                 135                 140
Asn Asn Phe Thr Phe Ser Tyr Thr Phe Glu Asp Val Pro Phe His Ser
145                 150                 155                 160
Ser Tyr Ala His Ser Gln Ser Leu Asp Arg Leu Met Asn Pro Leu Ile
                165                 170                 175
Asp Gln Tyr Leu Tyr Tyr Leu Ser Arg Thr Asn Thr Pro Ser Gly Thr
            180                 185                 190
Thr Thr Gln Ser Arg Leu Gln Phe Ser Gln Ala Gly Ala Ser Asp Ile
        195                 200                 205
Arg Asp Gln Ser Arg Asn Trp Leu Pro Gly Pro Cys Tyr Arg Gln Gln
    210                 215                 220
Arg Val Ser Lys Val Ser Ala Asp Asn Asn Asn Ser Glu Phe Ser Trp
225                 230                 235                 240
Thr Gly Ala Thr Lys Tyr His Leu Asn Gly Arg Asp Ser Leu Val Asn
                245                 250                 255
Pro Gly Pro Ala Met Ala Ser His Lys Asp Asp Glu Glu Lys Phe Phe
            260                 265                 270
Pro Gln Ser Gly Val Leu Ile Phe Gly Lys Gln Gly Ala Ala Ala Asp
        275                 280                 285
Asp Val Glu Ile Asp Gly Val Met Ile Thr Asp Glu Glu Glu Ile Arg
    290                 295                 300
Thr Thr Asn Pro Val Ala Thr Glu Gln Tyr Gly Ser Val Ser Thr Asn
305                 310                 315                 320
Leu Gln Arg Gly Asn Arg Gln Ala Ala Thr Ala Asp Val Asn
                325                 330
```

<210> SEQ ID NO 43
<211> LENGTH: 334
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 43

```
Xaa Xaa Gly Ala Ser Asn Asp Asn His Tyr Phe Gly Tyr Ser Thr Pro
1               5                   10                  15

Trp Gly Tyr Phe Asp Phe Asn Arg Phe His Cys His Phe Ser Pro Arg
            20                  25                  30

Asp Trp Gln Arg Leu Ile Asn Asn Trp Gly Phe Arg Pro Lys Arg
        35                  40                  45

Leu Asn Phe Lys Leu Phe Asn Ile Gln Val Lys Glu Val Thr Gln Asn
    50                  55                  60

Asp Gly Thr Thr Thr Ile Ala Asn Asn Leu Thr Ser Thr Val Gln Val
65                  70                  75                  80

Phe Thr Asp Ser Glu Tyr Gln Leu Pro Tyr Val Leu Gly Ser Ala His
                85                  90                  95

Gln Gly Cys Leu Pro Pro Phe Pro Ala Asp Val Phe Met Val Pro Gln
            100                 105                 110

Tyr Gly Tyr Leu Thr Leu Asn Asn Gly Ser Gln Ala Val Gly Arg Ser
            115                 120                 125

Ser Phe Tyr Cys Leu Glu Tyr Phe Pro Ser Gln Met Leu Arg Thr Gly
130                 135                 140

Asn Asn Phe Thr Phe Ser Tyr Thr Phe Glu Asp Val Pro Phe His Ser
145                 150                 155                 160

Ser Tyr Ala His Ser Gln Ser Leu Asp Arg Leu Met Asn Pro Leu Ile
                165                 170                 175

Asp Gln Tyr Leu Tyr Tyr Leu Ser Arg Thr Asn Thr Pro Ser Gly Thr
            180                 185                 190

Thr Thr Gln Ser Arg Leu Gln Phe Ser Gln Ala Gly Ala Ser Asp Ile
            195                 200                 205

Arg Asp Gln Ser Arg Asn Trp Leu Pro Gly Pro Cys Tyr Arg Gln Gln
210                 215                 220

Arg Val Ser Lys Thr Ser Ala Asp Asn Asn Ser Glu Tyr Ser Trp
225                 230                 235                 240

Thr Gly Ala Thr Lys Tyr His Leu Asn Gly Arg Asp Ser Leu Val Asn
            245                 250                 255

Pro Gly Pro Ala Met Ala Ser His Lys Asp Asp Glu Lys Phe Phe
            260                 265                 270

Pro Gln Ser Gly Val Leu Ile Phe Gly Lys Gln Gly Ala Gly Arg Ala
            275                 280                 285

Asp Ile Asp Ile Glu Ser Val Met Ile Thr Asp Glu Glu Ile Arg
290                 295                 300

Thr Thr Asn Pro Val Ala Thr Glu Gln Tyr Gly Ser Val Ser Thr Asn
305                 310                 315                 320

Leu Gln Arg Gly Asn Arg Gln Ala Ala Thr Ala Asp Val Asn
            325                 330
```

<210> SEQ ID NO 44
<211> LENGTH: 334
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 44

```
Xaa Xaa Gly Ala Xaa Asn Asp Asn His Tyr Phe Gly Tyr Ser Thr Pro
1               5                   10                  15
Trp Gly Tyr Phe Asp Phe Asn Arg Phe His Cys His Phe Ser Pro Arg
            20                  25                  30
Asp Trp Gln Arg Leu Ile Asn Asn Asn Trp Gly Phe Arg Pro Lys Arg
        35                  40                  45
Leu Asn Phe Lys Leu Phe Asn Ile Gln Val Lys Glu Val Thr Gln Asn
    50                  55                  60
Asp Gly Thr Thr Thr Ile Ala Asn Asn Leu Thr Ser Thr Val Gln Val
65                  70                  75                  80
Phe Thr Asp Ser Glu Tyr Gln Leu Pro Tyr Val Leu Gly Ser Ala His
                85                  90                  95
Gln Gly Cys Leu Pro Pro Phe Pro Ala Asp Val Phe Met Val Pro Gln
            100                 105                 110
Tyr Gly Tyr Leu Thr Leu Asn Asn Gly Ser Gln Ala Val Gly Arg Ser
        115                 120                 125
Ser Phe Tyr Cys Leu Glu Tyr Phe Pro Ser Gln Met Leu Arg Thr Gly
    130                 135                 140
Asn Asn Phe Thr Phe Ser Tyr Thr Phe Glu Asp Val Pro Phe His Ser
145                 150                 155                 160
Ser Tyr Ala His Ser Gln Ser Leu Asp Arg Leu Met Asn Pro Leu Ile
                165                 170                 175
Asp Gln Tyr Leu Tyr Tyr Leu Ser Arg Thr Asn Thr Pro Ser Gly Thr
            180                 185                 190
Thr Thr Gln Ser Arg Leu Gln Phe Ser Gln Ala Gly Ala Ser Asp Ile
        195                 200                 205
Arg Asp Gln Ser Arg Asn Trp Leu Pro Gly Pro Cys Tyr Arg Gln Gln
    210                 215                 220
Arg Val Ser Lys Gln Asp Ala Glu Asn Asn Ser Glu Phe Ser Trp
225                 230                 235                 240
Pro Gly Ala Thr Lys Tyr His Leu Asn Gly Arg Asp Ser Leu Val Asn
                245                 250                 255
Pro Gly Pro Ala Met Ala Ser His Lys Asp Asp Glu Glu Lys Phe Phe
            260                 265                 270
Pro Gln Ser Gly Val Leu Ile Phe Gly Lys Gln Ser Ala Ala Gly Ala
        275                 280                 285
Asp Val Ala Ile Asp Ser Val Met Ile Thr Asp Glu Glu Ile Arg
    290                 295                 300
Thr Thr Asn Pro Val Ala Thr Glu Gln Tyr Gly Ser Val Ser Thr Asn
305                 310                 315                 320
Leu Gln Arg Gly Asn Arg Gln Ala Ala Thr Ala Asp Val Asn
                325                 330
```

<210> SEQ ID NO 45
<211> LENGTH: 334
<212> TYPE: PRT
<213> ORGANISM: Artificial Sequence
<220> FEATURE:
<223> OTHER INFORMATION: Synthetic polypeptide

<400> SEQUENCE: 45

Gln Ser Gly Ala Ser Asn Asp Asn His Tyr Phe Gly Tyr Ser Thr Pro

```
            1               5                  10                 15
        Trp Gly Tyr Phe Asp Phe Asn Arg Phe His Cys His Phe Ser Pro Arg
                        20                 25                 30
        Asp Trp Gln Arg Leu Ile Asn Asn Trp Gly Phe Arg Pro Lys Arg
                        35                 40                 45
        Leu Asn Phe Lys Leu Phe Asn Ile Gln Val Lys Glu Val Thr Gln Asn
                50                 55                 60
        Asp Gly Thr Thr Thr Ile Ala Asn Asn Leu Thr Ser Thr Val Gln Val
        65                 70                 75                 80
        Phe Thr Asp Ser Glu Tyr Gln Leu Pro Tyr Val Leu Gly Ser Ala His
                        85                 90                 95
        Gln Gly Cys Leu Pro Pro Phe Pro Ala Asp Val Phe Met Val Pro Gln
                        100                105                110
        Tyr Gly Tyr Leu Thr Leu Asn Asn Gly Ser Gln Ala Val Gly Arg Ser
                        115                120                125
        Ser Phe Tyr Cys Leu Glu Tyr Phe Pro Ser Gln Met Leu Arg Thr Gly
                        130                135                140
        Asn Asn Phe Thr Phe Ser Tyr Thr Phe Glu Asp Val Pro Phe His Ser
        145                150                155                160
        Ser Tyr Ala His Ser Gln Ser Leu Asp Arg Leu Met Asn Pro Leu Ile
                        165                170                175
        Asp Gln Tyr Leu Tyr Tyr Leu Ser Arg Thr Asn Thr Pro Ser Gly Thr
                        180                185                190
        Thr Thr Gln Ser Arg Leu Gln Phe Ser Gln Ala Gly Ala Ser Asp Ile
                        195                200                205
        Arg Asp Gln Ser Arg Asn Trp Leu Pro Gly Pro Cys Tyr Arg Gln Gln
                        210                215                220
        Arg Val Ser Lys Thr Ser Ala Asp Asn Asn Ser Glu Tyr Ser Trp
        225                230                235                240
        Thr Gly Ala Thr Lys Tyr His Leu Asn Gly Arg Asp Ser Leu Val Asn
                        245                250                255
        Pro Gly Pro Ala Met Ala Ser His Lys Asp Asp Glu Glu Lys Phe Phe
                        260                265                270
        Pro Gln Ser Gly Val Leu Ile Phe Gly Lys Gln Gly Ser Glu Lys Thr
                        275                280                285
        Asn Val Asp Ile Glu Lys Val Met Ile Thr Asp Glu Glu Ile Arg
                        290                295                300
        Thr Thr Asn Pro Val Ala Thr Glu Gln Tyr Gly Ser Val Ser Thr Asn
        305                310                315                320
        Leu Gln Arg Gly Asn Arg Gln Ala Ala Thr Ala Asp Val Asn
                        325                330

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 46

Gln Ser Gly Ala Ser
1               5

<210> SEQ ID NO 47
<211> LENGTH: 5
<212> TYPE: PRT
```

<213> ORGANISM: Artificial Sequence
<220> FEATURE:
<223> OTHER INFORMATION: Synthetic Polypeptide

<400> SEQUENCE: 47

Asn Ala Gly Ala Ser
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 48

Thr Thr Gly Ala Thr
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Glu Ala Gly Ala Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 50

Thr Thr Gly Ala Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 51

Gly Ala Gly Ala Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 52

Ala Ser Gly Ala Ser
1               5

<210> SEQ ID NO 53
<211> LENGTH: 5
<212> TYPE: PRT
<213> ORGANISM: Artificial Sequence

```
<220> FEATURE:
<223> OTHER INFORMATION: Synthetic Polypeptide

<400> SEQUENCE: 53

Thr Ala Gly Ala Ser
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 54

Gln Thr Gly Ala Ser
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 55

Arg Xaa Xaa Asp Xaa Arg
1               5

<210> SEQ ID NO 56
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 56

Gln Ser Gly Ala Ser Tyr Leu Ser Arg Thr Asn Thr Pro Ser Gly Thr
1               5                   10                  15

Thr Thr Gln Ser Arg Leu Gln Lys Thr Ser Ala Asp Asn Asn Asn Ser
                20                  25                  30

Glu Tyr Ser Trp Thr Gly Ala Thr Lys Lys Asp Asp Glu Glu Lys Glu
            35                  40                  45

Gly Ser Glu Lys Thr Asn Val Asp Ile Glu Lys Arg Gly Asn Arg Gln
        50                  55                  60

Ala Ala Thr Ala Asp Val Asn
65                  70

<210> SEQ ID NO 57
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 57

Gln Ser Gly Ala Ser Phe Leu Ser Arg Thr Asn Thr Ala Ser Gly Asn
1               5                   10                  15
```

Val Thr Gln Ser Thr Leu Gln Lys Thr Ser Ala Asp Asn Asn Asn Ser
            20                  25                  30

Glu Tyr Ser Trp Thr Gly Ala Thr Lys Arg Asp Asp Asp Lys Gln
        35                  40                  45

Gly Ser Glu Lys Thr Asn Val Asp Ile Glu Lys Arg Gly Asn Arg Gln
    50                  55                  60

Ala Ala Thr Ala Asp Val Asn
65                  70

<210> SEQ ID NO 58
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 58

Asn Ala Gly Ala Ser Tyr Leu Ser Arg Thr Asn Thr Pro Ser Gly Thr
1               5                   10                  15

Thr Thr Gln Ser Arg Leu Gln Lys Thr Ser Ala Asp Asn Asn Asn Ser
            20                  25                  30

Glu Phe Ser Trp Pro Gly Ala Thr Lys Asp Asp Glu Glu Lys Gln
        35                  40                  45

Gly Ser Glu Lys Thr Asn Val Asp Ile Glu Lys Arg Gly Asn Arg Gln
    50                  55                  60

Ala Ala Thr Ala Asp Val Asn
65                  70

<210> SEQ ID NO 59
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 59

Ala Ser Gly Ala Ser Phe Leu Ser Arg Thr Asn Thr Ala Ser Gly Asn
1               5                   10                  15

Val Thr Gln Ser Thr Leu Gln Lys Thr Ser Ala Asp Asn Asn Asn Ser
            20                  25                  30

Glu Tyr Ser Trp Thr Gly Ala Thr Lys Arg Asp Asp Asp Lys Gln
        35                  40                  45

Gly Ser Glu Lys Thr Asn Val Asp Ile Glu Lys Arg Gly Asn Arg Gln
    50                  55                  60

Ala Ala Thr Ala Asp Val Asn
65                  70

<210> SEQ ID NO 60
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 60

Asn Ala Gly Ala Ser Tyr Leu Ser Arg Thr Asn Thr Pro Ser Gly Thr
1               5                   10                  15

Thr Thr Gln Ser Arg Leu Gln Lys Thr Asp Gly Glu Asn Asn Asn Ser
            20                  25                  30

Asp Phe Ser Trp Thr Gly Ala Thr Lys Lys Asp Asp Glu Glu Lys Gln
            35                  40                  45

Gly Ser Glu Lys Thr Asn Val Asp Ile Glu Lys Arg Gly Asn Arg Gln
 50                  55                  60

Ala Ala Thr Ala Asp Val Asn
 65                  70

<210> SEQ ID NO 61
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 61

Ala Ser Gly Ala Ser Tyr Leu Ser Arg Thr Asn Thr Pro Ser Gly Thr
 1               5                  10                  15

Thr Thr Gln Ser Arg Leu Gln Lys Thr Ser Ala Asp Asn Asn Asn Ser
                20                  25                  30

Glu Tyr Ser Trp Thr Gly Ala Thr Lys Lys Asp Asp Asp Asp Lys Gln
            35                  40                  45

Gly Ser Glu Lys Thr Asn Val Asp Ile Glu Lys Arg Gly Asn Arg Gln
 50                  55                  60

Ala Ala Thr Ala Asp Val Asn
 65                  70

<210> SEQ ID NO 62
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 62

Ala Ser Gly Ala Ser Tyr Leu Ser Arg Thr Asn Thr Pro Ser Gly Thr
 1               5                  10                  15

Thr Thr Gln Ser Arg Leu Gln Lys Thr Asp Gly Glu Asn Asn Asn Ser
                20                  25                  30

Asp Phe Ser Trp Thr Gly Ala Thr Lys Lys Asp Asp Glu Glu Lys Gln
            35                  40                  45

Ser Ala Ala Gly Ala Asp Val Ala Ile Asp Ser Arg Gly Asn Arg Gln
            50                  55                  60

Ala Ala Thr Ala Asp Val Asn
 65                  70

<210> SEQ ID NO 63
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 63

Asn Ala Gly Ala Ser Tyr Leu Ser Arg Thr Asn Thr Pro Ser Gly Thr
 1               5                  10                  15

Thr Thr Gln Ser Arg Leu Gln Lys Thr Ser Ala Asp Asn Asn Asn Ser
                20                  25                  30

Glu Tyr Ser Trp Thr Gly Ala Thr Lys Lys Asp Asp Glu Glu Lys Glu
            35                  40                  45

Gly Ser Glu Lys Thr Asn Val Asp Ile Glu Lys Arg Gly Asn Arg Gln

```
            50                  55                  60
Ala Ala Thr Ala Asp Val Asn
 65                 70

<210> SEQ ID NO 64
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 64

Gly Thr Gly Ala Ser Tyr Leu Ser Arg Thr Asn Thr Pro Ser Gly Thr
 1               5                  10                  15

Thr Thr Gln Ser Arg Leu Gln Lys Thr Ser Ala Asp Asn Asn Asn Ser
            20                  25                  30

Glu Phe Ser Trp Thr Gly Ala Thr Thr Arg Asp Asp Asp Glu Arg Gln
        35                  40                  45

Gly Ser Glu Lys Thr Asn Val Asp Ile Glu Lys Arg Gly Asn Arg Gln
    50                  55                  60

Ala Ala Thr Ala Asp Val Asn
 65                 70

<210> SEQ ID NO 65
<211> LENGTH: 71
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 65

Xaa Xaa Gly Ala Ser Tyr Leu Ser Arg Thr Asn Thr Pro Ser Gly Thr
 1               5                  10                  15

Thr Thr Gln Ser Arg Leu Gln Lys Thr Ser Ala Asp Asn Asn Asn Ser
            20                  25                  30

Glu Phe Ser Trp Thr Gly Ala Thr Thr Arg Asp Asp Asp Glu Arg Gln
        35                  40                  45

Gly Ser Glu Lys Thr Asn Val Asp Ile Glu Lys Arg Gly Asn Arg Gln
    50                  55                  60

Ala Ala Thr Ala Asp Val Asn
 65                 70

<210> SEQ ID NO 66
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 66

Leu Ala Leu Gly Glu Thr Thr Arg Pro Ala
 1               5                  10

<210> SEQ ID NO 67
<211> LENGTH: 7
<212> TYPE: PRT
<213> ORGANISM: Artificial Sequence
<220> FEATURE:
<223> OTHER INFORMATION: Synthetic polypeptide
```

<400> SEQUENCE: 67

Asn Arg Gly Thr Glu Trp Asp
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 68

Ala Asp Gly Val Gln Trp Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 69

Gly Glu Ala Arg Ile Ser Ala
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 70

Ser Gly Asn Ser Gly Ala Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 71

Glu Ser Gly Leu Ser Gln Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 72

Glu Tyr Arg Asp Ser Ser Gly
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic polypeptide

```
<400> SEQUENCE: 73

Asp Leu Gly Ser Ala Arg Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 74

Pro Arg Ser Ala Asp Leu Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 75

Pro Arg Ser Thr Ser Asp Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 76

Glu Ser Gly His Gly Tyr Phe
1               5

<210> SEQ ID NO 77
<211> LENGTH: 129
<212> TYPE: PRT
<213> ORGANISM: Unknown
<220> FEATURE:
<223> OTHER INFORMATION: Synthetic

<400> SEQUENCE: 77

Asp Gln Tyr Leu Tyr Phe Leu Ser Arg Thr Asn Gly Gly Ser Gly Asn
1               5                   10                  15

Thr Thr Thr Ser Arg Leu Gly Phe Ser Gln Ala Gly Ala Ser Asp Ile
            20                  25                  30

Arg Asp Gln Ser Arg Asn Trp Leu Pro Gly Pro Cys Tyr Arg Gln Gln
        35                  40                  45

Arg Val Ser Thr Thr Pro Ala Asp Asn Asn Asn Ser Asp Phe Ser Trp
    50                  55                  60

Thr Gly Ala Thr Lys Tyr His Leu Asn Gly Arg Asp Ser Leu Val Asn
65                  70                  75                  80

Pro Gly Pro Ala Met Ala Ser His Lys Asp Asp Thr Gly Lys Phe Phe
                85                  90                  95

Pro Gln Ser Gly Val Leu Ile Phe Gly Lys Gln Gly Ala Gly Gly Thr
            100                 105                 110

Asn Val Asp Ile Glu Gly Val Met Ile Thr Asp Glu Glu Ile Arg
        115                 120                 125

Thr
```

```
<210> SEQ ID NO 78
<211> LENGTH: 129
<212> TYPE: PRT
<213> ORGANISM: Unknown
<220> FEATURE:
<223> OTHER INFORMATION: Synthetic

<400> SEQUENCE: 78

Asp Gln Tyr Leu Tyr Phe Leu Ser Arg Thr Asn Thr Pro Ser Gly Thr
1               5                   10                  15

Thr Thr Gln Ser Arg Leu Gln Phe Ser Gln Ala Gly Ala Ser Asp Ile
            20                  25                  30

Arg Asp Gln Ser Arg Asn Trp Leu Pro Gly Pro Cys Tyr Arg Gln Gln
            35                  40                  45

Arg Val Ser Lys Thr Ser Ala Asp Asn Asn Asn Ser Glu Phe Ser Trp
        50                  55                  60

Thr Gly Ala Thr Lys Tyr His Leu Asn Gly Arg Asp Ser Leu Val Asn
65                  70                  75                  80

Pro Gly Pro Ala Met Ala Ser His Lys Asp Asp Asp Lys Phe Phe
                85                  90                  95

Pro Gln Ser Gly Val Leu Ile Phe Gly Lys Gln Gly Ser Glu Lys Thr
                100                 105                 110

Asn Val Asp Thr Glu Lys Val Met Ile Thr Asp Glu Glu Glu Ile Arg
            115                 120                 125

Thr
```